(12) United States Patent
Covalin et al.

(10) Patent No.: US 12,017,068 B2
(45) Date of Patent: Jun. 25, 2024

(54) DEVICES AND METHODS FOR TREATING MOTION SICKNESS USING ELECTRICAL STIMULATION

(71) Applicant: Spark Biomedical, Inc., Dallas, TX (US)

(72) Inventors: Alejandro Covalin, Los Angeles, CA (US); Navid Khodaparast, Dallas, TX (US); Melanie McWade, Portland, OR (US)

(73) Assignee: Spark Biomedical, Inc., Dallas, TX (US)

( * ) Notice: Subject to any disclaimer, the term of this patent is extended or adjusted under 35 U.S.C. 154(b) by 0 days.

(21) Appl. No.: 18/202,834

(22) Filed: May 26, 2023

(65) Prior Publication Data

US 2023/0381515 A1 Nov. 30, 2023

Related U.S. Application Data

(60) Provisional application No. 63/346,697, filed on May 27, 2022.

(51) Int. Cl.
*A61N 1/36* (2006.01)
*A61N 1/04* (2006.01)

(52) U.S. Cl.
CPC ....... *A61N 1/36036* (2017.08); *A61N 1/0456* (2013.01); *A61N 1/36031* (2017.08); *A61N 1/36034* (2017.08)

(58) Field of Classification Search
CPC ............ A61N 1/36036; A61N 1/36031; A61N 1/36034; A61N 1/0456
See application file for complete search history.

(56) References Cited

U.S. PATENT DOCUMENTS

| 4,014,323 A | 3/1977 | Gilmer et al. |
| 4,690,144 A | 9/1987 | Rise et al. |

(Continued)

FOREIGN PATENT DOCUMENTS

| WO | 2015109018 | 7/2015 |
| WO | 2015179571 | 11/2015 |

(Continued)

OTHER PUBLICATIONS

Filippelli, et al., "Non-insertive Acupuncture and Neonatal Abstinence Syndrome: A Case Series From an Inner-city Safety Net Hospital," Global Advances in Health and Medicine, vol. 1, No. 4, Sep. 2012, pp. 48-52.

(Continued)

*Primary Examiner* — Amanda K Hulbert
(74) *Attorney, Agent, or Firm* — Finch & Maloney PLLC

(57) ABSTRACT

In an illustrative embodiment, systems and methods for providing antiemetic therapy through neuromodulation include positioning a first electrode against or at least partially into a first tissue region on or surrounding a subject's ear such that the first electrode is on, over, or adjacent to one or more first neural structures, positioning a second electrode against or at least partially into a second tissue region on or surrounding the ear such that the second electrode is on, over, or adjacent to one or more second neural structures, delivering a first series of stimulation pulses to the first electrode for modulating peripheral activity via modulating central neural autonomic structures, and delivering a second series of stimulation pulses to the second electrode for increasing availability of central norepinephrine.

21 Claims, 22 Drawing Sheets

(56) References Cited

U.S. PATENT DOCUMENTS

| | | | |
|---|---|---|---|
| 4,865,048 A | 9/1989 | Eckerson | |
| 4,966,164 A | 10/1990 | Colsen et al. | |
| 5,514,175 A | 5/1996 | Kim et al. | |
| 5,593,432 A | 1/1997 | Crowther et al. | |
| 6,077,237 A * | 6/2000 | Campbell | G06F 3/011 607/139 |
| 6,567,702 B1 | 5/2003 | Nekhendzy et al. | |
| 6,697,670 B2 | 2/2004 | Chomenky et al. | |
| 7,386,347 B2 | 6/2008 | Chung et al. | |
| 7,493,171 B1 | 2/2009 | Whitehurst et al. | |
| 7,797,042 B2 | 9/2010 | Dietrich et al. | |
| 7,856,275 B1 | 12/2010 | Paul et al. | |
| 7,986,996 B2 | 7/2011 | Bell | |
| 8,204,601 B2 | 6/2012 | Moyer et al. | |
| 8,506,469 B2 | 8/2013 | Dietrich et al. | |
| 8,554,324 B2 | 10/2013 | Brocke | |
| 8,666,502 B2 | 3/2014 | Hartlep et al. | |
| 8,688,239 B2 | 4/2014 | Hartlep et al. | |
| 8,700,163 B2 | 4/2014 | Terry, Jr. et al. | |
| 8,729,129 B2 | 5/2014 | Tracey et al. | |
| 8,751,020 B2 | 6/2014 | Beck et al. | |
| 8,755,892 B2 | 6/2014 | Amurthur et al. | |
| 8,885,861 B2 | 11/2014 | Beck et al. | |
| 8,914,123 B2 | 12/2014 | Rigaux | |
| 8,918,178 B2 | 12/2014 | Simon et al. | |
| 8,942,814 B2 | 1/2015 | Szeles | |
| 8,965,518 B1 | 2/2015 | Ellrich et al. | |
| 9,089,691 B2 | 7/2015 | Libbus et al. | |
| 9,089,719 B2 | 7/2015 | Simon et al. | |
| 9,101,766 B2 | 8/2015 | Nekhendzy | |
| 9,216,290 B2 | 12/2015 | Terry, Jr. et al. | |
| 9,314,611 B2 | 4/2016 | Zschaeck et al. | |
| 9,415,220 B1 | 8/2016 | Spinelli et al. | |
| 9,662,269 B2 | 5/2017 | Brown et al. | |
| 9,782,584 B2 | 10/2017 | Cartledge et al. | |
| 9,839,577 B2 | 12/2017 | Brown et al. | |
| 1,002,254 A1 | 7/2018 | Pfeifer | |
| 10,010,479 B2 | 7/2018 | Brown et al. | |
| 10,058,478 B2 | 8/2018 | Schnetz et al. | |
| 10,130,809 B2 | 11/2018 | Cartledge et al. | |
| 10,155,114 B2 | 12/2018 | De Ridder | |
| 10,207,106 B2 | 2/2019 | Simon et al. | |
| 10,213,601 B2 | 2/2019 | Simon et al. | |
| 10,279,178 B2 | 5/2019 | Cartledge et al. | |
| 10,322,062 B2 | 6/2019 | Brown et al. | |
| 10,413,719 B2 | 9/2019 | Brown et al. | |
| 10,426,945 B2 | 10/2019 | Tyler et al. | |
| 10,695,568 B1 | 6/2020 | Covalin | |
| 10,780,264 B2 | 9/2020 | Alam | |
| 10,828,461 B2 | 11/2020 | Cartledge et al. | |
| 10,857,360 B2 | 12/2020 | Waclawik | |
| 10,967,182 B2 | 4/2021 | Khodaparast et al. | |
| 11,351,370 B2 | 6/2022 | Covalin et al. | |
| 11,623,088 B2 | 4/2023 | Covalin et al. | |
| 2005/0165460 A1 | 7/2005 | Erfan | |
| 2006/0064139 A1 | 3/2006 | Chung et al. | |
| 2007/0250145 A1 | 10/2007 | Kraus et al. | |
| 2008/0021517 A1 | 1/2008 | Dietrich | |
| 2008/0021520 A1 | 1/2008 | Dietrich | |
| 2008/0051852 A1 | 2/2008 | Dietrich et al. | |
| 2008/0249594 A1 | 10/2008 | Dietrich et al. | |
| 2009/0131995 A1 | 5/2009 | Sloan et al. | |
| 2009/0287035 A1 | 11/2009 | Dietrich et al. | |
| 2010/0057154 A1 | 3/2010 | Dietrich et al. | |
| 2010/0222843 A1 | 9/2010 | Tass et al. | |
| 2010/0262205 A1 | 10/2010 | De Ridder | |
| 2011/0029045 A1* | 2/2011 | Cevette | A61N 1/323 607/2 |
| 2011/0166624 A1 | 7/2011 | Dietrich et al. | |
| 2012/0203309 A1* | 8/2012 | Englehart | A61M 21/02 607/2 |
| 2013/0079862 A1 | 3/2013 | Ellrich | |
| 2013/0150923 A1 | 6/2013 | Schnetz et al. | |
| 2013/0231729 A1 | 9/2013 | Hartlep et al. | |
| 2013/0231730 A1 | 9/2013 | Hartlep et al. | |
| 2014/0046406 A1 | 2/2014 | Ellrich et al. | |
| 2014/0121740 A1 | 5/2014 | Patterson et al. | |
| 2014/0126752 A1 | 5/2014 | Beck et al. | |
| 2014/0135886 A1* | 5/2014 | Cook | A61N 1/36025 607/136 |
| 2014/0142669 A1 | 5/2014 | Cook et al. | |
| 2014/0266752 A1 | 9/2014 | John | |
| 2015/0018925 A1 | 1/2015 | Zschaeck et al. | |
| 2015/0018926 A1 | 1/2015 | Frenkel et al. | |
| 2015/0080986 A9 | 3/2015 | Ellrich et al. | |
| 2015/0165195 A1 | 6/2015 | Hartlep et al. | |
| 2015/0174418 A1 | 6/2015 | Tyler et al. | |
| 2016/0263376 A1 | 9/2016 | Yoo et al. | |
| 2016/0279021 A1 | 9/2016 | Hyde et al. | |
| 2017/0087364 A1 | 3/2017 | Cartledge et al. | |
| 2017/0113057 A1 | 4/2017 | Goodall et al. | |
| 2017/0224990 A1 | 8/2017 | Goldwasser et al. | |
| 2017/0296807 A1 | 10/2017 | Brown et al. | |
| 2017/0368329 A1 | 12/2017 | Tyler et al. | |
| 2018/0085573 A1 | 3/2018 | Alam | |
| 2018/0200522 A1 | 7/2018 | Taca, Jr. | |
| 2018/0296435 A1 | 10/2018 | Brown et al. | |
| 2018/0318585 A1 | 11/2018 | Pfeifer | |
| 2018/0339148 A1 | 11/2018 | Kong | |
| 2019/0046794 A1 | 2/2019 | Goodall et al. | |
| 2019/0111259 A1 | 4/2019 | De Ridder | |
| 2019/0134390 A1 | 5/2019 | Shimada et al. | |
| 2019/0151646 A1 | 5/2019 | Cakmak | |
| 2019/0262229 A1 | 8/2019 | Brown et al. | |
| 2019/0275322 A1 | 9/2019 | Cartledge et al. | |
| 2020/0030608 A1 | 1/2020 | Halpern | |
| 2020/0038658 A1 | 2/2020 | Tyler et al. | |
| 2020/0108250 A1 | 4/2020 | Ireland | |
| 2020/0139124 A1 | 5/2020 | Amurthur | |
| 2020/0197707 A1 | 6/2020 | Covalin | |
| 2020/0238085 A1 | 7/2020 | Khodaparast et al. | |
| 2020/0261688 A1 | 8/2020 | Thoma | |
| 2020/0261722 A1 | 8/2020 | Alataris et al. | |
| 2020/0323684 A1 | 10/2020 | O'Leary et al. | |
| 2020/0345970 A1 | 11/2020 | La Rovere et al. | |
| 2021/0001124 A1 | 1/2021 | Brown et al. | |
| 2021/0038879 A1 | 2/2021 | Pfeifer | |
| 2021/0069505 A1 | 3/2021 | Romine et al. | |
| 2021/0077812 A1 | 3/2021 | Hool et al. | |
| 2021/0213286 A1 | 7/2021 | Covalin et al. | |
| 2022/0305260 A1 | 9/2022 | Covalin et al. | |
| 2023/0149703 A1 | 5/2023 | Covalin et al. | |
| 2023/0414928 A1 | 12/2023 | Covalin et al. | |

FOREIGN PATENT DOCUMENTS

| | | |
|---|---|---|
| WO | 2019005774 | 1/2019 |
| WO | 2021011165 | 1/2021 |

OTHER PUBLICATIONS

Raith, et al., "Laser Acupuncture as An Adjuvant Therapy for a Neonate with Neonatal Abstinence Syndrome (Nas) Due to Maternal Substitution Therapy: Additional Value of Acupuncture," Acupuncture in Medicine, vol. 32, Issue 6, Dec. 1, 2014, pp. 523-524.

Han, et al., "Mobilization of Specific Neuropeptides by Peripheral Stimulation of Identified Frequencies," Physiology, vol. 7, Issue 4, Aug. 1, 1992, pp. 176-180.

Han, Ji-Sheng, "Acupuncture and Endorphins," Neuroscience Letters, No. 361, 2004, pp. 258-261.

Meade, et al., "A Randomized Trial Of Transcutaneous Electric Acupoint Stimulation As Adjunctive Treatment For Opioid Detoxification," Journal of Substance Abuse Treatment, vol. 38, Issue 1, Jan. 2010, pp. 12-21.

Cioca, et al., "A Correlation Between GDV And Heart Rate Variability Measures: A New Measure Of Well Being," Measuring Energy Fields: Current Research, 2004, Backbone Publishing Co. Fair Lawn, USA, pp. 59-64.

Goldstein, Daniel R., "Aging, Imbalanced Inflammation And Viral Infection," Virulence, vol. 1, Issue 4, Jul./Aug. 2010, Landes Bioscience, pp. 295-298.

(56) References Cited

OTHER PUBLICATIONS

AHRQ Safety Program For Mechanically Ventilated Patients Final Report, Prepared by Johns Hopkins Medicine Armstrong Institute for Patient Safety and Quality, Jan. 2017.
Udupa, et al., "Alteration Of Cardiac Autonomic Functions In Patients With Major Depression; A Study Using Heart Rate Variability Measures," Journal of Affective Disorders 100, 2007, pp. 137-141.
Freed, et al., "Antiviral Innate Immunity: Editorial Overview," Journal of Molecular Biology, vol. 426, Issue 6, Mar. 20, 2014, pp. 1129-1132.
Mercante, et al., "Aurical Neuromodulation: The Emerging Concept Beyond The Stimulation Of Vagus And Trigeminal Nerves," Medicines, vol. 5, Issue 1, Jan. 21, 2018, article No. 10.
Barnes, Peter J., "Autonomic Control Of The Lower Airways," Primer on the Autonomic Nervous System (Third Edition), 2012, pp. 201-204.
Vaillancourt, et al., "Autonomic Nervous System Involvement In Pulmonary Arterial Hypertension," Respiratory Research 18, Dec. 4, 2017, article No. 201.
Astrup, et al., "Cardiac Autonomic Neuropathy Predicts Cardiovascular Morbidity And Mortality In Type 1 Diabetic Patients With Diabetic Nephropathy," Diabetes Care, vol. 29, Issue 2, Feb. 1, 2006, pp. 334-339.
Pavlov, et al., "Controlling Inflammation: The Cholinergic Anti-Inflammatory Pathway," Biochemical Society Transactions, vol. 34, Part 6, Oct. 25, 2006, pp. 1037-1040.
Mehta, et al., "COVID-19: Consider Cytokine Storm Syndromes And Immunosuppression," The Lancet, vol. 395, Issue 10229, Mar. 16, 2020, pp. 1033-1034.
Stebbing, et al., "COVID-19: Combining Antiviral And Anti-Inflammatory Treatments," The Lancet Infectious Diseases, vol. 20, No. 4, Feb. 27, 2020, pp. 400-402.
Oke, et al., "From CNI-1493 To The Immunological Homunculus: Physiology of The Inflammatory Reflex, Journal of Leukocyte Biology," vol. 83, Issue 3, Dec. 7, 2007, pp. 512-517.
Boman, Kajsa, "Heart Rate Variability A Possible Measure Of Subjective Wellbeing?," University of Skövde Bachelor Degree Project in Cognitive Neuroscience, 2018.
Young, et al., "Heart-Rate Variability: A Biomarker To Study The Influence Of Nutrition On Physiological And Psychological Health?" Behavioural Pharmacology, vol. 29, Issue 2, Mar. 15, 2018, pp. 140-151.
Aguilera, et al., "Inflammation As A Modulator Of Host Susceptibility To Pulmonary Influenza, Pneumococcal, And Co-Infections," Frontiers In Immunology, vol. 11, Feb. 11, 2020, article No. 105.
Krygier, et al., "Mindfulness Meditation, Well-Being, And Heart Rate Variability: A Preliminary Investigation Into The Impact Of Intensive Vipassana Meditation," International Journal of Pyschophysiology, vol. 89, Issue 3, Sep. 2013, pp. 305-313.
Chiluwal, et al., "Neuroprotective Effects Of Trigeminal Nerve Stimulation In Severe Traumatic Brain Injury," Scientific Reports, vol. 7, Jul. 28, 2017, article No. 6792.
Cohen, et al., "Power Spectrum Analysis And Cardiovascular Morbidity In Anxiety Disorders," Autonomic Neuroscience, vol. 128, Issues 1-2, Jul. 30, 2006, pp. 1-8.
De Godoy, et al., "Preoperative Nonlinear Behavior In Heart Rate Variability Predicts Morbidity And Mortality After Coronary Artery Bypass Graft Surgery," Medical Science Monitor, vol. 15, Issue 3, Feb. 21, 2009, pp. CR117-CR122.
Pavlov, et al., "The Cholinergic Anti-Inflammatory Pathway," Brain, Behavior, and Immunity, vol. 19, Issue 6, May 26, 2005, pp. 493-499.
Pavlov, et al., "The Cholinergic Anti-Inflammatory Pathway: A Missing Link In Neuroimmunomodulation," Molecular Medicine, vol. 9, No. 5-8, Jun. 30, 2003, pp. 125-134.
Yamada, et al., "The Cholinergic Anti-Inflammatory Pathway: An Innovative Treatment Strategy For Respiratory Diseases And Their Comorbidities," Current Opinion in Pharmacology, vol. 40, Jan. 12, 2018, pp. 18-25.
Geisler, et al., "The Impact Of Heart Rate Variability On Subjective Well-Being Is Mediated By Emotion Regulation," Personality and Individual Differences, vol. 49, Issue 7, Jul. 9, 2010, pp. 723-728.
Seifert, Hilary, "The Inflammatory Response Initiated By The Spleen To Ischemic Stroke," University of South Florida Graduate Theses and Dissertations, Jan. 2013.
Nuntaphum, et al., "Vagus Nerve Stimulation Exerts Cardioprotection Against Myocardial Ischemia/Reperfusion Injury Predominantly Through Its Efferent Vagal Fibers," Basic Research In Cardiology, vol. 113, May 9, 2018, article No. 22.
Tilbrook, A J, "Neuropeptides, Stress-Related," Encyclopedia of stress, vol. 2, 2007, pp. 903-908.
Hutson, et al., "Region-Specific Contribution of the Ventral Tegmental Area to Heroin-Induced Conditioned Immunomodulation," Brain Behav Immun., vol. 38, May 2014, pp. 118-124, DOI: 10.1016/j.bbi.2014.01.008.
Veening, Jan G., and Barendregt, Henk P., "The effects of Beta-Endorphin: state change modification," Fluids and Barriers of the CNS, 12:3, Jan. 2015, pp. 1-22, DOI: 10.1186/2045-118-12-3.
Eisenstein, Toby K., "The Role of Opioid Receptors in Immune System Function," Frontiers in Immunology, vol. 10, Article 2904, Dec. 20, 2019, DOI: 10.3389/fimmu.2019.02904.
Veening, et al., "Volume transmission of beta-endorphin via the cerebrospinal fluid; a review," Fluids and Barriers of the CNS, 9:16, Aug. 2012, pp. 1-16, DOI:10.1186/2045-8118-9-16.
Janes, et al., "An Increase in Tobacco Craving Is Associated with Enhanced Medial Prefrontal Cortex Network Coupling," PLOS ONE, vol. 9, Issue 2: e88228, Feb. 2014, pp. 1-5, DOI:10.1371/journal.pone.0088228.
Hayashi, et al., "Dorsolateral prefrontal and orbitofrontal cortex interactions during self-control of cigarette craving," Proceedings of the National Academy of Sciences of the United States of America, vol. 110, No. 11, Mar. 12, 2013, pp. 4422-4427, DOI: 10.1073/pnas/1212185110.
Karkhanis, et al., "Dynorphin/Kappa Opioid Receptor Signaling in Preclinical Models of Alcohol, Drug, and Food Addiction," International Review of Neurobiology, Jan. 2017, pp. 1-36, DOI: 10.1016/bs.im.2017.08.001.
Gottfried, et al., "Encoding Predictive Reward Value in Human Amygdala and Orbitofrontal Cortex," Science Mag., vol. 301, Issue 5636, Aug. 22, 2003, pp. 1104-1107, DOI: 10.1126/science.1087919.
Alizadehgoradel, et al., "Repeated stimulation of the dorsolateral-prefrontal cortex improves executive dysfunctions and craving in drug addiction: A randomized, double-blind, parallel-group study," Brain Stimulation, vol. 13, Issue 3, Jan. 5, 2020, pp. 582-593, DOI: 10.1016/j.brs.2019.12.028.
Altshuler, et al., "Role of orbitofrontal cortex in incubation of oxycodone craving in male rats," Addiction Biology, Jun. 22, 2020, vol. 26, Issue 2, e12927, pp. 1-11, DOI: 10.1111/adb.12927.
Li, et al., "The Central Amygdala Nucleus is Critical for Incubation of Methamphetamine Craving," Neuropsychopharmacology, vol. 40, Jan. 7, 2015, pp. 1297-1306, DOI: 10.1038/npp.2014.320.
Childs, et al., "Vagus nerve stimulation reduces cocaine seeking and alters plasticity in the extinction network," Cold Spring Harbor Laboratory Press, vol. 24, 2016, pp. 35-42, DOI: 10.1101/lm.043539.116.
Bloom, et al., "Neurons containing beta-endorphin in rat brain exist separately from those containing enkephalin: immunocytochemical studies," Proc. Natl. Acad. Sci. USA, vol. 75, No. 3, Mar. 1978, pp. 1591-1595.
Sailer, et al., "Altered reward processing in the nucleus accumbens and mesial prefrontal cortex of patients with posttraumatic stress disorder," Neuropsychologia, 46:11, May 2008, pp. 2836-2844, DOI: 10.1016/j.neuropsychologia.2008.05.022.
Neylan, Thomas C., "Frontal Lobe Moderators and Mediators of Response to Exposure Therapy in PTSD," Am J Psychiatry, 174:12, Dec. 2017, pp. 1131-1133, DOI: 10.1176/appi.ajp.2017.17091056.
Mehta, et al., "Inflammation, reward circuitry and symptoms of anhedonia and PTSD in trauma-exposed women," Social Cognitive and Affective Neuroscience, vol. 15, Issue 10, 2020, pp. 1046-1055, DOI: 10.1093/scan/nsz100.

(56) References Cited

OTHER PUBLICATIONS

Boukezzi, et al., "Posttraumatic Stress Disorder is associated with altered reward mechanisms during the anticipation and the outcome of monetary incentive cues," NeuroImage: Clinical, vol. 25, 102073, 2020, DOI: 10.1016/j.nicl.2019.102073.

Sherin, Jonathan E., and Nemeroff, Charles B., "Post-traumatic stress disorder: the neurobiological impact of psychological trauma," Dialogues in Clinical Neuroscience, vol. 13, No. 3, 2011, pp. 263-278.

Somohano, et al., "PTSD symptom clusters and craving differs by primary drug of choice," J Dual Diagn., 15(4), 2019, pp. 233-242, DOI: 10.1080/15504263.2019.1637039.

Elman, et al., "Reward and aversion processing in patients with post-traumatic stress disorder: functional neuroimaging with visual and thermal stimuli," Translational Psychiatry, 8:240, Nov. 2018, pp. 1-15, DOI: 10.1038/s41398-018-0292-6.

Seidemann, et al., "The Reward System and Post-Traumatic Stress Disorder: Does Trauma Affect the Way We Interact With Positive Stimuli?" Chronic Stress, vol. 5, Feb. 25, 2021, pp. 1-11, DOI: 10.1177/2470547021996006.

Torrisi, et al., "Therapeutic Challenges of Post-traumatic Stress Disorder: Focus on the Dopaminergic System," Frontiers in Pharmacology, vol. 10, Article 404, Apr. 17, 2019, pp. 1-11, DOI: 10.3389/fphar.2019.00404.

Basner, et al., "Continuous and Intermittent Artificial Gravity as a Countermeasure to the Cognitive Effects of 60 Days of Head-Down Tilt Bed Rest," Frontiers in Physiology, vol. 12, Article 643854, Mar. 17, 2021, pp. 1-14, DOI: 10.3389/fphys.2021.643854.

Jenkins, et al., "Transcutaneous Auricular Neurostimulation (tAN): A Novel Adjuvant Treatment in Neonatal Opioid Withdrawal Syndrome," Frontiers in Human Neuroscience, vol. 15, Article 648556, Mar. 8, 2021, pp. 1-12, DOI: 10.3389/fnhum.2021.648556.

U.S. Department of Veterans Affairs, Pain Management Opioid Taper Decision Tool, A VA Clinician's Guide, Oct. 2016, IB 10-939 P96820.

Opioid Oral Morphine Milligram Equivalent (MME) Conversion Factors, Aug. 2017. Available at: https://www.cms.gov/Medicare/Prescription-Drug-coverage/PrescriptionDrugCovContra/Downloads/Opioid-Morphine-EQ-Conversion-Factors-Aug-2017.pdf.

U.S. Department of Health and Human Services, Centers for Disease Control and Prevention, Calculating Total Daily Dose of Opioids for Safer Dosage. Available at: https://www.cdc.gov/opioids/providers/prescribing/pdf/calculating-total-daily-dose.pdf. Accessed Jun. 1, 2023.

Rong et al., "Transcutaneous vagus nerve stimulation for the treatment of depression: A study protocol for a double blinded randomized clinical trial," BMC Complementary and Alternative Medicine, 2012, 6 pages, 12:255.

Final Office Action mailed in related U.S. Appl. No. 17/750,109 dated Aug. 17, 2023, 14 pages.

\* cited by examiner

DEVICES AND METHODS FOR TREATING MOTION SICKNESS USING ELECTRICAL STIMULATION

CROSS-REFERENCE TO RELATED APPLICATIONS

This application claims priority to U.S. Provisional Patent Application No. 63/346,697 entitled "Devices and Methods for Treating Motion Sickness Using Electrical Stimulation" and filed May 27, 2022. This application is related to U.S. Patent Application Publication No. 2023/0149703 entitled "Devices and Methods for Treating Stress and Improving Alertness Using Electrical Stimulation," U.S. Pat. No. 11,623,088 entitled "Devices and Methods for the Treatment of Substance Use Disorders," U.S. Pat. No. 11,351,370 entitled "Devices and Methods for Treating Cognitive Dysfunction and Depression using Electrical Stimulation," U.S. Pat. No. 10,967,182 entitled "Devices and Methods for Reducing Inflammation Using Electrical Stimulation," and U.S. Pat. No. 10,695,568 entitled "Device and Method for the Treatment of Substance Use Disorders." All above identified applications are hereby incorporated by reference in their entireties.

BACKGROUND

Motion sickness is a common and complex syndrome that occurs in response to real or perceived motion. Motion sickness is triggered when an imbalance in the autonomic nervous system is generated by a mismatch between incoming and expected sensory inputs. The incoming sensory inputs include vestibular, visual, and somatosensory inputs. This mismatching scenario results in a response that involves important autonomic circuits in the brain such as hypothalamic, histaminergic, norepinephrine (NE) as well as cholinergic circuits. The overall autonomic response manifests as motion sickness. Sub-conditions of motion sickness include, e.g., terrestrial motion sickness (e.g., in a car, an airplane, or at sea), simulator motion sickness (e.g., virtual reality environments) and space motion sickness (e.g., in microgravity environments).

Common symptoms of motion sickness include cold sweats, nausea, vomiting, dry heaves, headache, dizziness, lightheadedness, spinning sensation, fatigue, irritability, drowsiness, salivation, vertigo, and spatial disorientation, among others. In some cases, people suffering from motion sickness may experience what is called sopite syndrome, which consists of profound drowsiness and fatigue, apathy, depression, disinclination for work, decreased participation in group activities, malaise, lethargy and agitation that can persist for hours to days after the motion sickness triggering event. In other cases, sufferers continue to feel movement after there is no longer motion, which is known as mal de débarquement (MDD). Motion sickness has also been sometimes conceptualized as a poison response, with corresponding autonomic responses including a stress response and an emesis response.

Consequences of motion sickness scenarios can range from a passenger in a cruise ship feeling sick to an astronaut endangering a space mission, as well as, for example, a commercial or military airplane pilot endangering his or her life along with that of their passengers. Motion sickness that leads to spatial disorientation may result in aviation mishap.

There are several interventions currently being used to counteract motion sickness symptoms. Antihistamine drugs, particularly centrally acting antihistamines that cross the blood-brain-barrier, are the most common approach. For example, antihistamine interventions that limit the activity at HI receptors (HI antagonists) in the CNS have been shown to be effective against motion sickness, e.g., Dimenhydrinate (i.e., Dramamine®). However, these interventions have an undesirable sedative effect, which, in many scenarios typical of various motion sickness sub-conditions (e.g., an airplane pilot or an eSport athlete on a virtual reality platform), is entirely prohibitive.

Anticholinergic as well as adrenergic/sympathomimetics agents may also be effective in overcoming the autonomic imbalance manifested as motion sickness. Anticholinergic agents have been shown to be effective in preventing motion sickness. Although the specific mechanisms of action have not been fully identified, evidence suggests that the anticholinergic agents act on hippocampal circuits to impair the comparison between expected and actual sensory inputs and thereby reduce mismatch signaling. As with antihistamines, however, anticholinergic agents also produce an undesirable sedative effect.

Sympathomimetics interventions such as amphetamines have been shown to be effective in treating motion sickness. Data suggests that neural mismatch signaling reduces the availability of norepinephrine (NE) by GABAergic inhibition of Locus Coeruleus (LC) neuronal activity. Sympathomimetics interventions, which tend to increase NE availability, are thought to counteract GABAergic inhibition. However, prolonged use of sympathomimetics substances may lead to addiction. In some scenarios under which a sedative effect is not desirable, a combination of an anticholinergic and a sympathomimetic are used. For example, during space flights a combination of scopolamine (anticholinergic) and dextroamphetamine (sympathomimetic) is commonly used.

There are other less common pharmacological interventions used to treat or that have the potential to treat motion sickness. For example, rizatriptan, a serotonin 1B/1D receptor agonist used to treat migraine, has been shown to prevent motion sickness in prone migraine individuals. Other serotonin 5-HT receptor agonists, e.g., 5-HT 1A receptor agonists, have also shown anti motion sickness effects. Neuronal activity in the vestibular nuclei has been shown to be downregulated by 5-HT 1A agonists, suggesting that the action of 5-HT in the vestibular nuclei attenuates incoming vestibular sensory signals that may trigger motion sickness.

Another medication that may help alleviate motion sickness symptoms is Loperamide, which is a synthetic antidiarrheal. Loperamide is a peripherally acting μ-opioid receptor agonist which has been shown to reduce rotational induced motion sickness.

In general, drug therapies are often inadequate and too slow acting to treat acute motion sickness symptoms in real time. Moreover, side effects such as drowsiness, decreased cognitive and motor skills, sedation, or inattentiveness prevent their use in some occupations. Few motion sickness sufferers or their prescribing physician would use drug therapies with addictive consequences as their first choice; in fact, many would prefer not to use this type of therapy at all.

SUMMARY OF ILLUSTRATIVE EMBODIMENTS

The inventors recognized the use of noninvasive neuromodulation of cranial nerves would be a highly beneficial primary or augmented treatment for motion sickness. In one aspect, the therapy system and methods of the present disclosure relate to reducing or eliminating symptoms of motion sickness through neuromodulation (e.g., vagal and/or trigeminal stimulation). In another aspect, the therapy system and methods of the present disclosure relate to inhibiting the physiological triggers of motion sickness through neuromodulation. Thus, the methods and systems described herein may both attend symptoms as well as limit the triggering of motion sickness. Although described in relation to motion sickness, therapies, systems, and apparatus described herein may additionally be used to treat the symptoms and/or triggers of certain types of vertigo.

Using the therapy systems and methods described herein, motion sickness may be treated on several fronts. In some embodiments, the system and methods of the present disclosure are effective at modulating production of NE through activation of LC neurons, resulting in increased availability of central NE. The increase in central NE availability produces a similar effect to that of the sympathomimetics interventions, for example by counteracting GABAergic inhibition of LC-NE circuits manifested in motion sickness. Accordingly, the systems and methods of the present disclosure may be used in lieu of, or in combination with, such pharmacological treatments.

In some embodiments the system and methods of the present disclosure increase 5-HT availability as activity in the RN is upregulated. This increase in 5-HT is qualitatively comparable with Rizatriptan-based therapy, discussed above. Data suggests that activation of Vestibular Nuclei (VN) afferent serotonergic neurons from the RN produces an inhibitory effect in VN activity, which, in turn, decreases the VN efferent signals involved in the triggering of motion sickness. Accordingly, the systems and methods of the present disclosure may be used in lieu of, or in combination with, such pharmacological treatments.

Furthermore, the systems and methods of the present disclosure, in some embodiments, modulate central neural autonomic structures (CNAS) to produce a whole body response by triggering or by modulating peripheral activity. For example, an increase in pituitary activity via the Paraventricular Hypothalamic Nucleus (PVN), both the pituitary and the PVN being example CNAS, produces an increase in peripheral circulating β-endorphins, thus modulating peripheral activity in many organs that have β-endorphin receptors. This mimics the above-mentioned pharmacological intervention with Loperamide. Thus, as explained above, embodiments of the present disclosure may qualitatively mimic at least three pharmacological interventions that are known to have a positive outcome when treating motion sickness. In another example, CNAS such as the NTS can be modulated to effectively modulate peripheral activity in the spleen, thus triggering a whole-body anti-inflammatory response. In yet another example, modulation of the Nucleus Ambiguus (NA), which is a CNAS, can lead to an increase in parasympathetic tone, thus activating a peripheral cardiovascular response. In an additional example, modulation of the LC (a CNAS) can modulate peripheral activity at the adrenal medulla, thus increasing catecholamines circulation.

In some implementations, the therapy system includes a treatment device that allows the proposed therapy to be easily and reliably applied by almost anyone at a relatively low cost. Some advantages of the treatment device, in addition to those described above, include ease of use in both the application of the device, customizing therapeutic settings, and the actual wearing of the device, minimal risk of infection, users have the ability to safely self-administer or restart the treatment without the oversight of a clinician.

In a preferred embodiment, a therapy system includes a treatment device having an auricular component configured to be in contact with a patient and a pulse generator or controller configured to communicate with the treatment device. In some implementations, a treatment device can be provided as an assembled unit or as several pieces configured for connection prior to use. In an example, the auricular component can be provided in a sealed pouch and a pulse generator can be provided to connect the auricular component to a connector on the pulse generator. In an aspect, the system is configured to have a removable stimulator without the need to remove the auricular component and vice-versa. In an example, the earpiece can be placed around the auricle of the patient before or after connection to the pulse generator.

In some implementations, the treatment device can be used to provide therapy including a neurostimulation configured to stimulate pathways modulating endogenous 5-HT release. In some implementations, the treatment device can be used to provide therapy including a first neurostimulation configured to stimulate pathways modulating catecholamine release, including the release of norepinephrine. In some implementations, the treatment device can be used to provide therapy including a neurostimulation configured to stimulate pathways modulating endorphin release. In some implementations, the treatment device can be used to provide therapy including a neurostimulation configured to stimulate pathways modulating release of one or more of endogenous 5-HT, catecholamines, and/or endorphins. In some implementations, the treatment device can be used to provide therapy including a plurality of neurostimulations configured to stimulate pathways modulating release of two or more of endogenous 5-HT, catecholamines, and/or endorphins.

In an example, a first neurostimulation can be a low frequency stimulation and a second neurostimulation can be a high frequency. In an example, the pathways modulating 5-HT and/or catecholamine release can include at least one of the auricular branches of the vagus nerve, the lesser occipital nerve, and the great auricular nerve. In an example, the pathways modulating endorphins release can include stimulation of endorphins pathway via stimulation of the Arcuate nucleus of the hypothalamus.

To provide the therapy, a provider or user may adjust therapy parameters as needed and start the therapy using the controls on either the pulse generator or the peripheral device. In some implementations, the therapy includes providing two or more simultaneous and/or synchronized, and/or interleaved stimulations. In an aspect, the therapy can involve applying a first stimulation having a first set of parameters at a first portion of the patient's skin and applying a second stimulation having a second set of parameters at a second portion of the patient's skin. When therapy is done, the user may remove the earpiece and disconnect the earpiece from the pulse generator. In an example, the used earpiece can be replaced with a new earpiece for the next session.

In some embodiments, the earpiece and the pulse generator are integrated in the form of a single component, such that the pulse generator, as well as its power source (e.g., battery) are located in the same housing as the earpiece.

In some embodiments, treatment can be applied unilaterally (left or right) and yet in other embodiments a bilateral treatment may be applied. In the case of a bilateral application two devices could be used; these two devices could be synchronized for yet a better systemic response. A single device with more channels or a single device multiplexing the outputs could also be used for a bilateral application.

One of the advantages of the systems and methods of the present disclosure over these pharmacological interventions is that they are not systemically administered. Moreover, the systems and methods have no known side effects such as, e.g., drowsiness and sedation, and they are not addictive.

The therapeutic methods, systems, and devices of the present disclosure may be applied in a variety of circumstances and used by various individuals. For example, the therapeutic methods, systems, and devices may be used by ship or other watercraft passengers or personnel; airplane pilots, crew or passengers; spacecraft astronauts (e.g., space adaptation syndrome or "space sickness"); or drivers and passengers of automobiles or other land-based transportation. The therapeutic methods, systems, and devices may be used in different environments and under various conditions. For example, the therapeutic methods, systems, and devices may be used by astronauts in a space environment under high radiation conditions. The therapeutic methods, systems, and devices may be used by pilots or flight trainees at altitude and/or under high G-force conditions. The therapeutic methods, systems, and devices may also be used in wet conditions, e.g., in connection with use on and/or under the water, such as by scuba divers. The therapeutic devices may include differing design elements based on the conditions of use. For example, a device for use in high G-force may include elements for ensuring tight contact and secure placement of the therapeutic device. In another example, a device for use in water operations such as a military beach landing or scuba mission may include waterproofing elements to ensure utility of the device under wet conditions. The therapeutic methods, systems, and devices may be used either in actual or simulated conditions involving situations, vessels, and/or events commonly leading to motion sickness symptoms. The therapeutic methods, systems, and devices, in some examples, may be used by an e-athlete during competition, by military or astronaut personnel during training and/or active missions, and/or by pilots during flights or flight simulation training. The therapeutic methods, systems, and devices may be administered in various ways. For example, the therapeutic methods, systems, and devices described herein may be used in real-time to treat symptoms of motion sickness or prophylactically to prevent motion sickness. The therapeutic methods, systems, and devices may be employed in a method of treatment administered by a clinician or other health professional or directly by the user with or without medical supervision.

At least a therapeutic delivery portion of treatment device, in some embodiments, is attached to or integrated with a head-mounted device or system. For example, electrodes and pulse delivery circuitry may be connected to or built into a head-mounted device or system. The head-mounted device or system, in some examples, may include a virtual reality (VR) helmet, VR goggles, a protective helmet (e.g., a pilot helmet, a military helmet, a crash helmet, etc.), a protective helmet with VR heads-up display, a space helmet to be worn by an astronaut, or a communications headset. The pulse generator and/or controller, for example, may be separate from the head-mounted device or system or also integrated into the head-mounted device or system. The head-mounted device or system may be augmented by therapeutic neuromodulation to support a wearer of the head-mounted device or system during activities where the head-mounted device or system is needed, such as while piloting a plane, maneuvering in microgravity, or participating in a VR training exercise involving significant motion simulation.

Chemotherapy is known to induce nausea and vomiting in cancer patients (i.e., chemotherapy-induced nausea and vomiting or CINV). There are several pharmacotherapies used to prevent and treat CINV. However, despite advancements, more than 30% (in some cases up to 60%), of cancer patients undergoing chemotherapy experience CINV. CINV can lead to severe consequences including non-compliance with the cancer treatment. Among other, current treatments include pharmacologic agents with antiemetic and anxiolytic effects. Both effects can be attained via vagal stimulation; furthermore, an anti-anxiety effect has also been shown by trigeminal stimulation. The therapeutic methods, systems, and devices described herein may be used to prevent and/or treat CINV by applying stimulation before, during, and/or after the chemotherapy session.

The forgoing general description of the illustrative implementations and the following detailed description thereof are merely exemplary aspects of the teachings of this disclosure and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings.

DETAILED DESCRIPTION OF ILLUSTRATIVE EMBODIMENTS

Figure 1A:
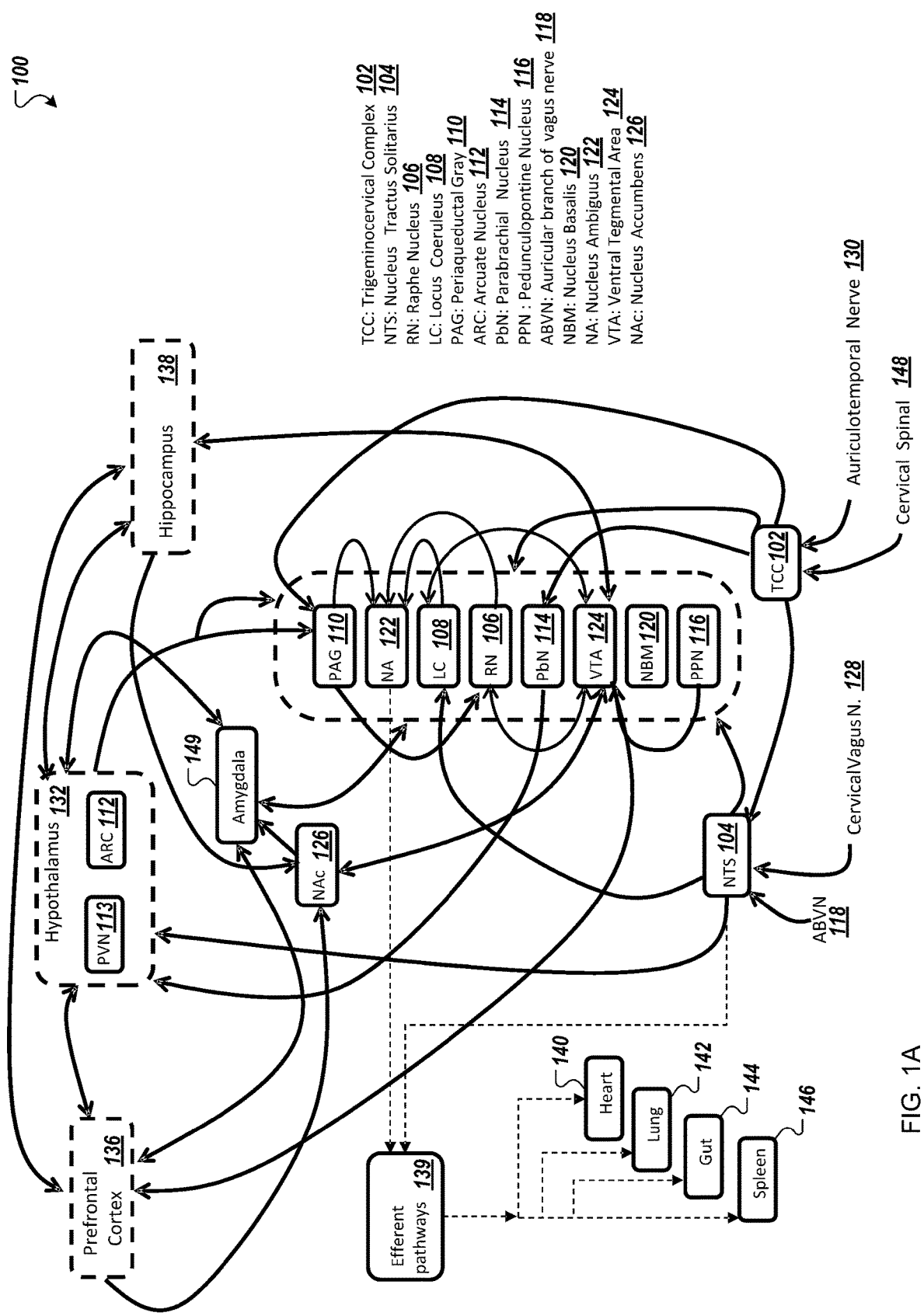
FIGS. 1A and 1B are drawings identifying example neural structures and pathways for delivering therapeutic treatment for motion sickness.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

In some implementations, treatment systems, devices, and methods for stimulation of neural structures on and surrounding a patient's ear are designed for providing stimulation without piercing the dermal layers on or surrounding the ear (e.g., transcutaneous stimulation). Electrodes may be frictionally and/or adhesively retained against the skin on and surrounding the patient's ear to target various nerve structures. The electrodes may have a substantial surface area in comparison to prior art systems relying upon dermal-piercing electrodes, such that multiple nerve terminals are stimulated by a single electrode during therapy. For example, a number of nerve terminals may be situated directly beneath and/or beneath and closely adjacent to the skin upon which the electrode is positioned. By targeting multiple nerve terminals, in some embodiments, positioning of each electrode does not necessarily need to be precise. Therefore, for example, a patient or caregiver may be able to apply and remove the device as desired/needed (e.g., for sleeping, showering, etc.). Further, targeting multiple nerve terminals is advantageous since stimulating multiple branches of a nerve elicits a stronger response than stimulating a single branch, which is the case when using pinpoint electrodes such as needle electrodes.

Although example implementations described herein relate to auricular transcutaneous stimulation, transcutaneous access to target nerve structures, such as vagal and trigeminal nerves and/or nerve branches, is not limited to the auricular branch of the vagus nerve (ABVN) and the auriculotemporal nerve. For example, the vagus nerve, as it ascends inside the carotid sheath along the neck, approaches the subcutaneous region. Trigeminal nerves approach the subcutaneous region at several locations in the face; for example, the supraorbital nerve, supratrochlear nerve, Infratrochlear nerve, the palpebral branch of the lacrimal nerve, the external nasal nerve, the infraorbital nerve, the zygomaticofacial nerve, the zygomaticotemporal nerve, the mental nerve, and the buccal nerve are potential trigeminal targets to deliver transcutaneous stimulation. A device enabling positioning of electrodes against a subject's skin such that any of these branches is stimulated, for example, may trigger responses related to trigeminal stimulation described below. In illustration, a device enabling stimulation of one or more of the above-noted branches may be used to reduce bleed time and/or bleed volume when stimulating in a prophylactic fashion and/or after an injury that has caused bleeding to occur. For example, a device such as the one described by Simon, et al, in U.S. Pat. No. 10,207,106 could be utilized to trigger a vagal response. In a similar manner, the device such as that described by Rigaux in U.S. Pat. No. 8,914,123 can be used to trigger such responses. Furthermore, it is recognized that both devices could be used simultaneously or in an alternative manner to elicit a vagal, a trigeminal, or a trigeminal-vagal response.

In some implementations, methods described herein for stimulation of neural structures on and surrounding a patient's ear may be applied using devices designed for providing percutaneous stimulation. For example, electrodes having tissue-penetrating portions and/or electrodes designed to penetrate tissue (e.g., needle electrodes) may be inserted in a minimally invasive manner (e.g., through at least a top dermal layer of a patient's skin). An example percutaneous auricular stimulation device is the P-STIM® device by Biegler GmbH, described, for example, in U.S. Pat. No. 10,058,478 to Schnetz et al., incorporated herein by reference in its entirety. Percutaneous stimulation, in other embodiments, may be performed at other locations on a subject's skin, for example including the regions described above in relation to transcutaneous stimulation.

In some embodiments, vagal neural structures can be activated by modulating the cervical vagus as it ascends along the neck via non-penetrating and/or penetrating electrodes.

Figure 1B:
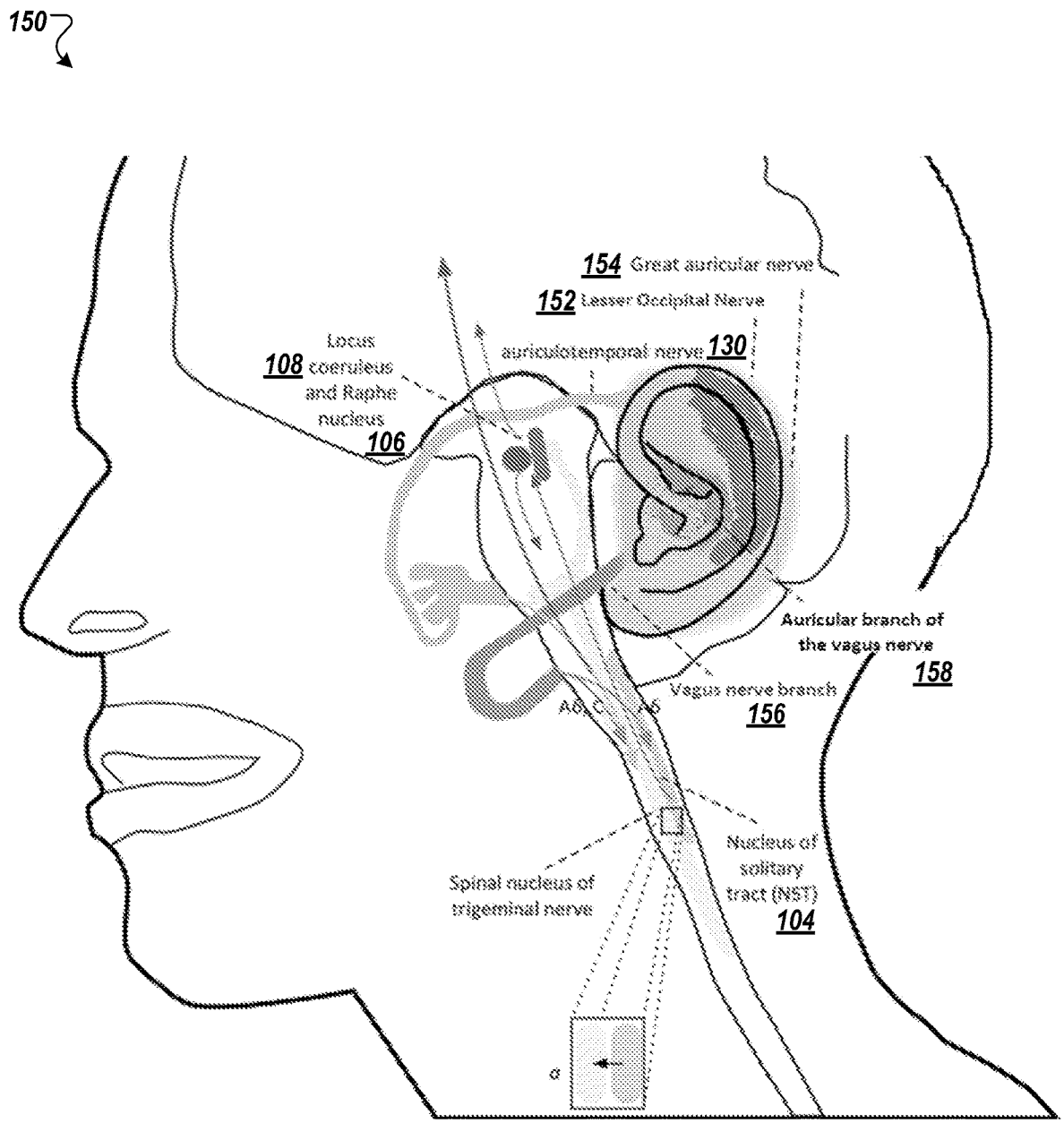

FIG. 1A and FIG. 1B illustrate example neural structures and pathways useful in embodiments disclosed herein for deriving benefits through nerve stimulation. Turning to FIG. 1A, the Nucleus Tractus Solitarius (NTS) 104 receives afferent connections from many areas including the Trigeminocervical Complex (TCC) 102, the cervical vagus nerve 128, as well as from the auricular branch of the vagus nerve (ABVN) 118. The TCC 102 is a region in the cervical spinal cord in which spinal cervical nerves from C1, C2, and C3 converge with sensory trigeminal fibers. In the region of the TCC 102, the trigeminal and occipital fibers synapse, including the Auriculotemporal Nerve 130, the lesser occipital nerve 152, and the greater auricular nerve 154 (e.g., Cervical Spinal 148). The TCC 102 projects to multiple areas in the brain stem including, but not limited to parts of the Raphe nuclei (hereafter Raphe Nucleus (RN) 106), the Locus Coeruleus (LC) 108, Periaqueductal Gray (PAG) 110, Nucleus Basalis (NBM) 120, the Nucleus Ambiguus (NA) 122, the Ventral Tegmental Area (VTA) 124, the Nucleus Accumbens (NAc) 126, Parabrachial nucleus (PbN) 114, and, as mentioned above, to the NTS. The NTS 104 among others, also projects to the RN 106 the LC 108, and the PAG 110 as well as to higher centers like the hypothalamus 132, including into the Arcuate Nucleus (ARC) 112 which receives its majority of non-intrahypothalamic afferents from the NTS 104. Cells in the ARC 112 are the main source of endorphins in the Central Nervous System (CNS).

The medulla oblongata (medulla) is the lower region of the brainstem containing important neuronal structures (nuclei) modulating, for example, several important involuntary actions such as respiration, heart rate, and blood pressure. The medulla contains several important nuclei (medullary nuclei) such as the NTS 104, the spinal trigeminal nucleus, the NA 122, and at least some of the RN 106. Additionally, many interconnections exist amongst different brainstem nuclei (e.g., PAG 110, LC 108, RN 106, NBM 120, PbN 114, Pedunculopontine Nucleus (PPN) 116, NA 122, VTA 124, NAc 126). For example, the LC 108, PAG 110, and RN 106 project to the NA 122, and the PPN 116 projects into the VTA 124. The VTA 124, in turn, projects to the Prefrontal Cortex 136, being interconnected with the hypothalamus 132 and the hippocampus 138. The VTA 124 projects directly to the Hippocampus 138 as well. The Hippocampus 138, in turn, projects to the NAc 126 and interconnects with the hypothalamus 132. The following table presents a listing of opioid receptors in the central nervous system:

TABLE 1

| Receptor | Expression/Distribution | Cell Types | Endogenous Ligands (affinity) |
|---|---|---|---|
| MOR | Amygdala 149, thalamus, periaqueductal gray 110, locus coeruleus 108, nucleus raphe magnus, mesencephalon, habenula, hippocampus 138, some brainstem nuclei | GABAergic Glutamatergic | β-endorphin (High) enkephalins (Med) Dynorphin (Low) |
| KOR | Basal anterior forebrain, olfactory tubercle, striatum (caudate putamen and NAc 126), preoptic area, hypothalamus 132, pituitary | Dopaminergic Glutamatergic GABAergic | Dynorphin (High) β-endorphin (Low) enkephalins (Low) |
| DOR | Olfactory tract, cortices, including whole neocortex and regions of the amygdala 149 that derive from the cortex (basolateral, cortical, and median nuclei of the amygdala 149), striatum | GABAergic Dopaminergic | β-endorphin (High) enkephalins (High) Dynorphin (Low) |
| NOP | Periaqueductal gray 110, thalamic nuclei, somatosensory cortex, rostral ventral medulla, spinal cord, dorsal root ganglia, VTA 124, NAc 126, PFC, central amygdala, lateral hypothalamus | Dopaminergic | Orphanin FQ/ nociceptin (High) |

MOR/KOR/DOR = μ/κ/δ-opioid receptor; NOP = nociception/orphanin FQ receptor; NAc = nucleus accumbens; PFC = prefrontal cortex; VTA = ventral tegmental area.
Affinity is presented in parenthesis.

These connections make this neural circuit extremely important for modulating pain, as production of endorphins, enkephalins, and dynorphins are modulated by this circuit. In addition, these neural circuits are crucial for learning and memory as well as for arousal and wakefulness. For example, an interaction between norepinephrine, produced by activity in the Locus Coeruleus (LC) 108, Serotonin (5-HT), produced by activity in the RN, and Acetylcholine (ACh) produced by activity in the Pedunculopontine Nucleus (PPN) 116 or NBM 120 is extremely important for memory and learning. Arousal and wakefulness are modulated, amongst others, by catecholamines in the brain, such as norepinephrine and dopamine.

There are descending indirect connections (e.g., via efferent pathways 139) going to the heart 140, lungs 142, gut 144, and spleen 146. Indirect connections include connections where there is at least one synapse elsewhere before reaching the target. This means that modulating the activity of these neural circuits can affect the respective organs. In particular, heart rate can be modulated (e.g., heart rate can be decreased and heart rate variability can be increased); oxygen absorption can be increased at the lungs 142 by increasing the compliance of the bronchi tissue and thus increasing the oxygen transport availability therefore increasing the potential for more oxygen to be absorbed into the blood; gut motility can be increased by descending pathways originating in the dorsal motor nucleus of the vagus nerve (DMV) 304 of FIG. 3B; since DMV activity is modulated by NTS activity, motility in the gut 144 can be affected by modulating the activity in the NTS 104; and a decrease in circulating pro-inflammatory cytokines can be achieved by modulating spleen 146 activity via NTS 104 descending pathways.

Turning to FIG. 1B, as shown in a block diagram 150, the vagus nerve 156 is a cranial nerve that which on its path can be located adjacent to the carotid artery in the neck. Direct stimulation of the vagus nerve 156 activates the nucleus tractus solitarius (NTS) 104, which has projections to nucleus basalis (NBM) 120 and locus coeruleus (LC) 108. The NBM 120 and LC 108 are deep brain structures that release acetylcholine and norepinephrine, respectively, which are pro-plasticity neurotransmitters important for learning and memory. Stimulation of the vagus nerve 156 using a chronically implanted electrode cuff is safely used in humans to treat epilepsy and depression and has shown success in clinical trials for tinnitus and motor impairments after stroke. The auricular branch of the vagus nerve 158 innervates the dermatome region of outer ear, being the region known as the cymba conchae one of the areas innervated by it. Non-invasive stimulation of the auricular branch of the vagus nerve 158 may drive activity in similar brain regions as invasive vagus nerve stimulation. Auricular neurostimulation has proven beneficial in treating a number of human disorders.

Figure 2B:
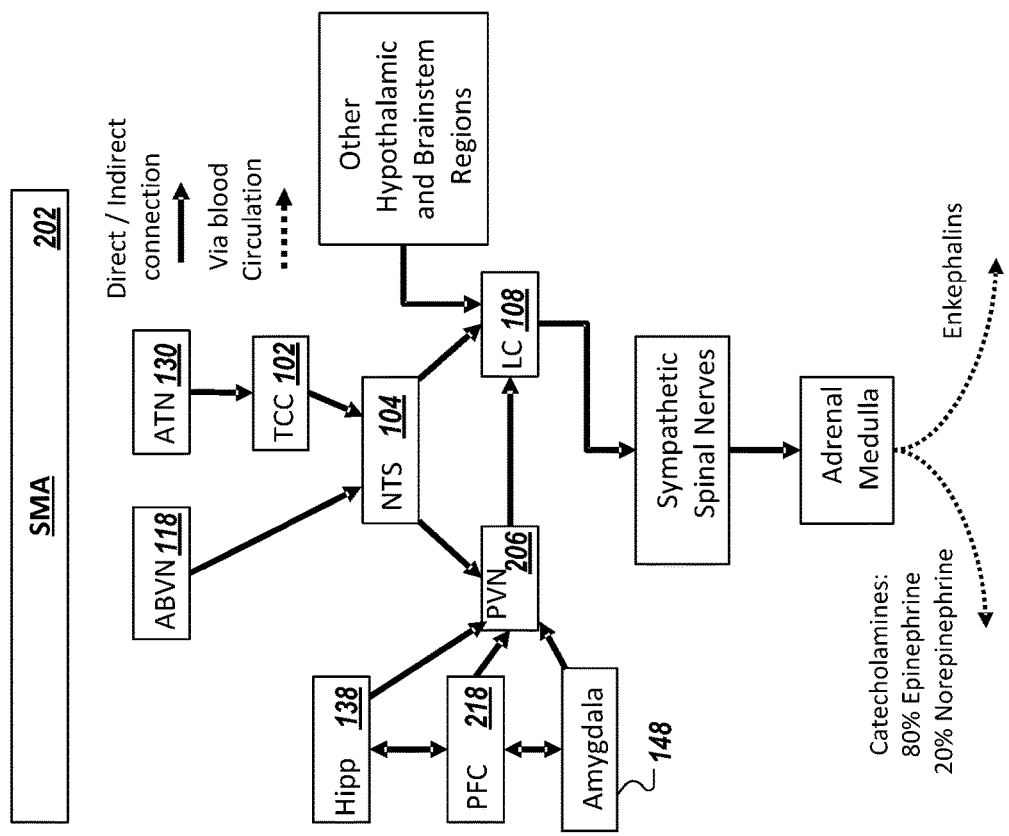
FIG. 2B illustrates example connections of the Sympathetic-Adrenomedullary (SMA) Axis pathway.
Figure 2A:
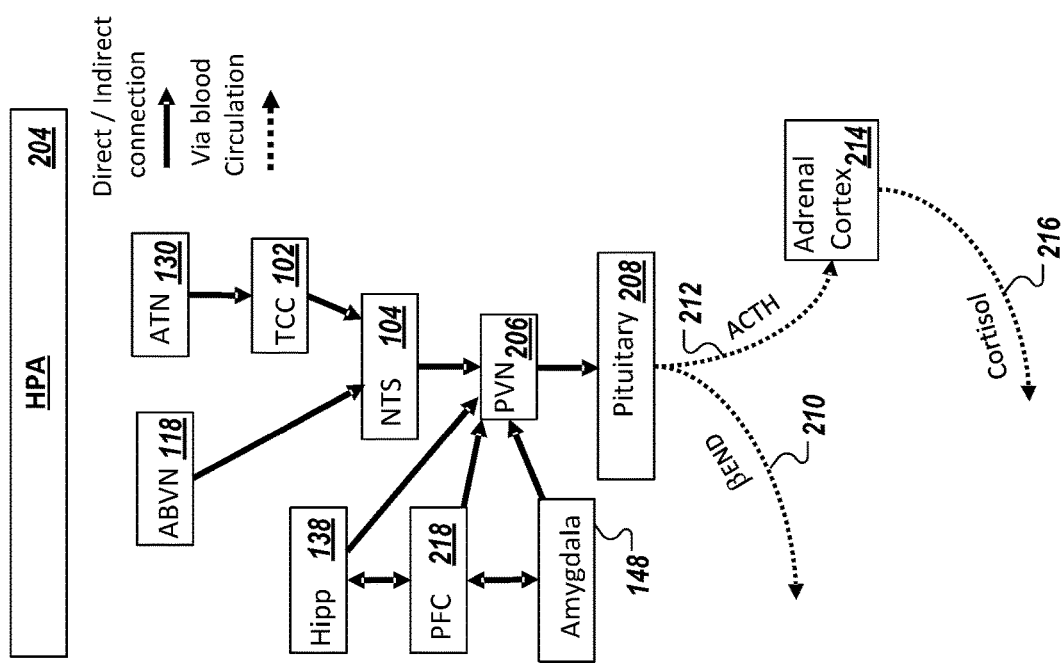
FIG. 2A illustrates example connections of the Hypothalamic-Pituitary-Adrenal (HPA) Axis pathway.

Turning to FIG. 2A and FIG. 2B, the response to a stressor, (i.e., the stress response) is carried out via two main pathways: the Sympathetic-Adrenomedullary (SMA) Axis 202 and the Hypothalamic-Pituitary-Adrenal (HPA) Axis 204. Although many brain regions or nuclei are involved in the stress response, the Locus Coeruleus (LC) 108 and the Paraventricular Hypothalamic Nucleus (PVN) 206 (PVN 113 of FIG. 1A) are the two main drivers of these pathways. Modulating central neural autonomic structures (CNAS) along either or both of these main pathways may produce a whole-body response by triggering or by modulating peripheral activity.

The LC 108 is the main producer of Norepinephrine (NE) in the Central Nervous System (CNS) and is one of the main drivers of the sympathetic nervous system (SNS). In response to a stressor, the LC 108 releases NE.

In responding to a stressor, the PVN 206 produces, amongst others, Corticotropin (also written as Corticotrophin) Releasing Hormone (CRH), also known as Corticotropin Releasing Factor (CRF). CRH is delivered to several brain nuclei, including the LC 108, as well as to the pituitary gland 208 which consequently releases, amongst others, β-endorphins 210 and adrenocorticotropic hormone (ACTH) 212 into the blood steam. The circulating ACTH 212 reaches the adrenal gland (adrenal cortex) 214 and triggers the release of Epinephrine (Epi), NE, and glucocorticoids into the blood stream, in particular cortisol 216 in humans. In general, the Epi/NE ratio released by the adrenals is 80/20.

Epi and NE primarily elicit a sympathetic response (e.g., increase heart rate). Cortisol 216 has various physiologic effects, including catecholamine release (e.g., Epi, NE, etc.), suppression of insulin, mobilization of energy stores through gluconeogenesis and glycogenolysis, as well as the suppression of the immune-inflammatory response. In addition, cortisol 216 serves as a feedback molecule-signal to limit the further release of CRH, thus slowing down the stress response.

The β-endorphins 210 released from the pituitary gland 208 bind opioid receptors primarily in the peripheral nervous system (but also to immune cells), where, amongst other effects, they produce analgesia. This analgesia is the result of a cascade of interactions resulting in inhibition of the release of tachykinins, particularly of substance P, which is involved in the transmission of pain.

The PVN 206 receives stress-related ascending monosynaptic afferent signals from several areas/nuclei. These nuclei include the Nucleus of the Solitary Track (NTS) 104, the LC 108, the parabrachial nuclei (PbN) 114, the Periaqueductal Grey Area (PAG) 110, and the Raphe Nucleus (RN) 106. These ascending pathways carry information regarding the stressor or stressors encountered. In addition to these ascending afferent signals, intrahypothalamic as well as descending afferent signals modulate the PVN 206 response to stressors. For example, signals from the Prefrontal cortex (PFC) 218, the Hippocampus (Hipp) 138, and the Amygdala 149 reach the PVN 206; in some cases, these signals are further integrated at the Bed Nucleus of the Stria Terminalis (BNST) before reaching the PVN 206. Together, these signals incorporate cognitive and memory information into the stress response.

Figure 3B:
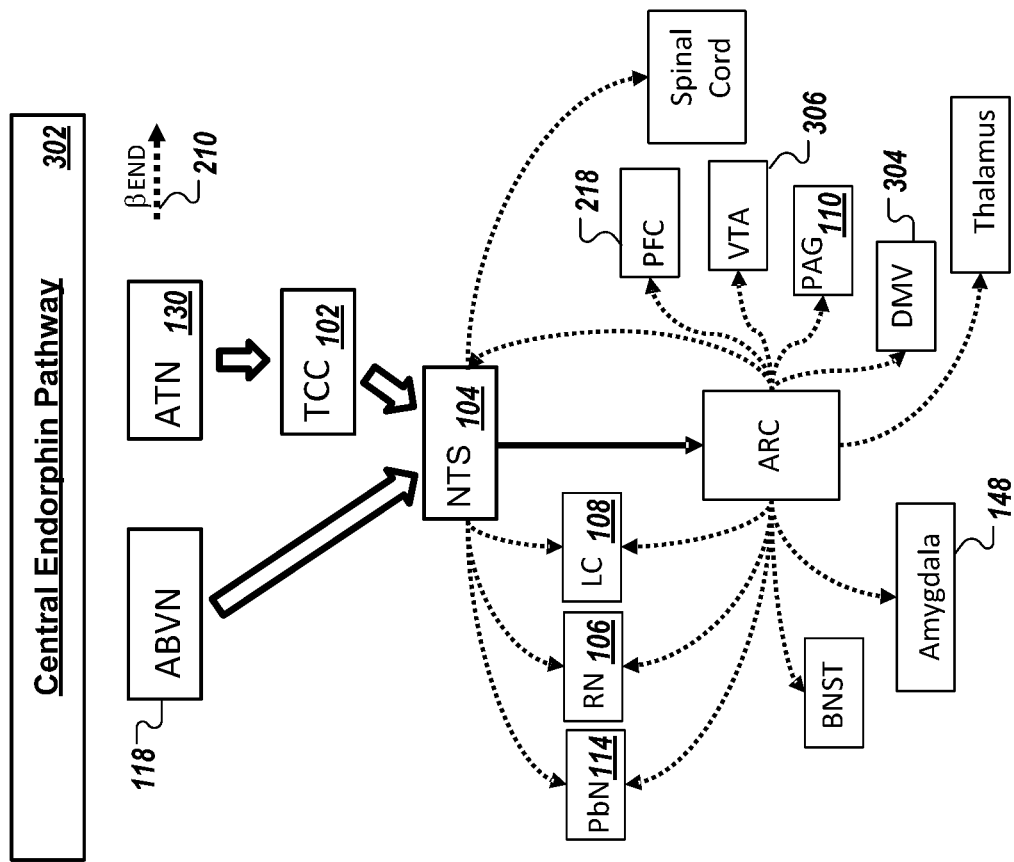
FIG. 3B illustrates example connections of the central endorphin pathway.
Figure 3A:
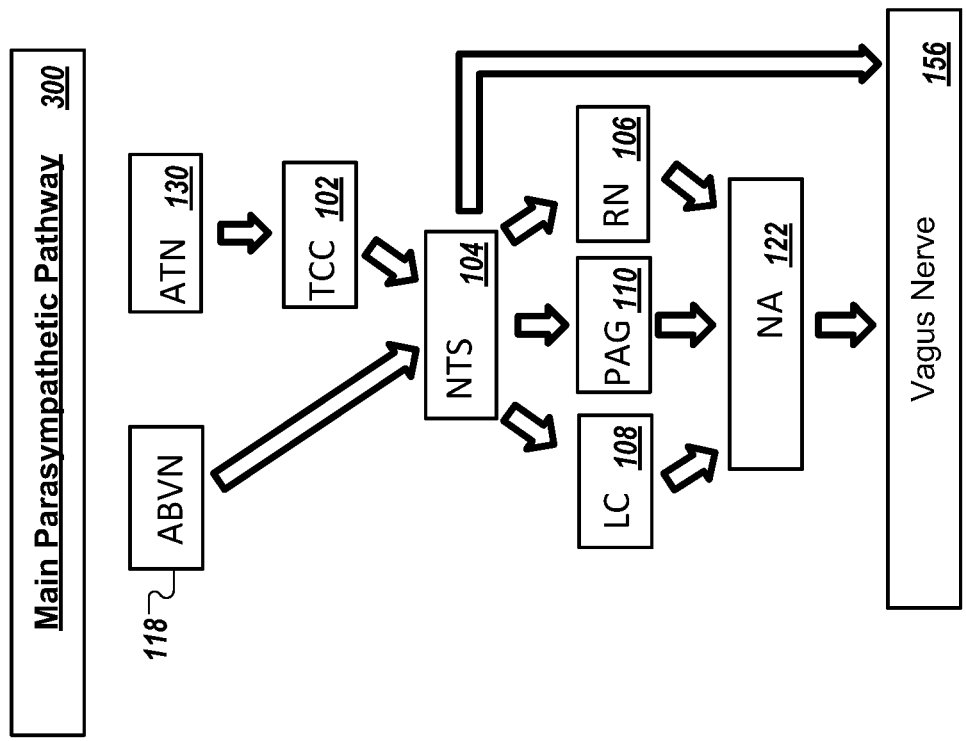
FIG. 3A illustrates example connections of the main parasympathetic pathway.

Turning to FIG. 3A and FIG. 3B, psychological stressors are perceived and interpreted in an anticipatory fashion, and the response can be heavily modulated by the reward circuit, which includes the PFC 218, the Amygdala 149, the Ventral Tegmental Area (VTA) 306, as well as the Nucleus Accumbens (NAc) 126 (dopaminergic pathways, which are highly modulated by the central endorphin pathway 302). Under normal circumstances, the Pre-Limbic (PL) and Infra-Limbic (IL) areas of the PFC 218 coordinate a top-bottom control over the stress response to psychological stressors. However, under high stress levels or chronic stress scenarios this top-bottom control gets disrupted and a bottom-top control, heavily weighing the Amygdala's inputs, takes over the stress response to these psychological stressors. Having a bottom-top type response hinders the decision-making processes by not given proper weight to other signals; for example, to those afferent signals from the PFC 218 and the hippocampus 138.

The brain areas or nuclei forming the neural circuitry involved in the stress response are not only involved in depression but also are integral components of the Endogenous Opioid Circuit (EOC), which includes the Central Endorphin Pathway (FIG. 3B) as well as the secondary connections arising from it. As illustrated in FIG. 3B, together with FIGS. 2A and 2B, the NTS 104, LC 108, PbN 114, PAG 110, RN 106, PFC 218, VTA 306, NAc 126 (as it receives afferents from the VTA 306), the Amygdala 149 are part of the EOC. The central endorphin pathway 302 interacts with several other brain regions or nuclei including with other hypothalamic areas such as the PVN 206. Stimulating afferent pathways to the central endorphin pathway 302 such as vagal and/or trigeminal structures activates this circuit and connected regions, including the VTA 306, which is one of the main producers of dopamine in the CNS. By activating the central endorphin pathway 302 and connected regions, systems and methods described herein are able to modulate stress and alertness levels.

As stated before, one of the characteristics of stress is a hyperactive SNS, a hypoactive parasympathetic nervous system (PNS), or both; resulting in a high SNS/PNS activity ratio. An increase in the activity of the PNS leads to a faster return to baseline after a response to a stressor. One way to increase PNS activity is to increase vagal tone which can be achieved by increasing the activity of the Vagus nerve 156. Activation of The Main Parasympathetic Pathway 300 of FIG. 3A results in an increase in vagal tone and thus a better stress response. Amongst the main vagus nerve afferent pathways are those originating in the NTS 104, the NA 122, and the DMV 304. Activity in these regions generally results in an increase in vagal tone. Activation of the ABVN 118 and the auriculotemporal nerve (ATN) 130 directly and indirectly lead to increase activity in all three above mentioned pathways going from the NTS 104, the DMV 304, and the NA 122, to the Vagus nerve 156. As seen in FIG. 3A these pathways also involve other nuclei or regions such as LC 108, PAG 110, RN 106, and TCC 102.

Figures 4A, 4B:
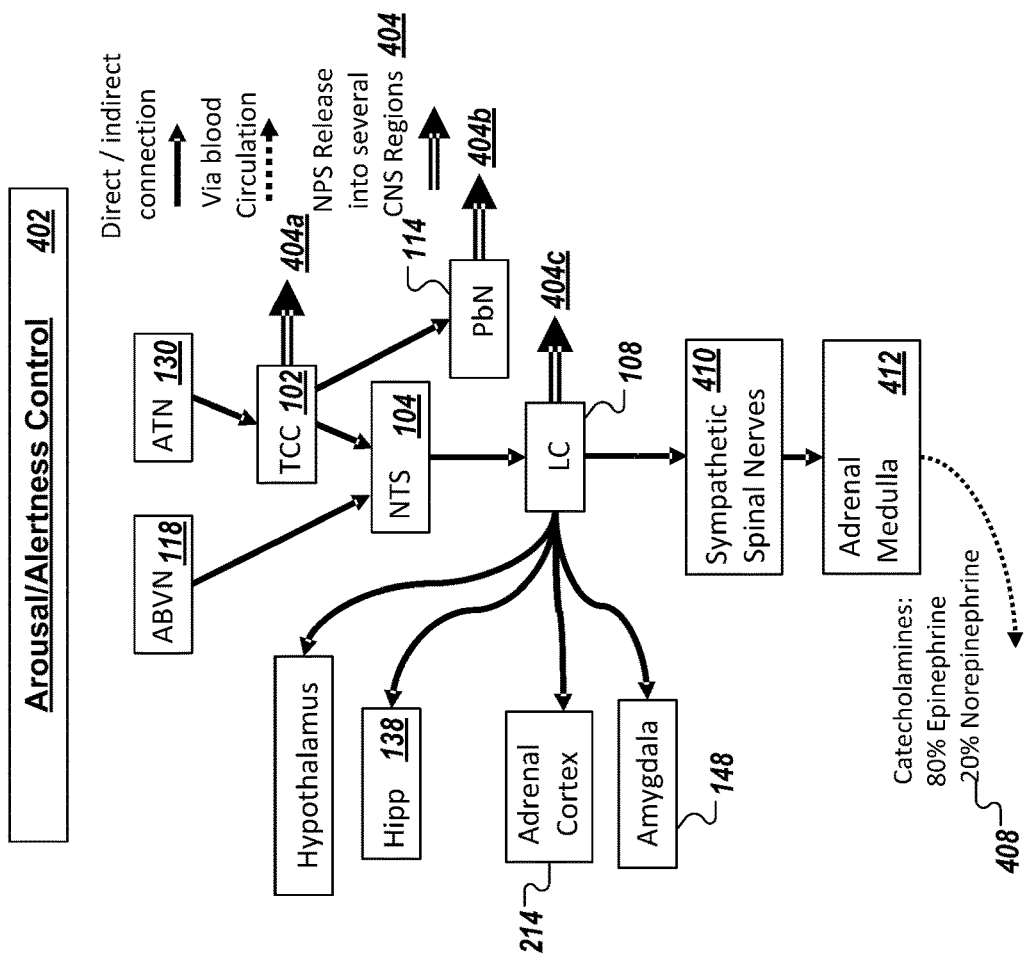
FIG. 4A illustrates example connections of a stress reduction pathway.
FIG. 4B illustrates example connections of an arousal and alertness control pathway.

As can be seen from a comparison of the stress reduction pathway 400 of FIG. 4A with the main parasympathetic pathway 300 of FIG. 3A and the central endorphin pathway 302 of FIG. 3B, significant overlap exists. Turning to the stress reduction pathway 400 and arousal/alertness control pathway 402, stimulation (e.g., of the ABVN 118 and/or ATN 130) can be provided to trigger Neuropeptide S (NPS) release into several CNS regions 404. In the CNS, NE is primarily produced in the LC 108. NPS is produced in the LC 108, the trigeminal nucleus, and the Parabrachial Nucleus (PbN) 114. Neuropeptides as opposed to neurotransmitters require a higher level of activity to be released (e.g., higher frequency of neuronal activity at the production sites). The NPS release 404, for example, includes release via the TCC 102, the PbN 114, and the LC 108.

LC 108 activity is key for arousal. Both Norepinephrine 408 and NPS, which are produced in and around the LC 108, promote arousal and wakefulness. Thus, turning to FIG. 4B, interventions that increase NE and NPS in the CNS 404 also increase arousal, mitigating the effects of fatigue.

Descending pathways from the LC 108 directly activate sympathetic preganglionic neurons in the spinal cord (e.g., Coeruleo-Spinal Pathway). Activation of these sympathetic spinal neurons has a net sympathetic effect, such as for example an increase in heart rate. Many of the generalized sympathetic effects are a direct effect of the higher amount of circulating catecholamines, in particular epinephrine and norepinephrine. The main source of these catecholamines is the adrenal medulla 412, which is innervated by preganglionic sympathetic nerves 410. The adrenal medulla 412 releases a mix of approximately 80% epinephrine and 20% norepinephrine 408 into the blood stream when stimulated.

Heart rate variability (HRV) is a reflection of the state of the autonomic nervous system (ANS). The sympathetic branch of the ANS, which is more active during stressful situations, tends to increase heart rate (HR) and decrease HRV; the opposite is true for the parasympathetic branch of the ANS, which tends to decrease HR and increase HRV. Higher HRV has been associated with well-being and has been used as a health biomarker.

Figure 4C:
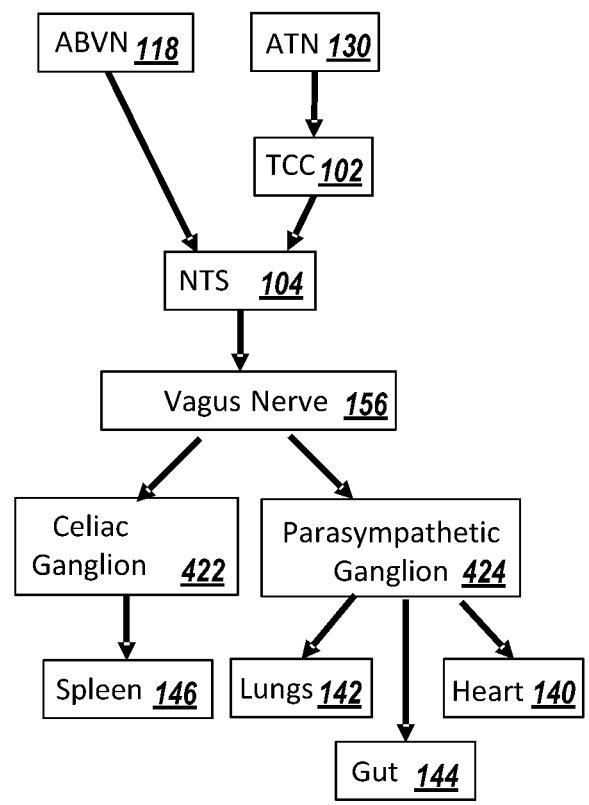
FIG. 4C illustrates example connections of an anti-inflammatory pathway.

In some implementations, an anti-inflammatory effect is provided via activation of an anti-inflammatory pathway 420 (e.g., the cholinergic anti-inflammatory pathway), as illustrated in FIG. 4C. In particular, the methods and devices described herein may activate the anti-inflammatory pathway by stimulating the ABVN 118 and/or the ATN 130 which, as stated before, have projections to the NTS 104. These projections elicit cholinergic anti-inflammatory effects via efferent pathways, mostly via the vagus nerve 156. Systemic anti-inflammatory effects occur when the vagus nerve 156 mediates spleen 146 function, thereby reducing the amount of circulating pro-inflammatory cytokines. In addition, a local anti-inflammatory effect occurs at organs reached by the efferent pathways, such as at the lungs 142, gut 144, and heart 140.

Decreasing systemic pro-inflammatory processes and/or pro-inflammatory processes in one or more target organs 140, 142, 144, and/or 146, in some implementations, involves modulating at least a portion of the anti-inflammatory pathway 420 such that activity at the NTS 104 is modulated affecting activity in efferent pathways through the celiac ganglion 422 and/or the parasympathetic ganglion 424, which in turn modulate activity in the spleen 146, lungs 142, gut 144, and/or heart 140 such that an anti-inflammatory response is elicited.

In some embodiments, the anti-inflammatory pathway 420 may be activated to reduce bleeding. For example, activation of a portion of the anti-inflammatory pathway 420, via stimulation of the vagus nerve 156, is discussed in U.S. Pat. No. 8,729,129 to Tracey et al., incorporated by reference herein in its entirety.

Figures 5A, 5B:
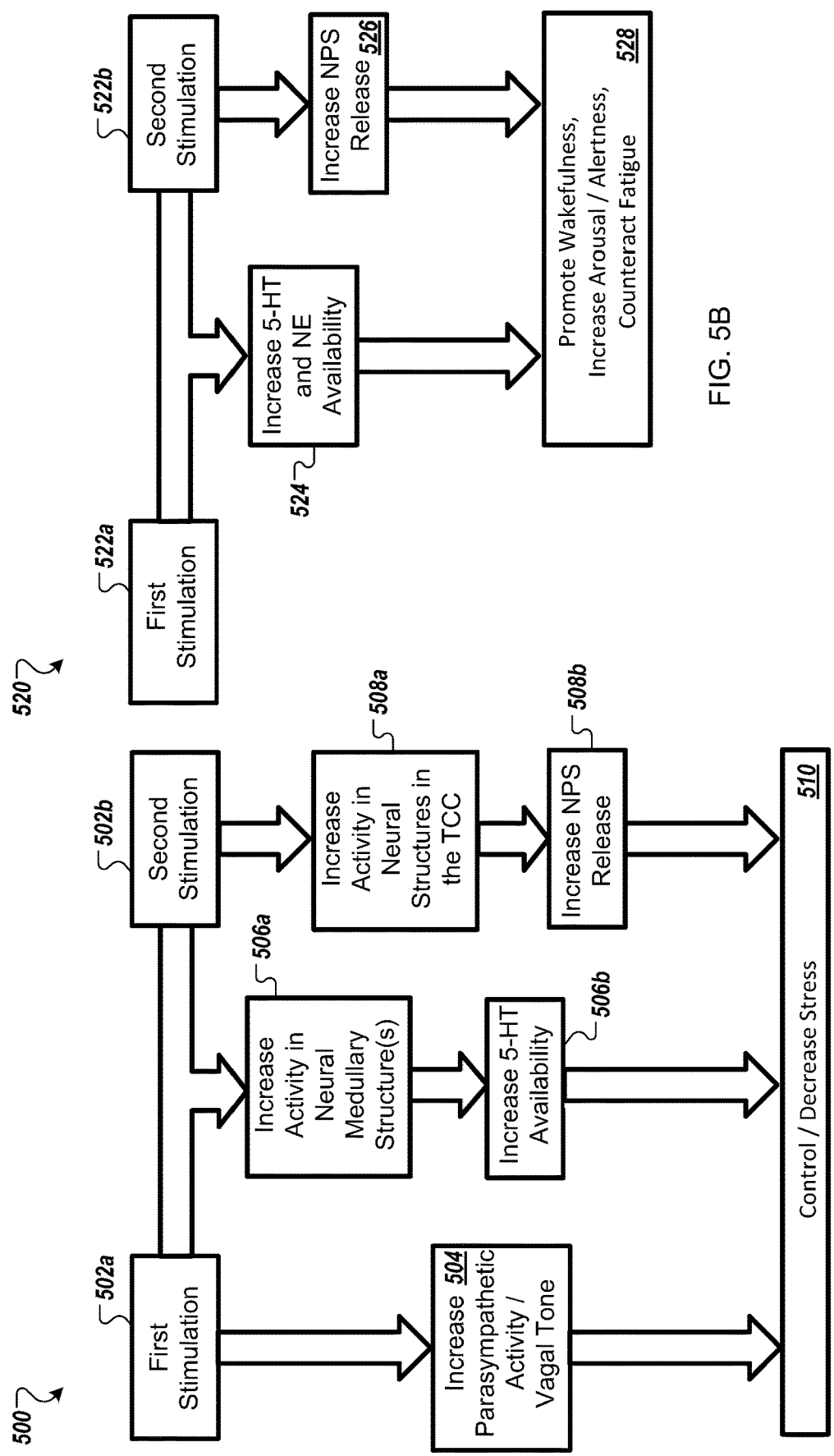
FIG. 5A illustrates example mechanisms for using electrical stimulation to control and/or decrease stress.
FIG. 5B illustrates example mechanisms for using electrical stimulation to promote wakefulness, increase arousal/alertness, and counteract fatigue.
Figure 8A:
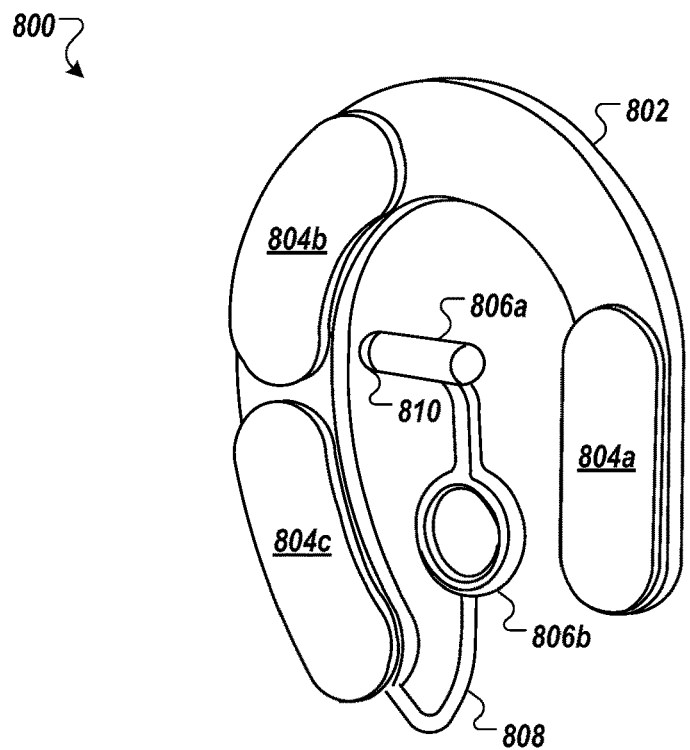
FIGS. 8A-8B illustrate a first example auricular therapeutic device.
Figure 9A:
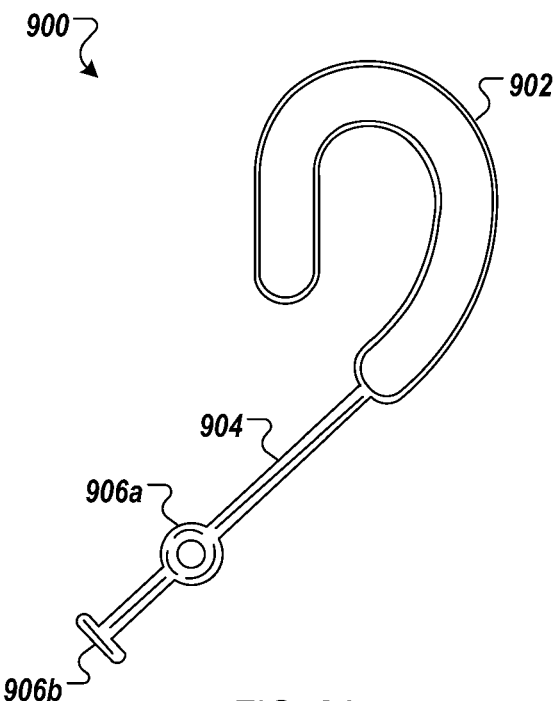
FIGS. 9A-9C illustrate a second example auricular therapeutic device.

Turning to FIG. 5A, a stimulation flow diagram 500 illustrates stimulation mechanisms for controlling and/or decreasing stress 510 using a treatment device such as a treatment device 800 of FIG. 8A or a treatment device 900 of FIG. 9A. The stimulation mechanisms are produced by a first stimulation 502*a* and a second stimulation 502*b*. The first and second stimulations, in some embodiments, are temporally separated (e.g., in overlapping or non-overlapping stimulations). In some embodiments, the first and second stimulations are physically separated (e.g., using a different electrode or set of electrodes contacting a different location on the patient). The first and second stimulations, for example, may be provided via the stress reduction pathways 400 discussed in relation to FIG. 4A. According to the pathways 400, the first stimulation 502*a* and/or the second stimulation 502*b* may be configured to stimulate the ABVN 118 which projects to the prefrontal cortex and/or the ATN 130 which has a pathway to the prefrontal cortex 136 via the TCC 102.

Responsive to a first stimulation 502*a*, in some embodiments, parasympathetic activity and/or vagal tone is increased (504). For example, Enkephalins may increase BDNF mRNA expression in the hippocampus mediated by DOR and MOR mechanisms while β-Endorphin, endomorphin-1 and endomorphin-2 upregulate BDNF mRNA in the prefrontal cortex, hippocampus and amygdala. Production of dopamine (DA) in the Ventral Tegmental Area (VTA) 124 can be augmented by an increase in MOR agonist (e.g., endorphins and enkephalins); in particular by inhibiting GABAergic interneurons which in turn inhibit dopaminergic neurons in the VTA. Amongst other, these DAergic VTA neurons project to Nucleus Accumbens (NAc) 126, the Prefrontal Cortex (PFC) 136, the Hippocampus (Hipp) 138, and the Amygdala (Amyg) 149. These brain regions also share projections/connections amongst themselves making an important neuronal circuit known as the Reward Circuit or Reward Neural Circuit. Alterations leading to dysregulation, maladaptive regulation, or dysfunctional interactions in this neural circuit are seen in people with behaviors such as addiction, anxiety disorders including PTSD, and depression. Furthermore, dysregulation in this circuit has also been observed in people showing behaviors associated with lower attention levels, for example in attention deficit disorder (ADD) and attention deficit hyper-activity deficit disorder (ADHD).

Further, in some implementations, the first stimulation 502*a* increases activity in one or more neural medullary structures 506*a*, such as the NTS 104, the spinal trigeminal nucleus, the NA 122, and at least some of the RN 106. The first stimulation 502*a*, for example, may increase availability 506*b*, leading to an increase in BDNF expression. The BDNF, in turn, may function to protect monoamine neurotransmitter neurons and assist the monoamine neurotransmitter neurons to differentiate. In some embodiments, the second stimulation 502*b* also increases 5-HT availability.

NPS is mainly produced in three areas in the brain: LC 108, PbN 404*b*, and the trigeminal nucleus, the latter being the target of the ATN 130 and at least partially included in the TCC 102. Activity in any of these three areas is necessary for NPS expression 404. In some implementations, the second stimulation 502*b* increases activity in neural structures in the TCC 508*a*. The second stimulation 502*b*, for example, may increase NPS release 508*b* via the activation cascade that follows the stimulation of the ATN 130.

In some embodiments, providing the first stimulation 502*a* and providing the second stimulation 502*b* involves providing a series of simultaneous and/or synchronized, and/or interleaved stimulation pulses. Each of the first stimulation 502*a* and the second stimulation 502*b* may be applied using the same or different parameters. The parameters, in some examples, may include pulse frequency (e.g., low, mid-range, high, or very high) and/or pulse width. Further, the parameters may indicate electrode pairs for producing biphasic pulses. In a first illustrative example, the first stimulation may be applied using a low frequency, while the second stimulation is applied using a mid-range or high frequency. Conversely, in a second illustrative example, the first stimulation may be applied using a mid-range frequency, while the second stimulation is applied using a low frequency. Other combinations of low, mid-range, high, and/or very high frequency stimulations are possible depending upon the patient and the disorder being treated. Therapy may be optimized according to the needs of individual patients including custom stimulation frequency, custom pulse width, custom stimulation intensity (amplitude), and/or independently controlled stimulation channels.

Turning to FIG. 5B, a stimulation flow diagram 520 illustrates stimulation mechanisms for promoting wakefulness and increasing arousal/alertness to counteract fatigue 528 using a treatment device such as a treatment device 800 of FIG. 8A or a treatment device 900 of FIG. 9A. The stimulation mechanisms are produced by a first stimulation 522*a* and a second stimulation 522*b*. The first and second stimulations, in some embodiments, are temporally separated (e.g., in overlapping or non-overlapping stimulations). In some embodiments, the first and second stimulations are physically separated (e.g., using a different electrode or set of electrodes contacting a different location on the patient). The first and second stimulations, for example, may be provided via the arousal alertness/control pathways 402 discussed in relation to FIG. 4B. According to the pathways 402, the first stimulation 522*a* and/or the second stimulation 522*b* may be configured to stimulate the ABVN 118 which projects to the prefrontal cortex and/or the ATN 130 which has a pathway to the prefrontal cortex via the TCC 102.

Responsive to a first stimulation 522*a*, in some embodiments, 5-HT and NE availability are increased (524), leading to an increase in BDNF expression. The BDNF, in turn, may function to protect monoamine neurotransmitter neurons and assist the monoamine neurotransmitter neurons to differentiate. In some embodiments, the second stimulation 522*b* also increases 5-HT and NE availability. NE and 5-HT are respectively produced in the Locus Coeruleus (LC) 108 and in the Raphe Nucleus (RN) 106. These brain regions are integral parts of the Endogenous Opioid Circuits (EOC). Activity in these brain regions (or brain areas) can be modulated by activating afferent pathways to the EOC such as some trigeminal and vagal branches.

Further demonstrating the previously mentioned link between the EOC, cognition, and depression, studies have shown that some antidepressants promote neurogenesis likely via the upregulation of Brain-Derived Neurotrophic-Factor (BDNF) in areas such as the hippocampus 138 and the prefrontal cortex (PFC) 136. BDNF plays a strong role in cognition, plasticity, neurogenesis, and neuronal survival. 5-HT has also been shown to have a role in such physiological activities. Furthermore, patients suffering from depression have been shown to have decreased plasma levels of BDNF, suggesting that depressive conditions would benefit from a therapy that could increase BDNF levels. Additionally, learning and memory as well as cortical plasticity is modulated by stimulation of vagal afferents through the synergetic action of ACh, 5-HT, NE, and BDNF. Further, acute vagal stimulation has been shown to increase NE and 5-HT release in the PFC 136 and the amygdala 149 as well as to enhance synaptic transmission in the hippocampus 138.

The cognitive improvement due to the increase in BDNF, which leads to a faster reorganization of neural circuits, can be leveraged not only to learn new things faster, but also to eliminate/extinguish undesirable and/or maladaptive behavior such as, in some examples, PTSD, phobias, and addictive behavior such as drug-seeking or overeating.

Also, it has been shown that vagal activation produces pairing-specific plasticity, thus stimulation of vagal afferents, irrespective of what neuromodulator is produced, can be used to eliminate and/or extinguish undesirable and/or maladaptive behavior such as those described above. Furthermore, trigeminal stimulation has been shown to help and protect cognitive function. Thus, as with vagal afferent activation, activation of trigeminal afferents can be utilized to conserve and promote cognitive performance.

In another example, the cognitive enhancement provided by the systems and methods described herein can be used to overcome the cognitive problems that have been described to occur in people exposed to microgravity environments such as astronauts in the space station or on a long space travel such as visiting Mars.

Additionally, BDNF levels have been shown to have an inverse correlation with factors associated with cognitive decline and/or impediments, such as in Alzheimer's patients.

The second stimulation 522*b*, in some embodiments, increases NPS release 526. As discussed above, this increase in NPS production or expression is the result of the activation cascade that follows the stimulation of the ATN 130.

In some embodiments, providing the first stimulation 522*a* and providing the second stimulation 522*b* involves providing a series of simultaneous and/or synchronized and/or interleaved stimulation pulses. Each of the first stimulation 522*a* and the second stimulation 522*b* may be applied using the same or different parameters. The parameters, in some examples, may include pulse frequency (e.g., low, mid-range, or high) and/or pulse width. Further, the parameters may indicate electrode pairs for producing biphasic pulses. In a first illustrative example, the first stimulation may be applied using a low frequency, while the second stimulation is applied using a mid-range or high frequency. Conversely, in a second illustrative example, the first stimulation may be applied using a mid-range frequency, while the second stimulation is applied using a low frequency. Other combinations of low, mid-range, high, and/or very high frequency stimulations are possible depending upon the disorder being treated. Therapy may be optimized according to the needs of individual patients including custom stimulation frequency, custom pulse width, custom stimulation intensity (amplitude), and/or independently controlled stimulation channels.

Figure 5C:
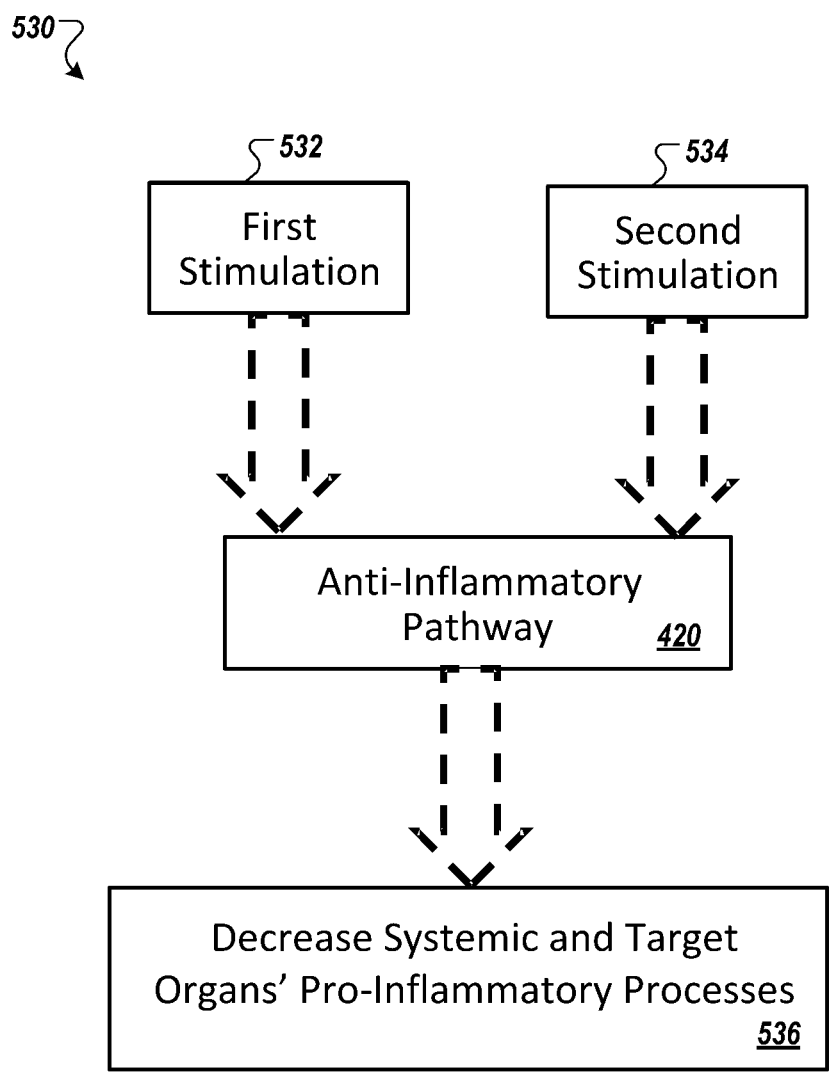
FIG. 5C illustrates example mechanisms for using electrical stimulation to for decrease pro-inflammatory processes.

Turning to FIG. 5C, a stimulation flow diagram 530 is illustrated for providing therapy to decrease systemic pro-inflammatory processes and/or pro-inflammatory processes in one or more target organs. The target organs, for example, may include the spleen, lungs, gut, and heart. The stimulations of flow diagram 530, in some examples, may be applied in mitigating bleeding, reducing volume of bleeding, and/or reducing a time period of blood loss. The stimulations of flow diagram 530, for example, may be performed at least in part by a pulse generator.

In some implementations, a first stimulation 532 is provided at a first tissue location configured to stimulate the anti-inflammatory pathway 420 for decreasing systemic pro-inflammatory processes and/or pro-inflammatory processes in one or more target organs 536. The pathways, for example, may include a portion of the pathways illustrated in FIG. 4C. The first tissue location, for example, may include a surface of an ear structure contacted by an in-ear component of an auricular stimulation device. In some embodiments, the first stimulation 532 is supplied to multiple tissue locations. For example, the first stimulation 532 may be applied to a first tissue location including a surface of an ear structure contacted by an in-ear component of an auricular stimulation device as well as to a second tissue location on the tragus of the ear.

Decreasing systemic pro-inflammatory processes and/or pro-inflammatory processes in one or more target organs 536, in some implementations, involves modulating at least a portion of the anti-inflammatory pathway of FIG. 4C such that activity at the NTS 104 is modulated affecting activity in efferent pathways through the celiac ganglion 422 and/or the parasympathetic ganglion 424, which in turn modulate activity in the spleen 146, lungs 142, gut 144, and/or heart 140 such that an anti-inflammatory response is elicited.

In some implementations, a second stimulation 534 is provided at a second tissue location configured to stimulate the anti-inflammatory pathway 420 for decreasing systemic pro-inflammatory processes and/or pro-inflammatory processes in one or more target organs 536. Examples of target pathways and structures for stimulation of the second tissue location include those modulating activity at and/or on the auriculotemporal nerve (ATN) 130, the lesser occipital nerve 152, and/or the great auricular nerve 154. The pathways, for example, may include a portion of the pathways illustrated in FIG. 5C.

In some embodiments, providing the first stimulation 532 and providing the second stimulation 534 involves providing a series of simultaneous and/or synchronized, and/or interleaved stimulation pulses to both the first tissue location and the second tissue location. Each of the first stimulation 532 and the second stimulation 534 may be applied using the same or different parameters. The parameters, in some examples, may include pulse frequency (e.g., low, mid-range, or high) or pulse width. Further, the parameters may indicate electrode pairs for producing biphasic pulses. In a first illustrative example, the first stimulation may be applied using a low frequency, while the second stimulation is applied using a mid-range or high frequency. Conversely, in a second illustrative example, the first stimulation may be applied using a mid-range frequency, while the second stimulation is applied using a low frequency. Other combinations of low, mid-range, high, and/or very high frequency stimulations are possible depending upon the patient and the disorder being treated.

In other embodiments, the therapy provided by the stimulation 532 and/or the stimulation 534 of the stimulation flow diagram 530 includes automatically adjusting delivery of the therapy (e.g., adjusting one or more parameters) based on feedback received from the pulse generator or another computing device in communication with the pulse generator. The feedback, in some examples, may include a blood oxygen concentration, a breathing rate, a breathing variation, tidal volume, skin conductance, blood pressure, heart rate, heart rate variability, pupillometry, and/or EEG signal.

In further embodiments, combinations of the stimulations described in stimulation flow diagrams 500 and/or 520 with the stimulations described in stimulation flow diagram 530 may be used to enhance stress reduction through reducing the time and/or volume of the physical stressor of bleeding. Thus, activation of the anti-inflammatory pathway 420 in combination with activation of the stress reduction pathway 400 of FIG. 4A may mitigate stress reactions in subjects experiencing physical stress at least partially induced by bleeding. In a further example, in subjects performing stressful activities that have a substantial likelihood of resulting in bleeding (e.g., certain athletes, military personnel involved in active missions, etc.), activating the anti-inflammatory pathway 420 prior to initiation of bleeding may decrease or minimize bleeding if it occurs and may be used in combination with activation of the arousal/alertness control pathway 402 to improve performance, reduce tunnel vision, and maintain focus of the subject during the activity.

For example, the first stimulation 532 of the stimulation flow diagram 530 may be delivered synchronously, simultaneously or interleaved with the second stimulation 502b of the stimulation flow diagram 500 of FIG. 5A for controlling and/or decreasing stress 510 or vice-versa. Similarly, for example, the first stimulation 532 of the stimulation flow diagram 530 may be delivered synchronously, simultaneously, or interleaved with the second stimulation 522b of the stimulation flow diagram 520 of FIG. 5B for promoting wakefulness, increasing arousal/alertness, and counteracting fatigue 528 or vice-versa. In another example, the therapy of the stimulation flow diagram 500, including both the first stimulation 502a and the second stimulation 502b may be delivered for a first period of time, and the therapy of the stimulation flow diagram 530, including both the first stimulation 532 and the second stimulation 534 may be delivered for a second period of time; or the therapy of the stimulation flow diagram 520, including both the first stimulation 522a and the second stimulation 522b may be delivered for a first period of time, and the therapy of the stimulation flow diagram 530, including both the first stimulation 532 and the second stimulation 534 may be delivered for a second period of time. The combined therapies, in some embodiments, may be repeated for a number of cycles of the first period of time and the second period of time. Based on feedback, the length of one or both of the first period of time and the second period of time may be adjusted to control/decrease stress 510 or promote wakefulness, increase arousal/alertness, and counteract fatigue 528 while decreasing systemic pro-inflammatory processes and/or pro-inflammatory processes in one or more target organs 536 in an efficient manner.

Figure 6A:
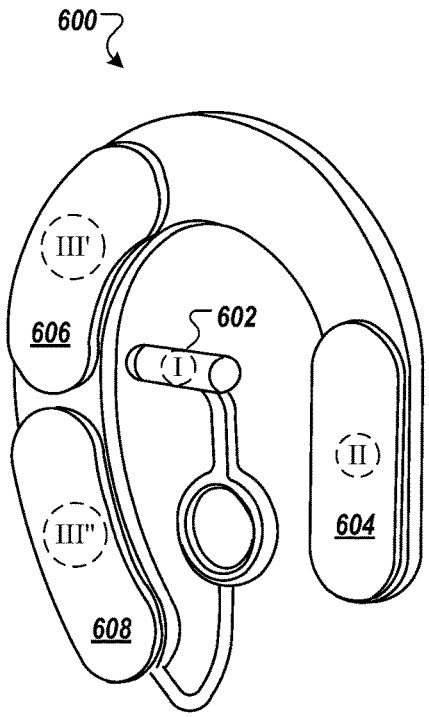
FIG. 6A and FIG. 6B illustrate an example electrode configuration and equivalent circuits for providing therapy.
Figure 6B:
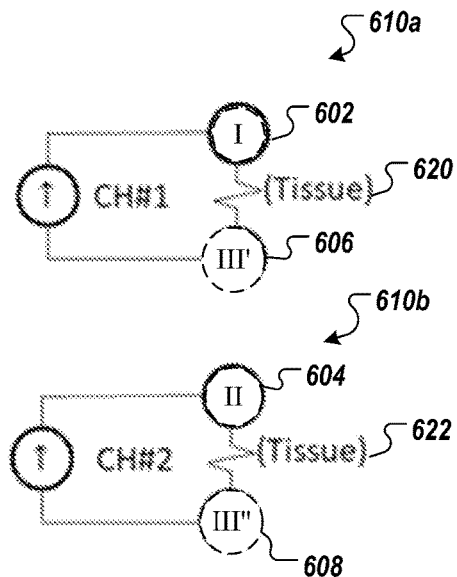

Turning to FIG. 6A and FIG. 6B, an example electrode configuration of an earpiece device 600 and example equivalent circuits 610a-b for providing therapy are shown. Turning to FIG. 6A, the earpiece device 600, in some implementations, includes inner ear component electrode 602, and auricular component electrodes 604, 606, and 608. Circuitry connecting between the electrodes 602, 604, 606, and 608 may be configured to form corresponding circuits 610a and 610b, as illustrated in FIG. 6B.

Turning to FIG. 6B, an equivalent circuit 610a is formed by electrode 602 and electrode 606 which are configured to stimulate tissue portions 620. In some implementations, the inner ear component electrode 602 is configured to contact a tissue portion 620 in the cymba conchae region which is enervated by branches of the auricular branch of the vagus nerve. The auricular component electrode 606, in some implementations, is configured to contact a tissue portion 620 in the region behind the ear which is enervated by branches of the great auricular nerve and/or branches of the lesser occipital nerve.

An equivalent circuit 610b is formed by electrode 604 and electrode 608 of the auricular component of the device 600 and configured to stimulate tissue portions 622. In some implementations, the tissue portions 622 are in the region rostral to the ear which is enervated by the auriculotemporal nerve as well as the region behind the ear which is enervated by branches of the great auricular nerve and branches of the lesser occipital nerve.

In further implementations, the tissue portions include the concha which may be stimulated, for example, at approximately 5 Hz or at approximately 15 Hz, or at approximately 30 Hz In other implementations, the tissue portions include tissue enervated by the trigeminal nerve which may be stimulated, for example, at approximately 100 Hz.

Figure 7:
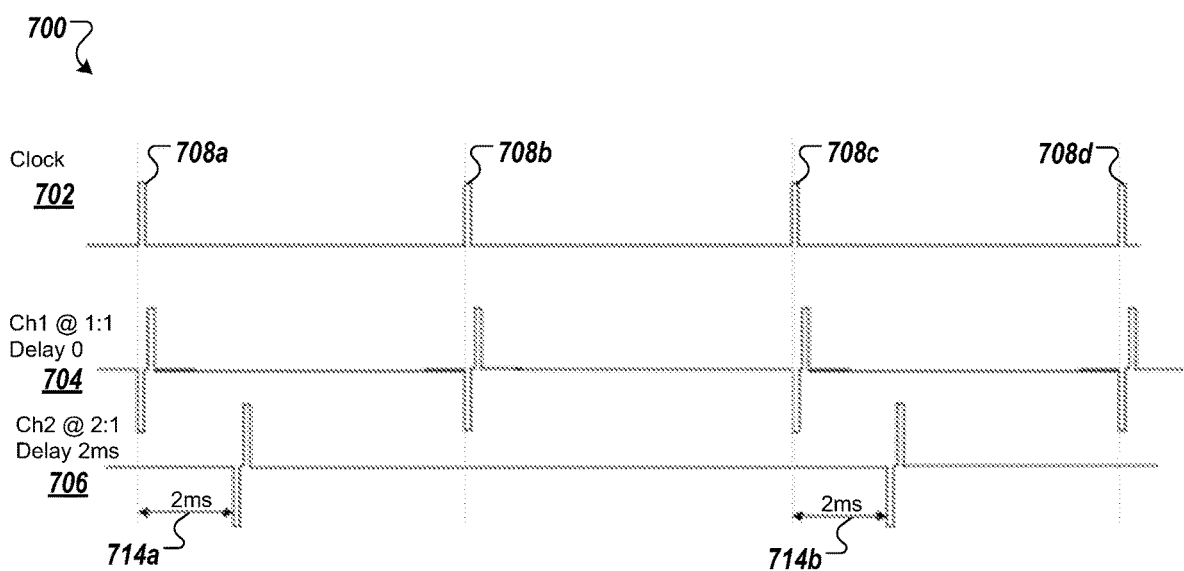
FIG. 7 illustrates an example timing diagram for supplying stimulation pulses a an auricular therapeutic device.

In some embodiments, the equivalent circuit 1210a is stimulated by a first channel and equivalent circuit 1210b is stimulated by a second channel. FIG. 7 pictures a timing diagram 700 illustrating the triggering of multiple channels 704 and 706 using a master clock 702 according to an example. In some embodiments, the clock 702 triggers pulses 708 at a predetermined clock frequency. In an example, a first channel 704 can be configured to trigger stimulation of equivalent circuit 610a and a second channel 706 can be configured to trigger stimulation of equivalent circuit 610b of FIG. 6B. Conversely, the triggering can be reversed, for example, where equivalent circuit 610b is triggered before equivalent circuit 610a.

In some implementations, stimulation is configured to be triggered by every pulse of the master clock 702; i.e., at a 1-to-1 ratio. In some embodiments, stimulation by one channel 704, 706 is configured to be triggered following a specific time interval after the pulse triggered by the other channel 704, 706 ends. In some embodiments, one of the channels 704, 706 is configured to be triggered based on every other pulse of the master clock; i.e., at a 2-to-1 ratio with the master clock. For example, the triggering by the second channel 706, as shown occurs every other clock cycle and after a specific time delay 714 from the master clock pulse 708. In other embodiments, stimulation by the second channel 706 may be configured to be triggered following a specific time interval after the pulse triggered by the first channel 704 ends. In some embodiments, stimulation from one channel 704, 706 is offset from stimulation by the other channel 704, 706 by a synchronous delay. As illustrated, the synchronous delay 714 is 2 ms and can be as little as zero (making both channels to trigger simultaneously depending on the master clock ratio for each channel) and as much as the master clock period less the combined duration of the stimulations provided by channel 704 and 706 plus the time interval between them. In some embodiments, this delay can be about 10 ms.

In some implementations, the equivalent circuits 610a, 610b are synchronized using a master clock counter and a register per channel. By setting each register to a number of master clock pulses to trigger the respective channel, each channel may be configured to be triggered when the channel register value equals the master clock pulses. Subsequently, the counter for each channel may be reset after the channel is triggered. In an example, using a 6-bit counter and a 6-bit register, the trigger frequency can be as high as the master clock frequency (1:1) and as low as 1/64 of the clock frequency (64:1).

In some embodiments in which stimulation is applied at more than one site (e.g., directed to two or more nerve branches, etc.) the stimulation duration, the frequency, the pulse width, and/or the duty cycle may differ across stimulation sites. In some embodiments, in fact, it is beneficial to use different frequencies at different stimulation sites.

Stimulation delivery may vary based upon the therapy provided by the treatment device. Frequency and/or pulse width parameters, for example, may be adjusted for one or more stimulation sites at which stimulation is being delivered.

In some embodiments, frequency and/or pulse width parameters are adjusted during therapy, for example responsive to feedback received from monitoring the patient. For example, feedback may be obtained using one or more sensors or other devices assessing heart rate, blood pressure, blood oxygen concentration, skin impedance, Electromyography (EMG), pupillometry, and/or motion.

In some embodiments, stimulation pulses are delivered in pulse patterns. Individual pulses in the pattern may vary in frequency and/or pulse width. Patterns may be repeated in stimulation cycles. The pulse pattern, for example, may be designed in part to ramp up stimulation, establishing a comfort level in the wearer to the feel of the stimulation. In another example, the pulse pattern may be designed in part to alternate stimulation between stimulation sites where two or more sites are being stimulated during therapy. In examples involving multiple stimulation sites, the stimulation pattern may be designed such that stimulating frequencies are not the same in all sites at which stimulation is being delivered.

In some embodiments involving electrical stimulation utilizing either percutaneous or transcutaneous (i.e., non-penetrating) electrodes, the stimulation frequencies vary within a set of ranges. For example, the stimulation frequencies applied in a stimulation pattern may include a first or low frequency within a range of about 1 to 30 Hz, a second or mid-range frequency within a range of about 30 to 70 Hz, a third or high frequency within a range of about 70 to 150 Hz; and/or a fourth or very high frequency within a range of about 150 to 300 Hz.

TABLE 2

Electrical therapy: Frequency Table
Electrical therapy: Frequency Table

| Frequency designation | Range in Hz |
|---|---|
| Low frequency | 1-30 |
| Mid-range frequency | 31-70 |
| High frequency | 71-150 |
| Very high frequency | 151-300 |

In one embodiment, a stimulation frequency is varied between 2 Hz and 100 Hz, in yet another embodiment, the pulse width can be adjusted from between 20 and 1000 microseconds to further allow therapy customization. Stimulation frequency is an important differentiator between neural networks; for example, using a high frequency has been shown to be beneficial in activating the desired trigeminal system features; in contrast, a low frequency is preferred in activating the desired vagal features. Thus, in a preferred embodiment, a combination of low frequency and high frequency is applied respectively to activate vagal and trigeminal branches in accordance with various embodiments described herein. In yet another embodiment, a variable frequency (e.g., stimulating at a non-constant frequency) can be used at one or more of the electrodes. The variable frequency can be a sweep, and/or a random/pseudo-random frequency variability around a central frequency (e.g., 5 Hz+/−1.5 Hz, or 100 Hz+/−10 Hz). Varying the stimulation frequency in a random or pseudo-random way can help to prevent neural accommodation.

When using electrical stimulation, different combinations of pulse widths can be used at each electrode. Pulse widths, in some examples, may range from one or more of the following: first or short pulse widths within a range of about 10 to 50 microseconds, or more particularly between 10 to 20 microseconds, 20 to 30 microseconds, 30 to 40 microseconds, to 50 microseconds; second or low mid-range pulse widths within a range of about 50 to 250 microseconds, or more particularly between 50 to 70 microseconds, 70 to 90 microseconds, 90 to 110 microseconds, 110 to 130 microseconds, 130 to 150 microseconds, 150 to 170 microseconds, 170 to 190 microseconds, 190 to 210 microseconds, 210 to 230 microseconds, or 230 to 250 microseconds; third or high mid-range pulse widths within a range of about 250 to 550 microseconds, or more particularly between 250 to 270 microseconds, 270 to 290 microseconds, 290 to 310 microseconds, 310 to 330 microseconds, 330 to 350 microseconds, 350 to 370 microseconds, 370 to 390 microseconds, 390 to 410 microseconds, 410 to 430 microseconds, 430 to 450 microseconds, 450 to 470 microseconds, 470 to 490 microseconds, 490 to 510 microseconds, 510 to 530 microseconds, or 530 to 550 microseconds; fourth or long pulse widths within a range of about 550 to 1000 microseconds, or more particularly between 550 to 600 microseconds, 600 to 650 microseconds, 650 to 700 microseconds, 700 to 750 microseconds, 750 to 800 microseconds, 800 to 850 microseconds, 850 to 900 microseconds, 900 to 950 microseconds, or 950 to 1000 microseconds; and/or a fifth or very long pulse widths within a range of about 1000 to 4000 microseconds or more particularly between 1000 to 1250 microseconds, 1250 to 1500 microseconds, 1500 to 1750 microseconds, 1750 to 2000 microseconds, 2000 to 2250 microseconds, 2250 to 2500 microseconds, 2500 to 2750 microseconds, 2750 to 3000 microseconds, 3000 to 3250 microseconds, 3250 to 3500 microseconds, 3500 to 3750 microseconds, 3750 to 4000 microseconds. Different embodiments can use different ranges of pulse widths at one or more of the electrodes. The selection of the stimulation pulse width depends on the desired target fiber as well as the output intensity. For example, given a similar intensity, activation of C type fibers generally requires a longer pulse width than activation of a myelinated Aβ fiber. In a preferred embodiment, the use of a low mid-range pulse is used to in order to preferably activate myelinated fibers.

TABLE 3

Electrical therapy: Pulse Width Table
Electrical therapy: Pulse Width Table

| Pulse width designation | Range in microseconds |
| --- | --- |
| Very short pulse | 10-50 |
| Short pulse | 50-150 |
| Low mid-range pulse | 151-350 |
| High mid-range pulse | 351-550 |
| Long pulse | 551-1000 |
| Very long pulse | 1001-4000 |

Figure 8B:
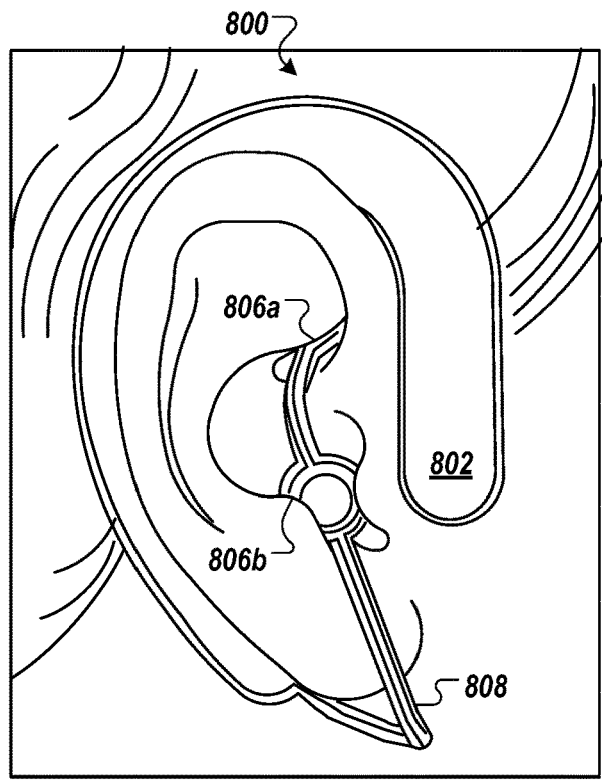

To stimulate the various neural structures discussed above, in some implementations, treatment devices may be designed for positioning against various surfaces on or surrounding a patient's ear. Turning to FIG. 8A and FIG. 8B, an example treatment device 800 is shown including an auricular component 802 configured to contact skin behind and around a patient's ear. The auricular component 802, for example, may wrap around a back of an ear and include electrodes 804 for contacting skin surfaces in front of and behind the ear. The auricular component 802 is connected to an inner ear component 806 by a connector 808.

The connector 808, in some embodiments, is releasably connected between the auricular component 802 and the inner ear component 806. For example, at least one of a proximal (auricular component 802 side) end or at distal (inner ear component 806) end of the connector 808 may be designed for releasable connection. In other embodiments, the connector 808 is integrated with the auricular component 802 and inner ear component 806, behaving as a conduit for bridging an electrical connection between the auricular component 802 and the inner ear component 806.

In some implementations, the auricular component 802 includes a number of electrodes 804 that are configured to be in contact with the dermis on and around the outer ear. The auricular component 802, in some examples, may include an electrode positioned for proximity to vagal-related neural structures, an electrode positioned for proximity to a neural structure related to the auriculotemporal nerve, an electrode positioned for proximity to neural structures related to the great auricular nerve or its branches, and/or an electrode positioned for proximity to the lesser occipital nerve or its branches.

Additionally, the treatment device 800 includes a pulse generator or controller (not illustrated) for delivering a series of therapeutic electrodes to the treatment device 800. The pulse generator may include management software for controlling therapy delivery. The management software, in some examples, may include adjustment functionality for customizing the therapeutic output, input/output (I/O) functionality (e.g., for confirmation of therapeutic delivery), and/or metrics collection functionality for generating and retaining data such as stimulation logs, diagnostic data, and/or event data.

In some embodiments, the controller records overall therapeutic delivery so the caregiver/clinician can measure compliance. In one example, the management software may notify the wearer, caregiver, clinician if the device has stopped delivering therapy. In a further example, the device may provide an indication of health status, such as reporting on the condition of the electrodes, the conductive surface (e.g., hydrogel), and/or the analgesic. In another example, the management software may report data related to use, events, logs, errors, and device health status. The controller, for example, may collect information for presentation in usage reports (e.g., generated by a separate portable device app or computer program). In some implementations, the treatment device 800 includes a unique identifier that can be used in identifying users and reported data so that multiple devices can be monitored using a single software application (e.g., patients at a certain facility and/or under supervision of a certain doctor).

In some embodiments, a pulse generator is connected to the auricular component 802 by a second connector. The second connector may be releasably connected between the auricular component 802 and the pulse generator. For example, at least one of a proximal (auricular component 802) end or a distal (pulse generator) end of the second connector may be designed for releasable connection. In other embodiments, the second connector is integrated with the auricular component 802 and the pulse generator, behaving as a conduit for bridging an electrical connection between the auricular component 802 and the pulse generator. In further embodiments, a pulse generator is built into the auricular component 802.

The first connector 808 and/or the second connector, in some embodiments, includes a keyed releasable connection with a corresponding port of the treatment device 800 for snug (e.g., non-spinning) connection or for assuring electrical alignment. In some embodiments, the first connector 808 and/or the second connector is designed for locking connection with the treatment device 800. The locking connection, for example, may be a water-resistant locking connection to protect against shorting due to moisture from sweat, rain, etc.

In some embodiments, the auricular component 802 and/or the inner ear component 806 are designed from inexpensive materials, allowing the apparatus to be disposable, thereby lowering the cost per treatment and eliminating the need for maintenance. Disposable apparatus also provides for greater hygienics.

In an illustrative example, a treatment device such as the device 800 of FIGS. 8A and 8B may be donned as follows. In implementations having protective liners on the skin adhesive and/or electrodes, remove the protective liners before use. Apply the auricular component 802 around the auricle of the patient and press against the patient's skin such that exposed skin adhesives and adhesives/hydrogels (or other conductive adhesive) adhere to the skin. Next, place the inner ear component 806 in the ear such that a first portion 806b of the inner ear component 806 is positioned outside the external ear canal in the cavum. Finally, flex or compress a second or distal portion 806a of the inner ear component 806 supporting a cymba electrode 810 until it engages with the cymba of the ear.

Electrodes can be made larger or combined such that, for example, multiple electrodes are combined into one large contact, such as the contact pads 804a, 804b, and 804c. A treatment device, in some embodiments, includes a set of electrodes configured to be virtually grouped together to form one or more effective electrodes. For example, a first grouping of electrodes can be equivalent to electrode 804a, a second grouping of electrodes can be equivalent to electrode 804b, and a third grouping of electrodes can be equivalent to electrode 804c. Grouping smaller electrodes provides the ability to have multiple electrodes each with its own independently controlled current source, allowing for current steering, thereby providing better spatial resolution and targeting capabilities. Electrodes may be virtually grouped by processing circuitry.

In some implementations, a treatment device includes one or more haptic feedback actuators between electrode pairs. The haptic feedback actuator(s), for example, may move from a first position to a second position in repetitive patterns to mask sensations felt by stimulation of the electrodes. The haptic feedback actuator(s) may be configured to isolate or electrically separate conductive shunting pathways between electrodes, for example between portions of conductive gel.

Figure 9B:
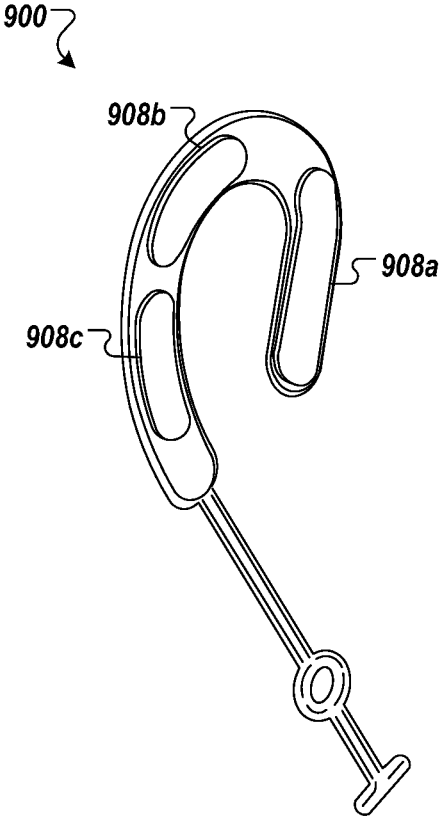
Figure 9C:
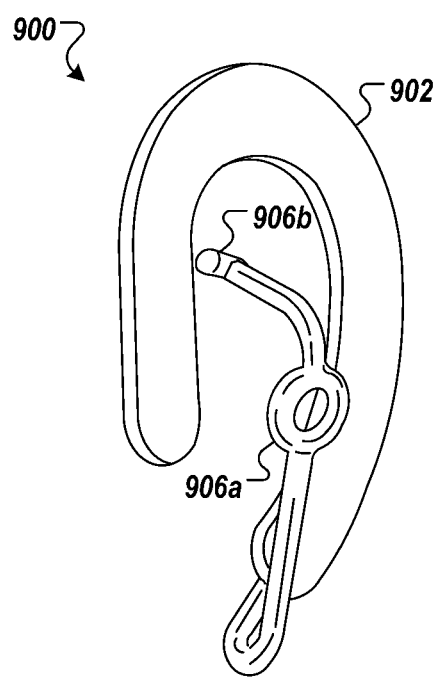

Turning to FIG. 9A through FIG. 9C, in some implementations, an earpiece assembly 900 includes a printed circuit board (PCB) layer having electrodes. A flexible PCB can include electronic components to suppress electrical spikes as well as a component to identify and/or uniquely identify the PCB. Exposed conductive surfaces on the PCB can serve as contact point to connect hydrogels or other conductive adhesive materials to the PCB. The PCB extends forming a cable-like structure (connector) 904 to integrate an inner ear component 906 and an auricular component 902 without the need for soldering and/or connecting during assembly. The earpiece assembly 900, in some embodiments, is extremely flexible, allowing it to easily conform to different shapes presented by the anatomic variability of users. In some embodiments, the earpiece assembly 900 is at least partially custom printed to provide a fitted shape for the user.

In some implementations, the flexible PCB is encapsulated in a protective covering. The protective covering can be made from a flexible material such as silicone. The protective covering may be applied in varying thickness and/or densities, for example to improve comfort during wear, to increase retention strength of the device during wear, and to protect the circuitry from damage. The encapsulation is done with at least one material. In some embodiments, the encapsulation is done at least in using one mold and at least one molding step. The flexible PCB, for example, may be at least partially covered with a closed cell foam.

Turning to FIG. 9B, in some implementations, the auricular component 902 includes a set of electrode contacts 908a, 908b, and 908c. More or fewer electrode contacts may be included, and each electrode contact may be in electrical contact with one or more electrodes of the PCB layer. The protective covering, in some implementations, includes openings to expose contacts to electrodes. For example, electrode contact pads 908a-c may be added to exposed regions. In other implementations, the entire earpiece assembly 900 is printed, including the protective layer and the contact pads 908a-c.

In some embodiments, the skin-contacting electrodes of the earpiece assembly 900 are formed in layers. For example, a first layer may include a medical-grade double-sided conducting adhesive tape, the second layer may include a conductive flexible metallic and/or fabric mesh for mechanical robustness and homogenic electrical field distribution, and a third layer may include a self-adhesive hydrogel, or other skin-contacting conductive adhesive. In other embodiments, a two-layer version may be provided having a first layer configured for mechanical robustness and homogenic electrical field distribution and a second layer including a self-adhesive hydrogel, or other skin-contacting conductive adhesive. The PCB electrodes may be formed such that they cover a similar surface area as the skin-contacting hydrogel electrodes. In this manner, homogenic electrical field distribution may be achieved at the hydrogels without the need of any additional conductive layer.

In some implementations, a first portion 906a of the inner ear component 906 and/or a second portion 906b of the inner ear component 906 includes one or more stimulation electrodes. The electrodes may be exposed (e.g., no protective layer covering) and/or one or more contact pads may be applied to the first portion 906*a* and/or the second portion 906*b*.

The connector 904, in some implementations, is designed to curve up to allow for insertion of the inner ear component 906, as illustrated in FIG. 9C. In other implementations, the connector 904 is printed as a spring (e.g., telephone cord) to provide mobility of the inner ear component 906.

In some implementations, the earpiece assembly 900 connects to a pulse generator via a slim keyed connector. In other implementations, the PCB layer includes controller circuitry for generating pulses.

In some implementations, a pulse generator for use with an earpiece device includes a battery and circuitry configured to produce therapy stimulation in communication with the electrodes of the earpiece device. In some embodiments, the pulse generator includes at least one antenna configured to receive programming instructions encoding stimulation parameters. The system may be rechargeable to allow for long-term use.

In some embodiments, the auricular component of the earpiece device is connected to an electrical pulse generator which produces the therapy stimulation going to the electrodes on the auricular component and the inner ear component. In some implementations, the pulse generator is located in close proximity with the auricle of the patient. For example, the pulse generator may be designed into or releasably connected to a head apparatus similar to an over the head or back of the head headphones band or earmuffs band. In another example, the pulse generator may be releasably retained in a pocket of a cap or head wrap worn by a patient. In other embodiments, the pulse generator is placed on the body of the user, for example on the pectoral region just below the clavicle. In another embodiment, the pulse generator can be clipped to the user's clothing or carried in the user's trousers pocket or in a specially designed pouch. In further embodiments, the pulse generator is built into the auricular component of the earpiece device.

In some embodiments, the pulse generator includes an input/output (I/O) interface for user control of the therapy. The I/O interface, for example, may include a number of controls, such as buttons, dials, or a touch pad, for adjusting therapy. In some examples, the I/O interface may include one or more of a mode selection, a length of time selection, or a stimulation strength control. Separate controls, in a further example, may be provided for the adjustment of the electrodes of the concha apparatus and for the electrodes of the earpiece.

In some embodiments, the pulse generator is remotely configurable via wireless communication. In some embodiments, the wireless remote device may periodically request therapy status and in some embodiments the status, including any changes, may be communicated to a 3rd party such as a healthcare provider who is monitoring the therapy being applied to the user. For example, therapy provided via the pulse generator may be controlled or adjusted at least in part using a peripheral device such as a mobile device, a tablet, or a personal computer. For example, a mode and/or stimulation strength may be adjusted by a clinical user (e.g., doctor, nurse, occupational therapist, etc.), while the timing (e.g., powering on and off and/or length of time setting) of the stimulation may be user-controlled via the I/O interface of the pulse generator. In another example, a software update to the pulse generator may be delivered via wireless communication. The wireless communication, in some examples, can include radio frequency (RF) communication (e.g., Bluetooth) or near-field communication (NFC). The wireless communication may be enabled via an application installed on the peripheral device.

In some embodiments, other components of the treatment device are configurable by or capable of communication with a peripheral device. For example, data collected by the treatment device may be transferred to the peripheral device and thereby exchanged via a computing cloud with third parties such as healthcare professionals and/or healthcare providers.

In some implementations, a therapeutic auricular device is designed for continuous use for, in some examples, at least thirty minutes, between a half hour and an hour, between one hour and five hours, or for a complete workday (e.g., approximately 8 to 10 hours). However, a device designed for continuous use can be utilized intermittently for short time intervals, or specific duty cycles. For example, a device could be active for one 5-to-10 minute period or for several of such periods with an off time between the active periods. For example, for military training and/or operations, soldiers may be provided with continuous or intermittent therapy for a number of hours. A power pack, for example, may be tethered to the therapeutic auricular device and attached to/integrated into a variety of standard equipment, such as a military helmet or air traffic controller headset, to provide adequate power for longer term use. The power pack may include additional circuitry, such as controller circuitry for delivering stimulations.

In some implementations, control circuitry and/or a power unit may be releasably attachable to a therapeutic auricular device. For example, a controller component may snap onto or otherwise engage with the auricular component of a therapeutic auricular device to provide stimulation therapy. The therapeutic auricular device may be disposable, and the releasable control circuitry and/or power unit may be re-usable.

A therapeutic auricular device, in some implementations, is designed for durability and retention throughout strenuous activities such as, in some examples, military training and/or military operations, police operations, and/or sports competitions (including e-sports). The therapeutic auricular device, for example, may include water resistance features, impact resistance features, adhesive features and/or anti-slippage features.

In some embodiments, a therapeutic auricular device includes few or no inputs accessible to the wearer. For example, the therapeutic auricular device may include a power control button or switch. A disposable therapeutic auricular device may include a removable battery tab that, when removed, engages power to the device and initiates therapeutic delivery.

In some embodiments, a therapeutic auricular device includes circuitry and/or other components to integrate the therapeutic auricular device with other devices, such as communications devices. For example, the therapeutic auricular device may include a wireless speaker component, wireless signal reception, and/or wireless signal transmission. A therapeutic auricular device may include a Bluetooth or other limited range wireless communication module for remote therapy initiation. In an illustrative example, upon the beginning of a mission or military operation, the therapeutic auricular devices of a group of individuals (e.g., military battalion, special weapons and tactics (SWAT) team, etc.) may be triggered to initiate therapy via a wireless command or signal issued by a single master controller. The signal may be a radio frequency (RF) signal issued to a passive or active RF component of the therapeutic auricular device.

Figure 10A:
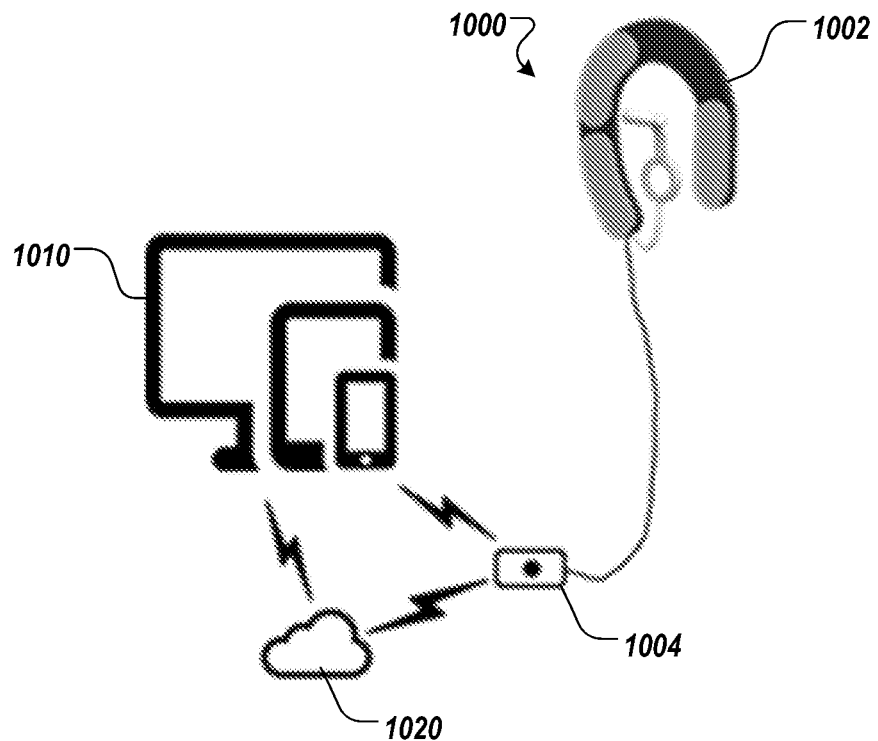
FIGS. 10A-10C are drawings of example systems including an example treatment device in communication with remote systems through a computing cloud and/or a peripheral device.
Figure 10B:
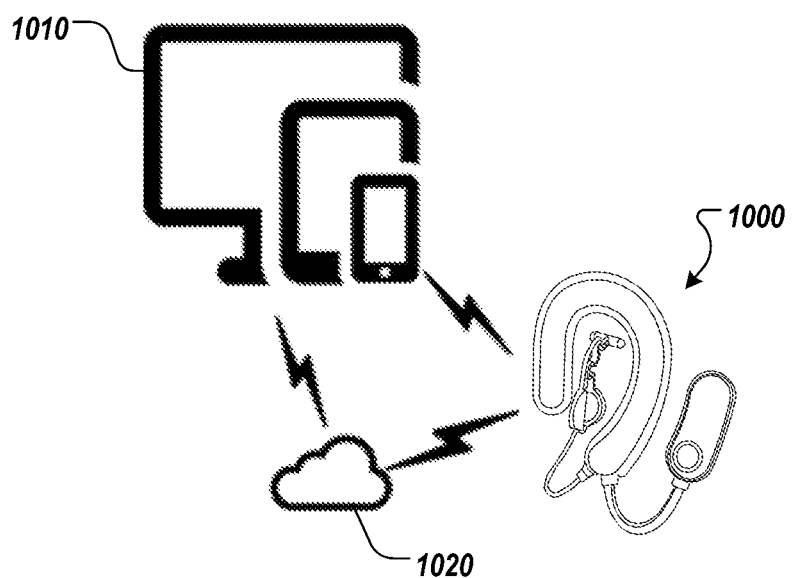
Figure 10C:
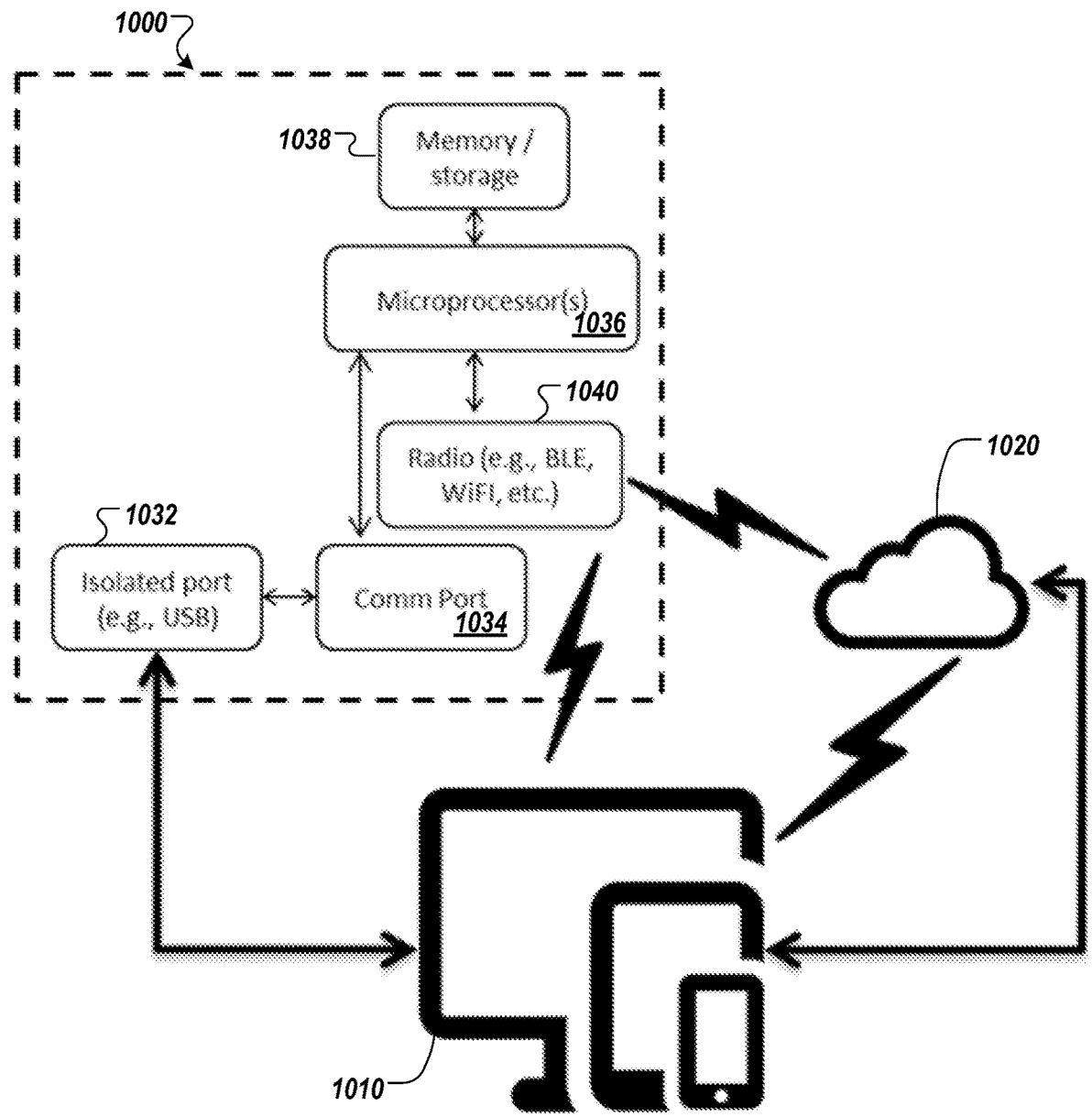

Turning to FIG. 10A through FIG. 10C, in some implementations, a treatment system can include a treatment device 1000 in communication with a network 1020 and/or one or more peripheral devices 1010. Certain peripheral devices 1010, further, may enable communication between the treatment device 1000 and one or more third parties. Examples of peripheral devices 1010 include a personal computer, a tablet, or phone. In some embodiments, the peripheral device(s) 1010 include a fitness-monitoring device, such as a Fitbit, Apple Watch, or Garmin Smartwatch. In some embodiments, the peripheral device (s) 1010 include a health-monitoring device, such as a glucose meter, a holter monitor, a motion detector, an accelerometer, an electrocardiogram (EKG) monitor, an electromyography (EMG) monitor, or an electroencephalogram (EEG) monitor. Further, the peripheral devices 1010, in some embodiments, include a remote server, server farm, or cloud service accessible via the network 1020. Certain peripheral device (s) 1010 may communicate directly with the treatment device 1000 using short-range wireless communications, such as a radio frequency (RF) (e.g., Bluetooth, Wi-Fi, Zigbee, etc.) or near-field communication (NFC). Certain peripheral device(s) 1010 may communicate with the treatment device 1000 through another peripheral device 1010. For example, using Bluetooth communications, information from the treatment device 1000 may be forwarded to a cloud service via the network 1020 (e.g., using a Wi-Fi, Ethernet, or cellular connection). The network 1020, in some examples, can include a local area network (LAN), wide area network (WAN), metro area network (MAN) or the Internet. In some embodiments, the network is a clinical LAN used for communicating information in a medical environment, such as a hospital, in a secure (e.g., HIPAA-compliant) manner.

In an example illustrated in FIG. 10A, the treatment device 1000 is shown including an auricular component 1002 connected via a connector to a pulse generator 1004, and the pulse generator 1004 is wirelessly connected to the peripheral device(s) 1010 and/or the network 1020. This configuration, for example, may enable a patient, caregiver, or clinical user to adjust settings and/or monitor treatment controlled by the pulse generator 1004. For example, an application running on a peripheral device 1010 may provide one or more adjustable controls to the user for adjusting the delivery of therapy by the pulse generator 1004 to the patient via the auricular component 1002. Further, feedback data gathered by the auricular component 1002 and/or the pulse generator 1004, such as sensor feedback, may be supplied by the pulse generator 1004 to one or more of the peripheral devices 1010. The feedback, for example, may include sensor signals related to symptoms of the patient being treated by the treatment device 1000. A clinical user monitoring sensor metrics related to these signals may manually adjust the delivery of therapy accordingly using the one or more adjustable controls provided by the application. Further, in some implementations, the feedback may be used by one of the peripheral devices 1010 to generate a notification for review by the patient, a caregiver, or a clinician. The notification, for example, may include a low power notification, a device removed notification, or a malfunction notification. In an illustrative example, the treatment device 1000 may monitor impedance measurements allowing closed-loop neurostimulation. The notifications regarding removal or malfunction, for example, may be issued upon determining that the impedance measurements are indicative of lack of a proper contact between one or more electrodes of the treatment device 1000 and tissue on or surrounding the patient's ear. The notifications, for example, may be delivered to the patient and/or one or more third parties via an application executing on one of the peripheral devices 1010. For example, the application may issue an audible alarm, present a visual notification, or generate a haptic output on the peripheral device 1010. Further, in some embodiments, the application may issue a notification via a communication means, such as sending an email, text message, or other electronic message to one or more authorized users, such as a patient, caregiver, and/or clinician.

Conversely, in some implementations, the configuration illustrated in FIG. 10A enables automatic adjustment of therapy delivery by reviewing feedback provided by the treatment device and/or one or more peripheral devices 1010 (e.g., fitness monitors and/or health monitors used by the patient). In one example, a cloud platform accessible via the network 1020 may receive the feedback, review present metrics, and relay instructions to the pulse generator 1004 (e.g., via a Wi-Fi network or indirectly via a local portable device belonging to the patient such as a smart phone app in communication with the treatment device 1000). The pulse generator 1004, in a further example, may gather feedback from the one or more fitness monitor and/or health monitor devices 1010, analyze the feedback, and determine whether to adjust treatment accordingly.

Turning to FIG. 10B, in some implementations, the auricular component 1002 of the treatment device 1000 may further be enabled for wireless transmission of information with one or more peripheral devices 1010. For example, the auricular component 1002 may include a short-range radio frequency transmitter for sharing sensor data, alerts, error conditions, or other information with one or more peripheral devices 1010. The data, for example, may be collected in a small non-transitory (e.g., non-volatile) memory region built into the auricular component 1002.

In other implementations, the pulse generator 1004 is included in the auricular component 1002 that is, they are co-located thus the need for an extension cable to connect them is not necessary. The auricular component 1002 and pulse generator 1004 may be wirelessly connected to an electronic device (for example a personal computer, a tablet or a phone) 1010 and/or to a remote server 1010 via the network 1020. In turn, in some embodiments, the electronic device 1010 is also wirelessly connected to a remote server via the network 1020.

As shown in FIG. 10C, different communication components of the treatment device 1000 can be in communication with the peripheral device(s) 1010 or network 1020. In some implementations, the treatment device 1000 includes at least one isolated port 1032 for wired communication with the peripheral device 1010. The isolated port 1032, in some examples, may be a universal serial bus (USB) connection (e.g., a mini-USB connection, a micro-USB connection, a USB-C port, etc.), an Ethernet port, or a Serial ATA (SATA) connector. The isolated port 1032, for example, may be included in the pulse generator 1004 for updating a software version running on the pulse generator 1004 or for reprogramming treatment settings of the pulse generator 1004. The isolated port(s) 1032 may be connected to a communications port engine 1034 for enabling communications between a peripheral device 1010 and the treatment device 1000 via the isolated port 1032. The communications port engine 1034 may couple the isolated port 1032 to one or more microprocessors 1036. For example, the communications port engine 1034 may establish a direct (e.g., wired)

communication link with one of the peripheral devices 1010 to transfer data 1020 from a memory 1038 to the peripheral device 1010.

Further, a wireless radio frequency (RF) antenna (e.g., transmitter or transmitter/receiver) 1040, in some implementations, is included in the treatment device 1000. The RF antenna 1040 can be in wireless communication with the peripheral device(s) 1010 directly or via the network 1020. The RF antenna 1040, in combination with processing circuitry for generating wireless communications (e.g., another communication port engine 1034 or a portion of the microprocessor(s) 1036) may function as a broadcast antenna, providing information to any RF receiver in a receiving region of the treatment device 1000. For example, the RF antenna 1040 may broadcast sensor data, sensor metrics, alerts, alarms, or other operating information for receipt by one or more peripheral devices 1010. In other implementations, the RF antenna 1040, in combination with additional processing circuitry, may establish a wireless communication link with a particular peripheral device 1010. The wireless communication link, in some embodiments, is a secure wireless communication link (e.g., HIPAA-compliant) for sharing patient data with the peripheral device(s) 1010. The wireless communication link may be used to receive control settings from a peripheral device 1010 for controlling the functionality of the pulse generator 1004, for example.

Figure 11:
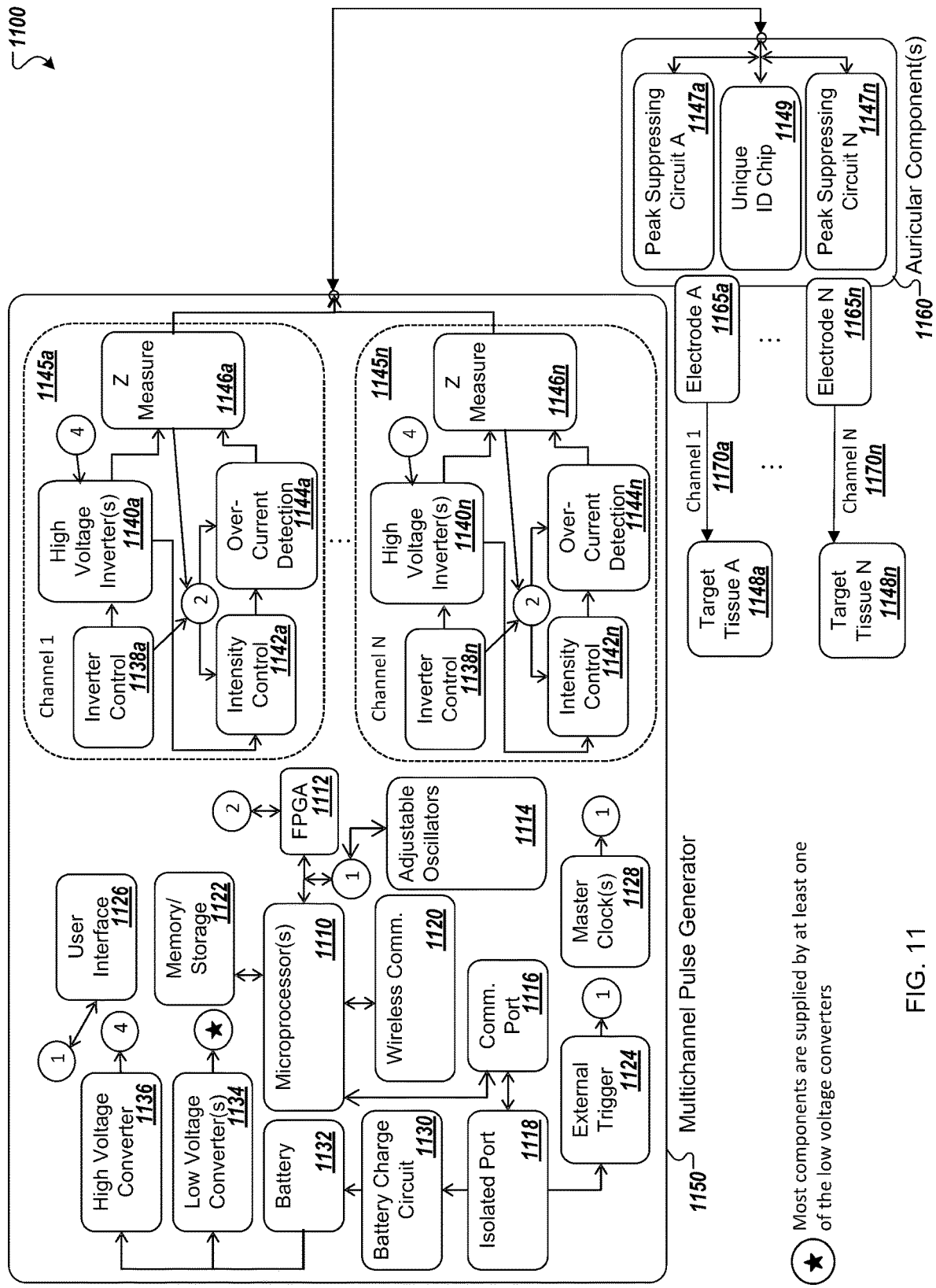
FIG. 11 is a block diagram of components of an example pulse generator in communication with an example auricular therapy device.

Turning to FIG. 11, a block diagram 1100 of example components of a pulse generator 1150 in communication with example components of an auricular component 1160 is shown. The multichannel pulse generator circuit 1150, in some embodiments, has at least one microcontroller or a microprocessor 1110 with at least one core. When multiple microcontrollers or multiple cores are present, for example, one may control the wireless communication 1120 and other core(s) may be dedicated to control the therapy. In some implementations, a low power programmable logic circuitry (e.g., field programmable gate array (FPGA) or programmable logic device (PLD)) 1112 is also provided. For example, the microcontroller 1110 may be configured to switch into a low power mode as frequently as possible while the programmable logic circuitry 1112 controls therapy delivery.

In some embodiments, an inverter circuit 1145*a-n* is used to generate biphasic/bipolar pulses. In some embodiments, one inverter circuit 1145*a-n* is used per channel 1170*a-n*, while in other embodiments, a single inverter circuit 1145 is used for multiple channels 1170*a-n*. Each channel 1145*a-n*, for example, may target a different anatomical area (e.g., tissue region) 1148*a-n*. A high voltage compliance (e.g., >50V, in other embodiments >70V, and yet in others >90V) may be used to ensure there is enough margin on the electrical potential to generate current demanded by the intensity control 1142*a-n* of each inverter circuit 1145*a-n* by providing one or more high voltage inverters 1140*a-n* per inverter circuit 1145*a-n*. In order to enhance safety, in some embodiments, an over current detection circuit 1144*a-n* is provided in each inverter circuit 1145*a-n*. In some embodiments, an impedance measuring circuit 1146*a-n* is provided in each inverter circuit 114*a-n*. The impedance measuring circuit 1146*a-n*, for example, may support tracking impedance over time to identify failure of sufficient therapy delivery. In some examples, therapy delivery may be compromised when the electrodes are not in contact or in good contact with the target tissue 1148*a-n*, when a cable or connector between the multichannel pulse generator 1150 is disconnected from one of the auricular component(s) 1160, or where the electrodes have deteriorated or are defective. Monitoring impedance over time provides the added advantage that the condition of the contact electrode can be followed; thus allowing the controller to alert the user when the contact electrodes are close to their end of life or no longer viable.

In some embodiments, an isolated port 1118, such as a universal serial bus (USB) is used to charge the battery, and to communicate with the microcontroller(s) 1110. The communication can be both ways, such that instructions or entire new code can be uploaded to the microcontroller(s) 1110 and information stored in a memory 1122 may be downloaded. In some embodiments, the memory 1122 or additional memory can be added to the circuitry as an external component (e.g., in wireless or wired communication with the pulse generator 1150). For example, the isolated port 1118 (e.g., USB) may be used to connect memory to the pulse generator 1150. In other embodiments, at least portions of the memory 1122 may be internal to the microcontroller(s) 1110. In some embodiments, the FPGA 1112 may also have internal memory.

In some embodiments, an external trigger circuit 1124 is included, such that the stimulation can be started and/or stopped via an external signal. In some embodiments, the external trigger signal can be passed through the isolated port 1118; in yet other embodiments a modified USB configuration (i.e., not using the standard USB pin configuration) can be used to pass the trigger signal. Using a modified USB configuration will force a custom USB cable to be used, thus ensuring that an external trigger cannot be provided by mistake using an off-the-shelf USB cable.

In some embodiments, a hardware user interface is provided for interacting with the multichannel pulse generator 1150 via user interface circuitry 1126. In an example, the user interface circuitry 1126 can include of buttons, LEDs, haptic (e.g., piezoelectric) devices such as buzzers, and/or a display, or a combination of any of them. In some embodiments, the user interface circuitry 1126 includes signal processing components for interpreting user interface commands delivered via an external device (e.g., through the wireless communications 1120). The external device, in some examples, may be a smart phone app, a tablet computer, or a medical monitoring device (e.g., in a hospital setting).

In some embodiments, an external master clock 1128 is used to drive the microcontroller(s) 1110 and/or the FPGA 1112. In other embodiments the clock(s) of the components can be internal or integrated or co-packaged with the microcontroller(s) 1110 and/or the FPGA 1112. In some embodiments, one or more oscillators, including in some cases adjustable oscillators 1114 are used to set pulse parameters such as, for example, frequency and/or pulse width.

In some embodiments, the auricular component 1160 is made from a thin flex PCB or printed electronics, such that it is light weight and can be easily bent to accommodate different anatomies. In some embodiments, the auricular component 1160 has more than one channel. The auricular component 1160, or each channel thereof, may include a peak suppressing circuit 1147*a-n* and electrodes 1165*a-n* to contact the skin at the location of the target tissue 1148*a-n*. In some embodiments, the auricular component(s) 1160 includes a unique chip identifier or unique ID chip 1149. The unique ID chip can be used to track usage as well as to prevent other non-authorized circuits from connecting to the multichannel pulse generator 1150. At least one auricular component(s) 1160 is connected to the multichannel pulse generator 1150.

In an exemplary embodiment, the system utilizes feedback to monitor and/or modify the therapy. The feedback may be obtained from one or more sensors capable of monitoring one or more symptoms being treated by the therapy. For example, upon reduction or removal of one or more symptoms, a therapeutic output may be similarly reduced or ceased. Conversely, upon increase or addition of one or more symptoms, the therapeutic output may be similarly activated or adjusted (increased, expanded upon, etc.). In some examples, the sensors may monitor one or more of electrodermal activity (e.g., sweating), movement activity (e.g., tremors, physiologic movement), glucose level, neurological activity (e.g., via EEG), muscle activity (e.g., via EMG) and/or cardio-pulmonary activity (e.g., EKG, heart rate, blood pressure (systolic, diastolic, and/or mean)). Imaging techniques such as MRI and fMRI could be used to adjust the therapy in a clinical setting for a given user. In other embodiments, imaging of pupillary changes (e.g., pupillary dilation) using, for example a common cellular phone and/or smart-glass glasses could be used to provide feedback to make therapy adjustments. In some implementations, one or more sensors are integrated into the earpiece and/or concha apparatus. One or more sensors, in some implementations, are integrated into the pulse generator. For example, periodic monitoring may be achieved through prompting the wearer to touch one or more electrodes on the system (e.g., electrodes built into a surface of the pulse generator) or otherwise interact with the pulse generator (e.g., hold the pulse generator extended away from the body to monitor tremors using a motion detector in the pulse generator). In further implementations, one or more sensor outputs may be obtained from external devices, such as a fitness computer, smart watch, or wearable health monitor.

The monitoring used may be based, in part, on a treatment setting. For example, EEG monitoring is easier in a hospital setting, while heart rate monitoring may be achieved by a sensor such as a pulsometer built into the earpiece or another sensor built into a low budget health monitoring device such as a fitness monitoring device or smart watch.

In an illustrative example, feedback related to electrodermal activity could be used to monitor and detect a speed or timing of a symptom and/or therapeutic outcome. In an example, the electrodermal activity could be sensed by electrodes on the therapeutic earpiece device. In another example, the electrodermal activity could be detected by electrodes on another portion of the body and communicated to the system. In some embodiments the electrodermal electrode can be such that it detects specific substances in the skin (e.g., cortisol, NOx, etc.) via electrochemical means. Elevated cortisol levels, for example, have been associated with predisposition to motion sickness, while increased nitric oxide metabolites (NOx) may be associated with onset of motion sickness.

In some implementations, the system can further include one or more motion detectors, such as accelerometers or gyroscopes, that can be used gather information to modulate the therapy. In an example, the one or more motion detectors are configured to detect a tremor and/or physiologic movement. In an aspect, the tremor and/or the physiologic movement can be indicative of the underlying condition and/or the treatment to the underlying condition. In an example, the tremor and/or physiologic movement can be indicative of symptoms associated with substance withdrawal. In an aspect, feedback from glucose monitoring can be used to modulate the therapy. In another example, motion data collected by the one or more motion detectors may be analyzed to identify movements of a subject likely to trigger motion sickness. In illustration, a gyroscope may be used to determine when a wearer is not in a generally vertical orientation, such as a disoriented pilot who may not be aiming along the horizon, to apply stimulations for treating motion sickness. Similarly, an accelerometer may be used to determine when a pilot's body is being exposed to G-forces that could lead to motion sickness. Various motion detectors may further collect signals indicative of air turbulence while flying and/or choppiness/swells in a body of water while on a watercraft, diving, or in a submersible vessel.

In yet other implementations, EKG can be used to assess heart rate and heart rate variability, to determine the activity of the autonomic nervous system in general and/or the relative activity of the sympathetic and parasympathetic branches of the autonomic nervous system, and to modulate the therapy. Autonomic nervous activity can be indicative of symptoms associated with substance withdrawal. In an aspect, the treatment device can be used to provide therapy for treating cardiac conditions such as atrial fibrillation and heart failure. In an example, therapy can be provided for modulation of the autonomic nervous system. In some implementations, the treatment device can be used to provide therapy to balance a ratio between any combinations of the autonomic nervous system, the parasympathetic nervous system, and the sympathetic nervous system.

In an aspect, the system can monitor impedance measurements allowing closed-loop neurostimulation. In an example, monitoring feedback can be used to alert patient/caregiver if therapy is not being adequately delivered and if the treatment device is removed.

Figure 12:
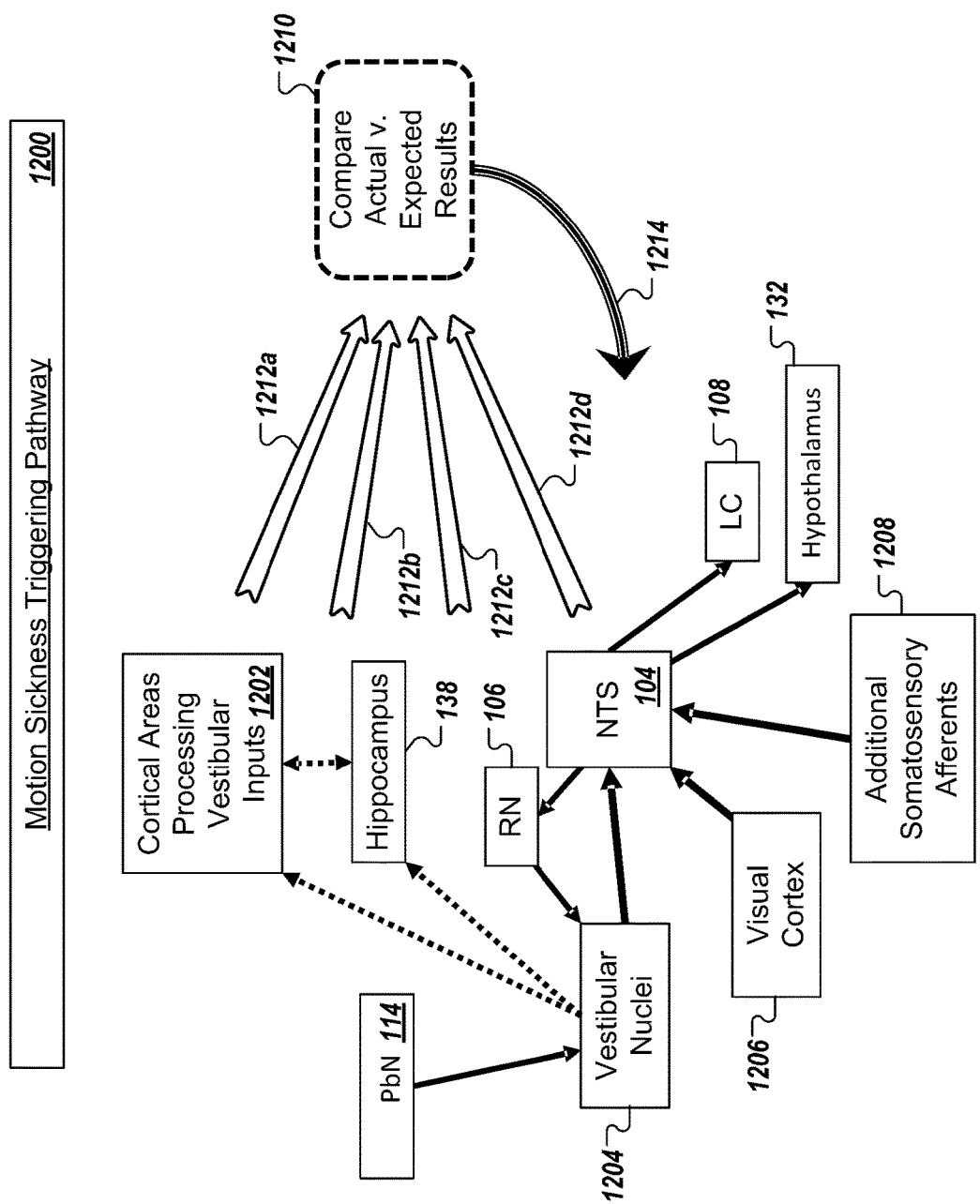
FIG. 12 illustrates example pathways in the autonomic nervous system involved in triggering motion sickness.

Turning to FIG. 12, a motion sickness response sensory input signal(s) is carried out via a Motion Sickness Triggering Pathway 1200. Although many brain regions or nuclei are involved in the response, the Nucleus Tractus Solitarius (NTS) 104 along with the Raphe Nucleus (RN) 16, Locus Coeruleus (LC) 108, Parabrachial Nucleus (PbN) 114 and the Paraventricular Nucleus PVN 206 (of FIGS. 2B and 13) are the main drivers of these pathways. The autonomic response triggering motion sickness starts with incoming sensory inputs 1212, which are integrated in the Nucleus Tractus Solitarius (NTS) 104. Sensory input signals produced from the Visual Cortex 1206 and Additional Somatosensory Afferents 1208 are processed and integrated in the NTS 104. Integrated signals are then compared with expected models, which may be stored in the Hippocampus 138 and/or the vestibular cortex (e.g., vestibular nuclei 1204) as Cortical Areas Processing Vestibular Inputs 1202.

These integrated signals serve as the reference against which internal models are compared 1210. Data suggests that these internal models are stored in areas involved in spatial orientation as well as motion awareness such as, for example, the hippocampus 138 and the vestibular cortex 1202, which include cortical areas activated in response to vestibular sensory system stimuli, including vestibular mismatch activity. When a mismatch occurs, e.g., between an integrated signal and a corresponding internal model, an autonomic response 1214 is elicited. This autonomic response 1214 involves brainstem areas such as, e.g., the Raphe Nuclei (RN) 106, the Locus Coeruleus (LC) 108, the Periaqueductal Gray (PAG), the Nucleus Basalis (NBM), the Nucleus Ambiguous (NA), the Ventral Tegmental Area (VTA), the Parabrachial Nucleus (PbN) 114, and the Pedunculopontine Nucleus (PPN), as well as hypothalamic areas 132 such as, e.g., the Paraventricular Nucleus (PVN) and the Arcuate Nucleus (ARC).

Figure 13:
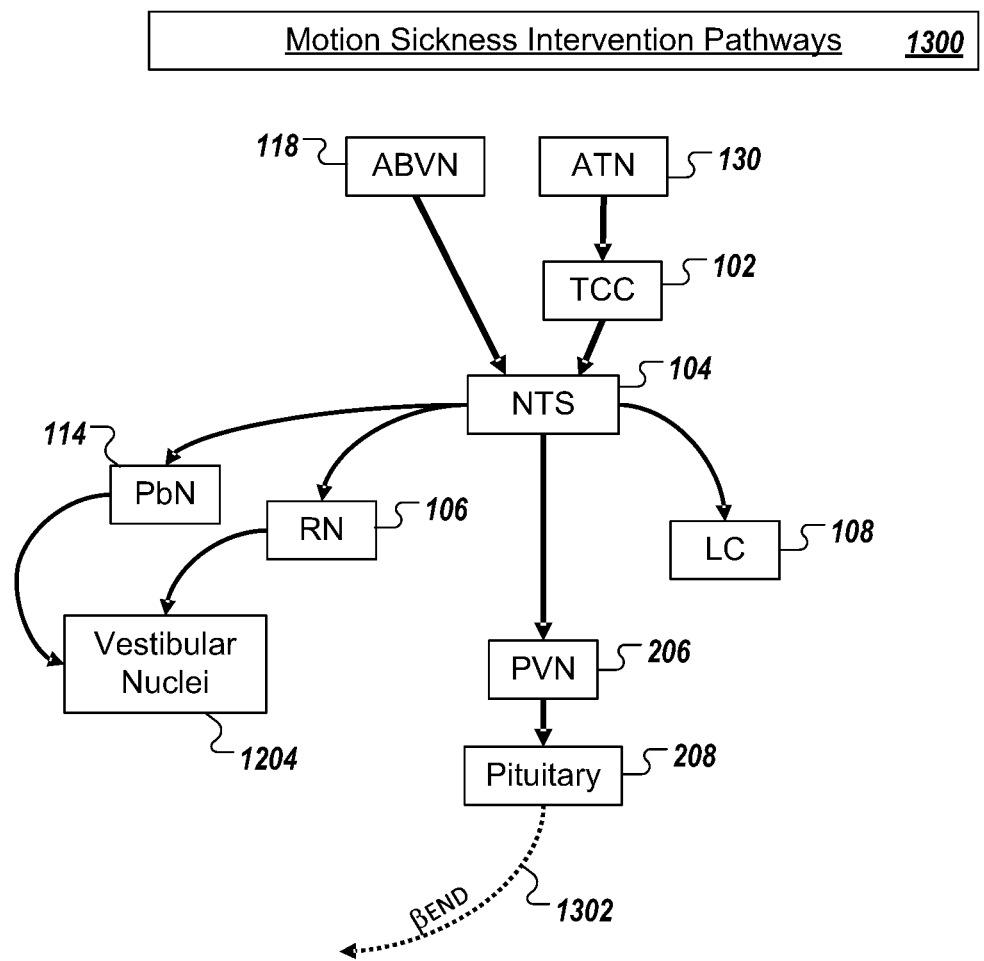
FIG. 13 illustrates example connections of a motion sickness intervention pathway.

To intervene against errant autonomic response brought about by motion sickness, turning to FIG. 13, a motion sickness intervention pathway 1300 may be activated. The LC 108 is the main producer of Norepinephrine (NE) in the Central Nervous System (CNS). By activating LC neurons, the availability of central NE is increased. This increase in NE can be seen as producing a similar effect of that of the sympathomimetics interventions, thus counteracting the inhibition of LC-NE circuits manifested in motion sickness. Further, the vestibular nuclei (VN) 1204 afferent serotonergic neurons from the RN 106 produce an inhibitory effect in VN activity. This decrease in VN activity decreases the VN efferent signals involved in the triggering of motion sickness symptoms. Further, by increasing pituitary 208 activity via the PVN 206, an increase in peripheral circulating β endorphins 1302 is produced, which, for example, mimics the abovementioned pharmacological intervention with Loperamide.

Figure 14:
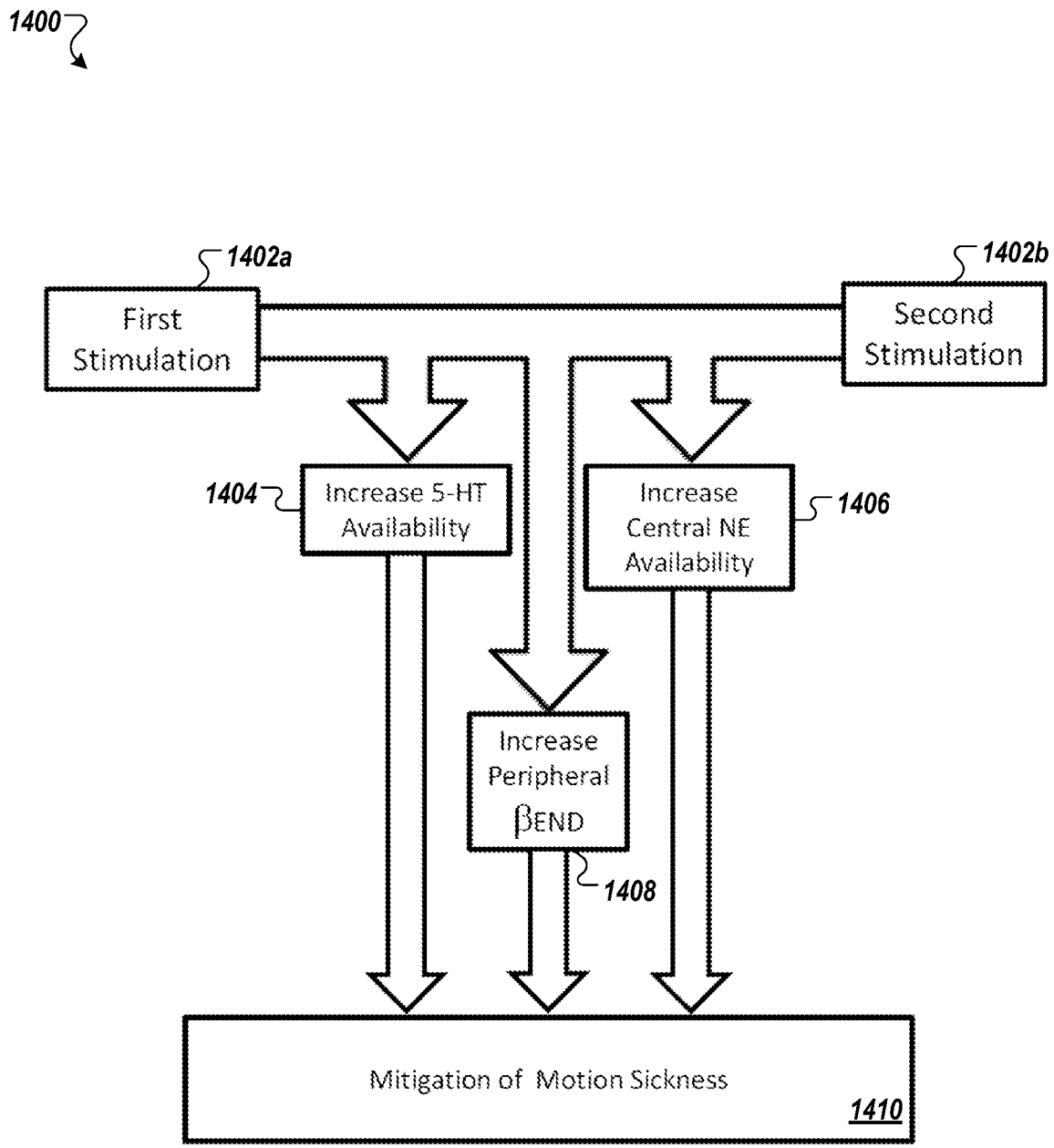
FIG. 14 illustrates example mechanisms for using electrical stimulation to treat motion sickness.

Turning to FIG. 14, a stimulation flow diagram 1400 illustrates stimulation mechanisms for mitigating (e.g., controlling and/or alleviating) motion sickness symptoms 1410 using a treatment device such as the treatment device 800 of FIG. 8A or the treatment device 900 of FIG. 9A. The stimulation mechanisms are produced by a first stimulation 1402a and a second stimulation 1402b. The first and second stimulations 1402, in some embodiments, are temporally separated (e.g., in overlapping or non-overlapping stimulations). In some embodiments, the first and second stimulations 1402 are physically separated (e.g., using a different electrode or set of electrodes contacting a different location on the patient). The first and second stimulations 1402, for example, may be provided via the motion sickness intervention pathways 1300 discussed in relation to FIG. 13. According to the motion sickness intervention pathways 1300, the first stimulation 1402a and/or the second stimulation 1402b may be configured to stimulate the ABVN 118 which projects to the NTS 104 and/or the ATN 130 which has a pathway to the NTS 104 via the TCC 102.

Responsive to a first stimulation 1402a, in some embodiments, 5-HT availability is increased (1404). Increasing 5-HT availability 1404 leads to an increase in BDNF expression. The BDNF, in turn, may function to protect monoamine neurotransmitter neurons and assist the monoamine neurotransmitter neurons to differentiate. The 5-HT availability may increase, for example, as activity in the RN 106 is unregulated (see motion sickness intervention pathways 1300 of FIG. 13). This increase in 5-HT is qualitatively comparable with the Rizatriptan therapy mentioned above.

Further, in some implementations, the first stimulation 1402a increases peripheral circulating β endorphins 1408 (e.g., as described in relation to the β endorphins 1302 of FIG. 13). In some embodiments, the second stimulation 1402b also increases peripheral circulating β endorphins 1408.

In all, the combined stimulation mechanisms of FIG. 14 may qualitatively mimic at least three pharmacological interventions that are known to have a positive outcome when treating motion sickness. The main advantage of applying the stimulation mechanisms over these three pharmacological interventions is that it is not systemically administered, it has no known side effects such as drowsiness, for example, and it is not addictive.

In some implementations, the second stimulation 1402b increases central NE availability (1406). As discussed in relation to FIG. 13, for example, activation of the LC through stimulation of the NTS 104 results in greater central NE availability.

In some embodiments, providing the first stimulation 1402a and providing the second stimulation 1402b involves providing a series of simultaneous and/or synchronized, and/or interleaved stimulation pulses. Each of the first stimulation 1402a and the second stimulation 1402b may be applied using the same or different parameters. The parameters, in some examples, may include pulse frequency (e.g., low, mid-range, high or very high) and/or pulse width. Further, the parameters may indicate electrode pairs for producing biphasic pulses. In a first illustrative example, the first stimulation may be applied using a low frequency, while the second stimulation is applied using a mid-range or high frequency. Conversely, in a second illustrative example, the first stimulation may be applied using a mid-range frequency, while the second stimulation is applied using a low frequency. Other combinations of low, mid-range, high, and/or very high frequency stimulations are possible depending upon the patient and the disorder being treated. Therapy may be optimized according to the needs of individual patients including custom stimulation frequency, custom pulse width, custom stimulation intensity (amplitude), and/or independently controlled stimulation channels.

Figure 15:
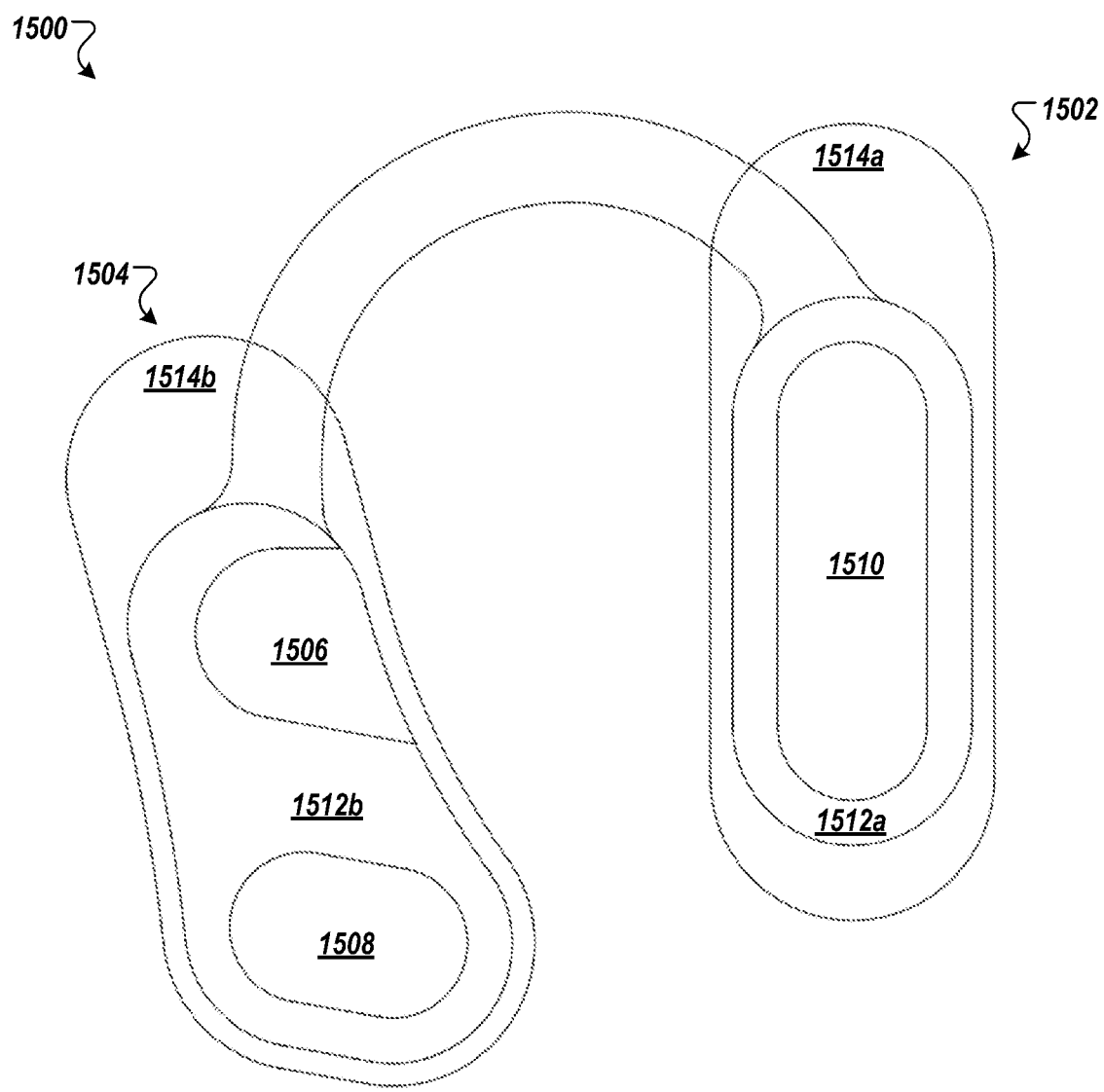
FIG. 15 illustrates an example wearable auricular neurostimulation (WANS) apparatus.

Turning to FIG. 15, a WANS apparatus 1500 includes a forward portion 1502 including a conductive adhesive region 1510 and a rear portion 1504 including conductive adhesive regions 1506 and 1508. The conductive adhesive region 1510 of the forward portion 1502, for example, may correspond to a first electrode. Similarly, the conductive adhesive region 1506 may correspond to a second electrode, and the conductive adhesive region 1508 may correspond to a third electrode.

Figure 16A:
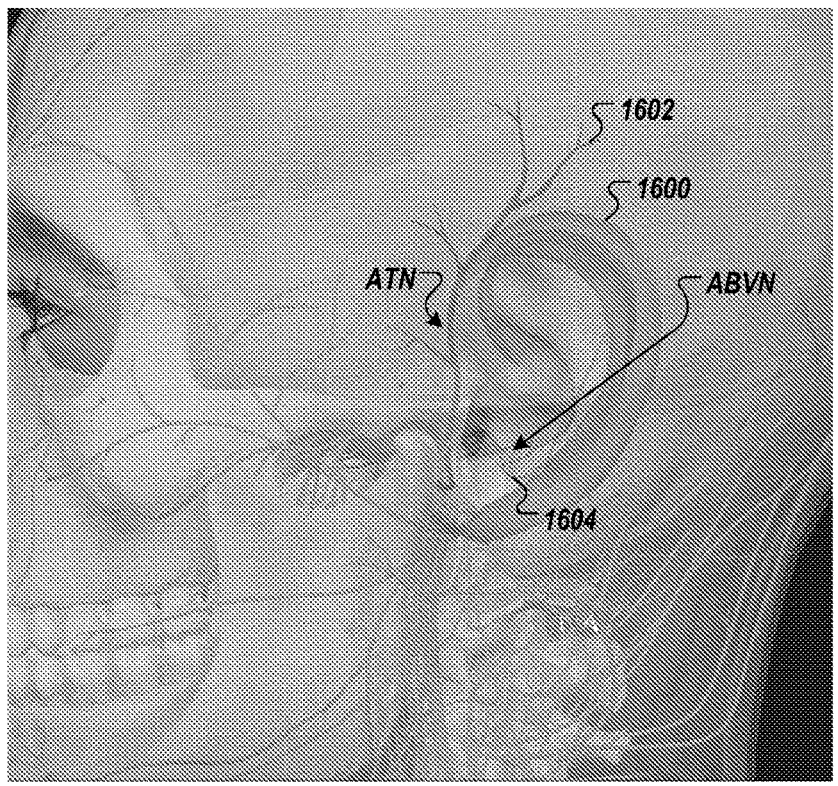
FIG. 16A through FIG. 16D, FIG. 17, and FIG. 18 illustrate example target nerve regions for directing therapy using a WANS apparatus.
Figure 16B:
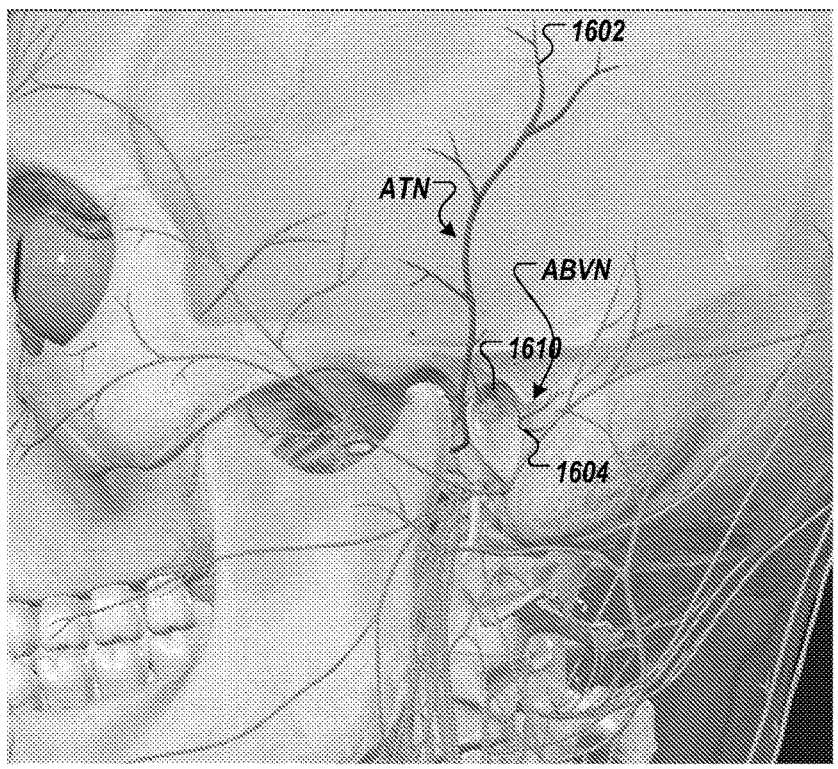

The conductive adhesive region 1510, in some implementations, is configured to contact skin of a wearer in a region of nerve structures of the auriculotemporal nerve (ATN) and/or nerve structures connected to the ATN, such that delivery of therapeutic stimulation via the conductive adhesive region 1510 modulates ATN activity. Turning to FIG. 16A and FIG. 16B, for example, ATN 1602 is illustrated in relation to an ear 1600 of a person (FIG. 16A), running generally in front of the ear 1600, as well as in relation, skeletally (FIG. 16B), to an ear canal 1610. In an illustrative example, an electrode in electrical communication with the conductive adhesive region 1506 may be positioned in proximity to the temporomandibular joint.

Figure 16C:
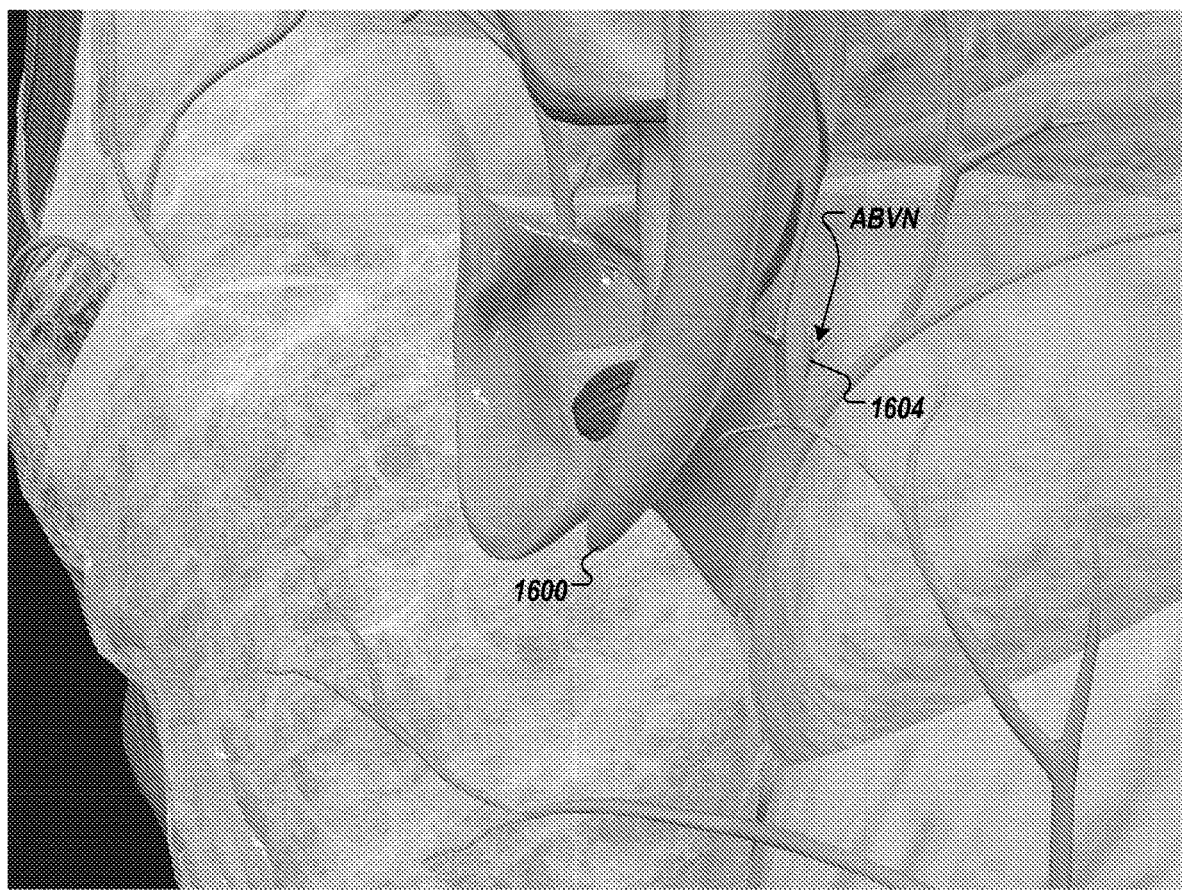
Figure 16D:
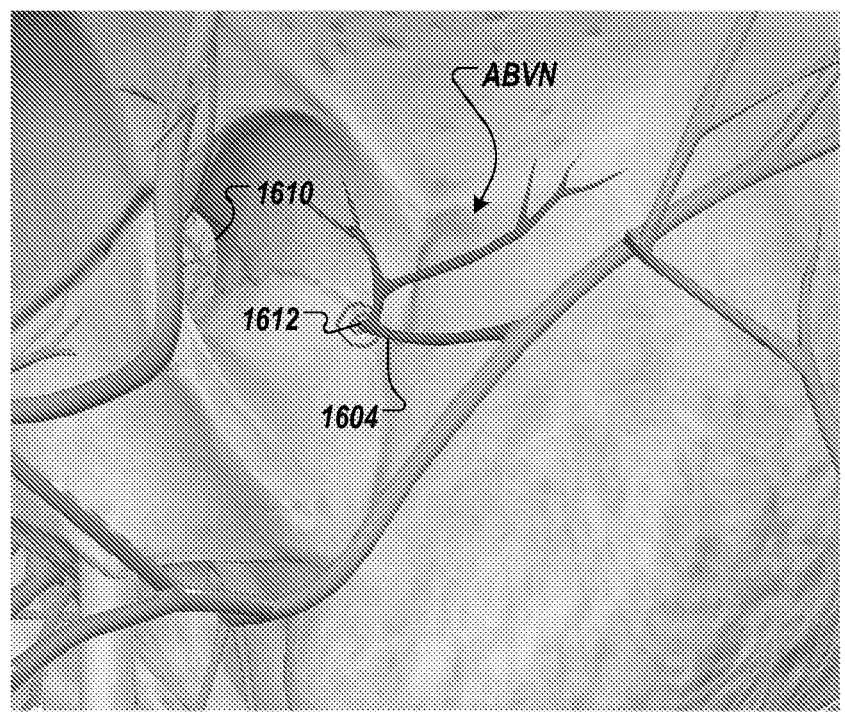
Figure 17:
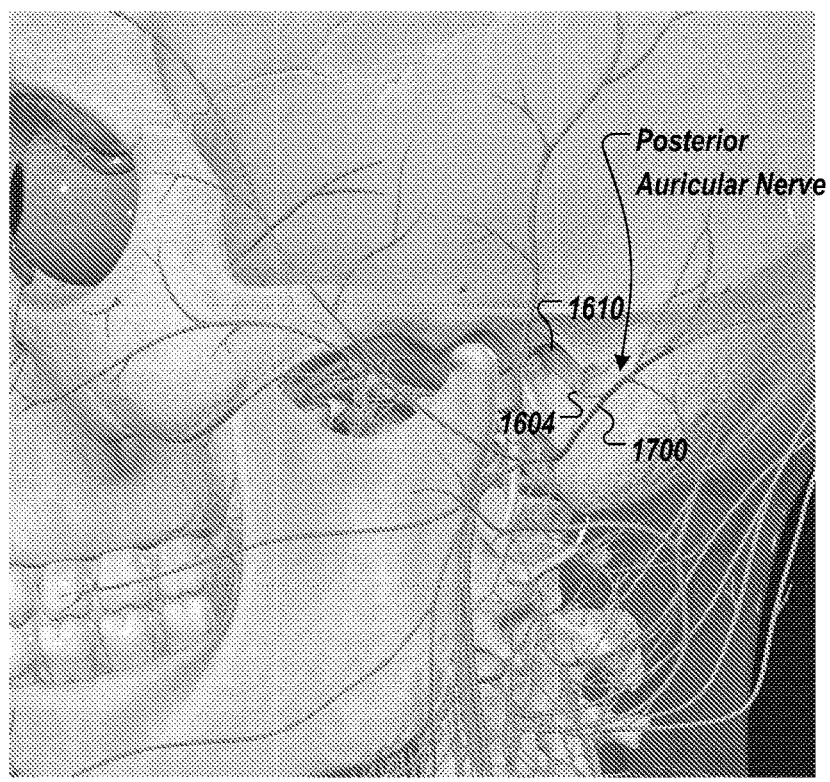

In some embodiments, the conductive adhesive region 1506 is configured to contact skin of a wearer in a region of nerve structures of the auricular branch of the vagus nerve (ABVN) and/or nerve structure connected to the ABVN such that delivery of therapeutic stimulations via the conductive adhesive region 1506 modulates ABVN activity. As shown in FIG. 16A through FIG. 16D for example, ABVN 1604 is illustrated as it surfaces (FIG. 16D) through the mastoid canaliculus (MsC) 1612 (e.g., Arnold's canal) and in relation to the ear 1600 (FIG. 16A), in relation to the ear canal 1610 (FIG. 16B) and in relation to the back of the ear (FIG. 16C). Turning to FIG. 17, posterior auricular nerve 1700 meets a branch of the ABVN, providing another target for ABVN stimulation. In an illustrative example, an electrode in electrical communication with the conductive adhesive region 1506 may be positioned in proximity to the MsC.

The conductive adhesive region 1508, in some embodiments, is configured to contact skin of the patient as a return electrode, thereby forming an electrical circuit across the tissue with the electrodes corresponding to each of the forward conductive adhesive region 1510 and the rear conductive adhesive region 1506. Although illustrated as a single return electrode (e.g., region 1508) for each positive electrode corresponding to adhesive region 1510 and adhesive region 1506, in other embodiments, separate return electrodes may be provided for each positive electrode. In further embodiments, three or more return electrode paths may be provided for the two positive electrodes. Other combinations are possible.

Figure 18:
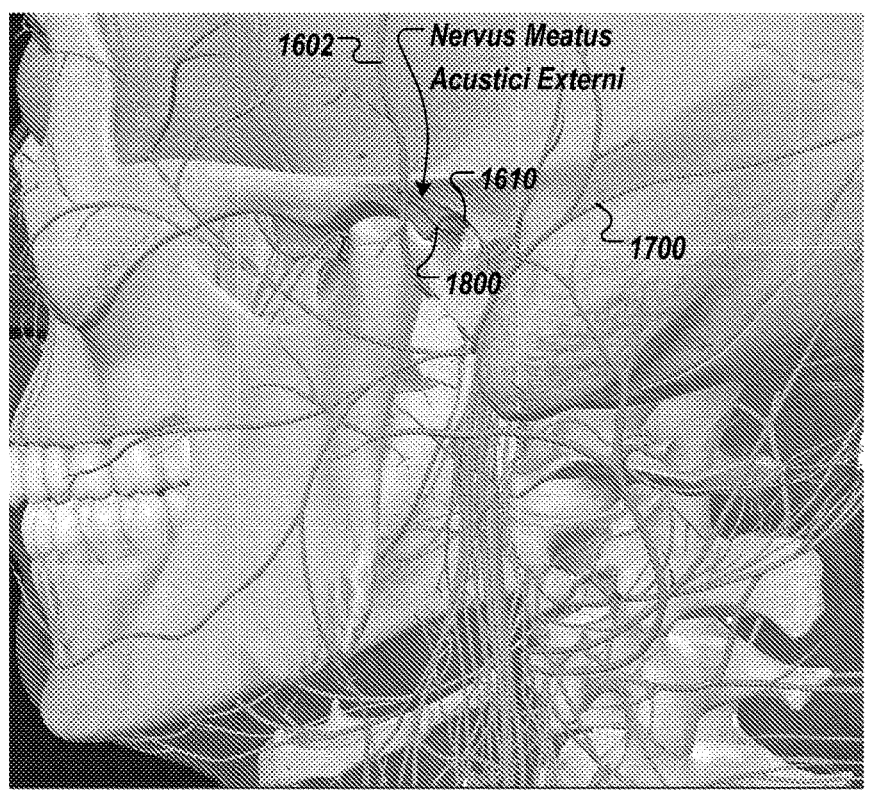

Turning to FIG. 8B, a conductive adhesive region may similarly be provided to create an electrical communication path from an electrode positioned on the first portion 806b of the inner ear component 806 of the WANS 800 to skin of the wearer in an anterior part of the ear canal. Turning to FIG. 18, such an electrode, for example, may be positioned to stimulate the nervus meatus acustici externi branch 1800 of the ATN 1602.

As illustrated in FIG. 15, a non-conductive adhesive may be provided generally in regions 1512a (e.g., around conductive adhesive 1510) and 1512b (e.g., between conductive regions 1506 and 1508, around region 1508, and at least partially around region 1506). The non-conductive adhesive, for example, may be used to electrically isolate conductive regions created through electrical communication between electrodes and the conductive adhesive 1506, 1508, and 1510. In this manner, the non-conductive adhesive may be used to avoid short-circuiting of the WANS apparatus 1500. The non-conductive adhesive, in some examples, may be deposited (e.g., sprayed, three-dimensionally printed, etc.) on one or more exterior surfaces of the WANS device 1500. In some embodiments, the non-conductive adhesive is a double-sided tape that is positioned manually or robotically on the WANS apparatus 1500. Rather than using a non-conductive adhesive, in other embodiments, a gripping material and/or pattern is molded into and/or three-dimensionally printed onto sections of the WANS apparatus 1500. For example, three-dimensional adhesive microstructures may be provided on the surface of the WANS 1500 to increase retention of the WANS apparatus 1500 about the wearer's ear.

In some implementations, one or more liners 1514 are placed over the adhesive regions to maintain stickiness and cleanliness of the adhesive material prior to wearing. As illustrated in FIG. 15, for example, a forward liner 1514a is illustrated as covering the adhesive regions 1510 and 1512a of the forward section 1502, and a rear liner 1514b is illustrated as covering the adhesive regions 1506, 1508, and 1512b of the rear section 1504. In other embodiments, a single liner may be provided to cover all adhesive regions of the WANS 1500.

Reference has been made to illustrations representing methods and systems according to implementations of this disclosure. Aspects thereof may be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/operations specified in the illustrations.

One or more processors can be utilized to implement various functions and/or algorithms described herein. Additionally, any functions and/or algorithms described herein can be performed upon one or more virtual processors, for example on one or more physical computing systems such as a computer farm or a cloud drive.

Aspects of the present disclosure may be implemented by hardware logic (where hardware logic naturally also includes any necessary signal wiring, memory elements and such), with such hardware logic able to operate without active software involvement beyond initial system configuration and any subsequent system reconfigurations. The hardware logic may be synthesized on a reprogrammable computing chip such as a field programmable gate array (FPGA), programmable logic device (PLD), or other reconfigurable logic device. In addition, the hardware logic may be hard coded onto a custom microchip, such as an application-specific integrated circuit (ASIC). In other embodiments, software, stored as instructions to a non-transitory computer-readable medium such as a memory device, on-chip integrated memory unit, or other non-transitory computer-readable storage, may be used to perform at least portions of the herein described functionality.

Various aspects of the embodiments disclosed herein are performed on one or more computing devices, such as a laptop computer, tablet computer, mobile phone or other handheld computing device, or one or more servers. Such computing devices include processing circuitry embodied in one or more processors or logic chips, such as a central processing unit (CPU), graphics processing unit (GPU), field programmable gate array (FPGA), application-specific integrated circuit (ASIC), or programmable logic device (PLD). Further, the processing circuitry may be implemented as multiple processors cooperatively working in concert (e.g., in parallel) to perform the instructions of the inventive processes described above.

The process data and instructions used to perform various methods and algorithms derived herein may be stored in non-transitory (i.e., non-volatile) computer-readable medium or memory. The claimed advancements are not limited by the form of the computer-readable media on which the instructions of the inventive processes are stored. For example, the instructions may be stored on CDs, DVDs, in FLASH memory, RAM, ROM, PROM, EPROM, EEPROM, hard disk or any other information processing device with which the computing device communicates, such as a server or computer. The processing circuitry and stored instructions may enable the pulse generator 1004 of FIG. 10A through FIG. 10C or the pulse generator 1150 of FIG. 11 to perform various methods and algorithms described above. Further, the processing circuitry and stored instructions may enable the peripheral device(s) 1010 of FIG. 10A through FIG. 10C to perform various methods and algorithms described above.

These computer program instructions can direct a computing device or other programmable data processing apparatus to function in a particular manner, such that the instructions stored in the computer-readable medium produce an article of manufacture including instruction means which implement the function/operation specified in the illustrated process flows.

Embodiments of the present description rely on network communications. As can be appreciated, the network can be a public network, such as the Internet, or a private network such as a local area network (LAN) or wide area network (WAN) network, or any combination thereof and can also include PSTN or ISDN sub-networks. The network can also be wired, such as an Ethernet network, and/or can be wireless such as a cellular network including EDGE, 3G, 4G, and 5G wireless cellular systems. The wireless network can also include Wi-Fi, Bluetooth, Zigbee, or another wireless form of communication. The network, for example, may be the network 1020 as described in relation to FIG. 10A through FIG. 10C.

The computing device, such as the peripheral device(s) 1010 of FIGS. 10A-10C, in some embodiments, further includes a display controller for interfacing with a display, such as a built-in display or LCD monitor. A general purpose I/O interface of the computing device may interface with a keyboard, a hand-manipulated movement tracked I/O device (e.g., mouse, virtual reality glove, trackball, joystick, etc.), and/or touch screen panel or touch pad on or separate from the display.

A sound controller, in some embodiments, is also provided in the computing device, such as the peripheral device(s) 1010 of FIG. 10A through FIG. 10C, to interface with speakers/microphone thereby providing audio input and output.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry or based on the requirements of the intended back-up load to be powered.

Certain functions and features described herein may also be executed by various distributed components of a system. For example, one or more processors may execute these system functions, where the processors are distributed across multiple components communicating in a network such as the network 1020 of FIG. 10A through FIG. 10C. The distributed components may include one or more client and server machines, which may share processing, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process.

Although provided for context, in other implementations, methods and logic flows described herein may be performed on modules or hardware not identical to those described. Accordingly, other implementations are within the scope that may be claimed.

In some implementations, a cloud computing environment, such as Google Cloud Platform™, may be used perform at least portions of methods or algorithms detailed above. The processes associated with the methods described herein can be executed on a computation processor of a data center. The data center, for example, can also include an application processor that can be used as the interface with the systems described herein to receive data and output corresponding information. The cloud computing environment may also include one or more databases or other data storage, such as cloud storage and a query database. In some implementations, the cloud storage database, such as the Google Cloud Storage, may store processed and unprocessed data supplied by systems described herein.

The systems described herein may communicate with the cloud computing environment through a secure gateway. In some implementations, the secure gateway includes a database querying interface, such as the Google BigQuery platform.

While certain embodiments have been described, these embodiments have been presented by way of example only and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A method for inhibiting, reducing or eliminating motion sickness using neuromodulation, the method comprising:
    placing at least one first electrode on, over, or adjacent to one or more first neural structures of a first set of neural structures, wherein
        each electrode of the at least one first electrode is placed against or at least partially into a respective first tissue region on or adjacent an ear of a subject;
    placing at least one second electrode on, over or adjacent to one or more second neural structures of a second set of neural structures, wherein
        each electrode of the at least one second electrode is placed against or at least partially into a respective second tissue region on or adjacent the ear of the subject; and
    delivering, by a pulse generator, therapeutic stimulation pulses for treating motion sickness of the subject without causing sedation and/or drowsiness, wherein delivering the therapeutic stimulation pulses comprises
        delivering a first series of stimulation pulses to the at least one first electrode, wherein the first series of stimulation pulses is configured to modulate peripheral activity via modulating central neural autonomic structures, and
        delivering a second series of stimulation pulses to the at least one second electrode, wherein the second series of stimulation pulses is configured to modulate one or more areas in a brain stem of the subject.

2. The method of claim 1, wherein modulating the central neural autonomic structures comprises modulating the paraventricular hypothalamic nucleus (PVN) to stimulate increased activity in the pituitary.

3. The method of claim 1, wherein modulating the peripheral activity comprises producing an increase in peripheral circulating beta-endorphins.

4. The method of claim 1, wherein at least one of the first set of neural structures or the second set of neural structures are in direct or indirect communication with an auriculotemporal nerve (ATN).

5. The method of claim 1, wherein at least one of the first set of neural structures or the second set of neural structures are in direct or indirect communication with an auricular branch of a vagus nerve (ABVN).

6. The method of claim 1, wherein at least one of the first series of stimulation pulses and the second series of stimulation pulses is configured to increase serotonin (5-HT) availability.

7. The method of claim 1, wherein:
    the first series of stimulation pulses are delivered at one or more low frequencies selected from a first frequency range up to 30 Hertz; and
    the second series of stimulation pulses are delivered at i) one or more mid-range frequencies selected from a second frequency range from 31 Hertz to 70 Hertz or ii) one or more high frequencies selected from a third frequency range from 71 Hertz to 150 Hertz.

8. The method of claim 1, further comprising:
    monitoring, by one or more sensors, physical movements of the subject or a device worn by the subject;
    wherein delivering the therapeutic stimulation pulses comprises initiating the therapeutic stimulation pulses responsive to analyzing, by control circuitry, at least one feedback signal from the one or more sensors to identify one or more situational triggers indicative of likelihood of motion sickness.

9. The method of claim 8, wherein a device comprising the one or more sensors is separate from a therapeutic neuromodulation system comprising the pulse generator, the at least one first electrode, and the at least one second electrode.

10. The method of claim 8, wherein the one or more sensors comprises at least one of a motion detector, an accelerometer, or a gyroscope.

11. The method of claim 10, wherein the one or more situational triggers comprise at least one of exposure to G-forces, exposure to turbulence, flying in a substantially non-vertical orientation, or exposure to choppiness and/or swells while on or in water.

12. The method of claim 1, wherein:
a virtual reality (VR) device comprises the at least one first electrode and the at least one second electrode; and
delivering the therapeutic stimulation pulses comprises initiating the therapeutic stimulation pulses based on activating a VR program.

13. The method of claim 1, wherein treating the motion sickness comprises treating space adaptation syndrome in a microgravity environment.

14. The method of claim 1, wherein:
one or more electrodes of the at least one first electrode is placed behind the auricle; and
a given neural structure of the one or more first neural structures corresponding to the placement of the one or more electrodes is the auricular branch of the vagus nerve (ABVN) near a point at which the ABVN surfaces through the mastoid canaliculus (MsC).

15. The method of claim 1, wherein:
one or more electrodes of the at least one second electrode is placed forward of the auricle; and
a given neural structure of the one or more second neural structures corresponding to the placement of the one or more electrodes is a branch of the auriculotemporal nerve (ATN).

16. The method of claim 15, wherein the branch of the ATN is the nervus meatus acustici externi.

17. The method of claim 1, wherein placing the at least one first electrode and placing the at least one second electrode comprises donning, by the subject, a protective helmet comprising one or more electrodes of the at least one first electrode and one or more electrodes of the at least one second electrode.

18. The method of claim 1, wherein:
a head-mounted neurostimulation device comprises the at least one first electrode, the at least one second electrode, and the pulse generator; and
placing the at least one first electrode and placing the at least one second electrode comprises donning, by the subject, the head-mounted neurostimulation device.

19. The method of claim 1, wherein modulating the one or more areas in the brain stem comprises modulating the locus coeruleus (LC) to increase availability of central norepinephrine (NE).

20. The method of claim 19, wherein the second series of stimulation pulses is further configured to modulate activity in the vestibular nuclei (VN).

21. The method of claim 1, wherein treating the motion sickness comprises treating spatial disorientation.

* * * * *